(12) United States Patent
Orlow et al.

(10) Patent No.: US 7,604,949 B2
(45) Date of Patent: Oct. 20, 2009

(54) METHODS AND COMPOSITIONS THAT AFFECT MELANOGENESIS

(75) Inventors: Seth J. Orlow, New York, NY (US); Andrea Hall, Astoria, NY (US); Prashiela Manga, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/408,108

(22) Filed: Apr. 20, 2006

(65) Prior Publication Data

US 2006/0188953 A1 Aug. 24, 2006

Related U.S. Application Data

(60) Division of application No. 10/758,335, filed on Jan. 15, 2004, which is a division of application No. 09/827,428, filed on Apr. 6, 2001, now abandoned, which is a continuation-in-part of application No. 09/599,487, filed on Jun. 23, 2000, now abandoned.

(60) Provisional application No. 60/141,563, filed on Jun. 29, 1999.

(51) Int. Cl.
*G01N 33/53* (2006.01)
(52) U.S. Cl. .................................................. 435/7.1
(58) Field of Classification Search .................. 435/4, 435/7.1
See application file for complete search history.

(56) References Cited

U.S. PATENT DOCUMENTS

| | | | |
|---|---|---|---|
| 3,062,846 A | 11/1962 | Fried | |
| 3,155,591 A | 11/1964 | Hilfer et al. | |
| 3,210,386 A | 10/1965 | Birkenmeyer et al. | |
| 3,389,051 A | 6/1968 | Kagan et al. | |
| 3,755,560 A | 8/1973 | Dickert et al. | |
| 3,929,678 A | 12/1975 | Laughlin et al. | |
| 3,959,461 A | 5/1976 | Bailey et al. | |
| 4,139,619 A | 2/1979 | Chidsey, III | |
| 4,278,656 A | 7/1981 | Nagai et al. | |
| 4,369,174 A | 1/1983 | Nagai et al. | |
| 4,387,090 A | 6/1983 | Bolich, Jr. | |
| 4,421,769 A | 12/1983 | Dixon et al. | |
| 4,439,432 A | 3/1984 | Peat | |
| 4,684,635 A | 8/1987 | Orentreich et al. | |
| 4,935,352 A | 6/1990 | Igarashi et al. | |
| 4,959,313 A | 9/1990 | Taketo | |
| 4,959,393 A | 9/1990 | Torihara et al. | |
| 5,011,681 A | 4/1991 | Ciotti et al. | |
| 5,073,371 A | 12/1991 | Turner et al. | |
| 5,073,372 A | 12/1991 | Turner et al. | |
| 5,120,532 A | 6/1992 | Wells et al. | |
| 5,151,209 A | 9/1992 | McCall et al. | |
| 5,151,210 A | 9/1992 | Steuri et al. | |
| 5,214,028 A | 5/1993 | Tomita et al. | |
| 5,232,917 A | 8/1993 | Bolger et al. | |
| 5,302,517 A | 4/1994 | Rhode, III | |
| 5,389,611 A | 2/1995 | Tomita et al. | |
| 5,512,483 A | 4/1996 | Mader et al. | |
| 5,569,678 A | 10/1996 | Lee | |
| 5,580,549 A | 12/1996 | Fukuda et al. | |
| 5,591,423 A | 1/1997 | Fuller | |
| 5,616,332 A | 4/1997 | Herstein | |
| 5,627,033 A | 5/1997 | Smith et al. | |
| 5,628,987 A | 5/1997 | Fuller | |
| 5,665,578 A | 9/1997 | Gillies | |
| 5,681,744 A | 10/1997 | Greenstein | |
| 5,686,103 A | 11/1997 | Redziniak et al. | |
| 5,691,380 A | 11/1997 | Mason et al. | |
| 5,789,215 A | 8/1998 | Berns et al. | |
| 5,811,260 A | 9/1998 | Miyazaki et al. | |
| 5,814,618 A | 9/1998 | Bujard et al. | |
| 5,827,687 A | 10/1998 | Koyama et al. | |
| 5,840,525 A | 11/1998 | Vandlen et al. | |
| 5,849,997 A | 12/1998 | Grosveld et al. | |
| 5,851,984 A | 12/1998 | Matthews et al. | |
| 5,861,290 A | 1/1999 | Goldsmith et al. | |
| 5,968,528 A | 10/1999 | Deckner et al. | |
| 5,993,835 A | 11/1999 | Mishima et al. | |
| 6,123,959 A | 9/2000 | Jones et al. | |
| 6,132,740 A | 10/2000 | Hu | |
| 6,139,854 A | 10/2000 | Kawato | |

(Continued)

FOREIGN PATENT DOCUMENTS

EP 0 993 826 A1 4/2000

(Continued)

OTHER PUBLICATIONS

Kim et al (Int. J. Cancer, 2006, 118:1670-1679).*

(Continued)

*Primary Examiner*—Sean E Aeder
(74) *Attorney, Agent, or Firm*—Wilmer Cutler Pickering Hale and Dorr LLP

(57) ABSTRACT

The invention provides methods of screening for compounds that affect melanogenesis and the function of P protein in organisms, cells, or cell-free systems. The invention further relates to pharmacologic and cosmetic uses of methods of inhibiting melanogenesis, methods of activating melanogenesis, and compounds and pharmacologic compositions useful for the inhibition or activation of melanogenesis and, therefore, for lightening or darkening the pigmentation of cells and tissue, i.e., skin.

12 Claims, 19 Drawing Sheets

U.S. PATENT DOCUMENTS

| | | | |
|---|---|---|---|
| 6,159,482 | A | 12/2000 | Tuloup et al. |
| 6,197,830 | B1 | 3/2001 | Frome |

FOREIGN PATENT DOCUMENTS

| | | | |
|---|---|---|---|
| EP | 0 993 826 B1 | | 4/2000 |
| EP | 0 997 140 A1 | | 5/2000 |
| EP | 0 997 140 B1 | | 5/2000 |
| JP | 8-337528 | | 12/1996 |
| WO | WO-88/09810 | | 12/1988 |
| WO | WO-90/11364 | | 10/1990 |
| WO | WO-97/00892 | | 1/1997 |
| WO | WO-98/37897 | | 9/1998 |
| WO | WO-98/49999 | | 11/1998 |
| WO | WO-99/04752 A2 | | 2/1999 |
| WO | WO-99/09011 | | 2/1999 |
| WO | WO-99/32077 | | 7/1999 |
| WO | WO-99/56740 | | 11/1999 |
| WO | WO-99/64025 | | 12/1999 |
| WO | WO-00/56702 | | 9/2000 |
| WO | WO-00/58549 | | 10/2000 |
| WO | WO-00/62742 | | 10/2000 |
| WO | WO-00/76473 | | 12/2000 |
| WO | WO-01/01131 | | 1/2001 |
| WO | WO-02/49580 | | 6/2002 |

OTHER PUBLICATIONS

Hall et al (Pigment Cell Research, 2003, 16:149-158).*
McCurdy (J. Cell Bio., 1969, 43(2):220-228).*
Seiberg et al (J. Invest. Dermatol., 2000, 115(2):162-167).*
Imokawa (Jul. 1989, Journal of Investigative Dermatology, 93(1):100-7).*
Dennell (May 1949, Proceedings of the Royal Society of London, 136(882): 94-109).*
Rosemblat et al (Mar. 1998, Experimental Cell Research, 239:344-352).*
Palumbo et al (Mar. 1997, Biochem J, 323:749-756).*
Lamoreux et al (Oct. 1995, Pigment Cell Research, 8(5): 263-70).*
Borovansky et al (Feb. 1997, Arch Dermatol Res, 289: 145-150).*
The Merck Index, 12$^{th}$ Edition (1996, Merck & Co., Inc., Whitehouse Station, N.J., pp. 581, 845, 1154, 1358 and 1656).
Blanchette-Mackie E. J. "Intraceullular cholesterol trafficking: role of the NCP1 protein" *Biochemica and Biophysica Acta. Molecular and Cell Biology of Lipids*, Elsevier, Amsterdam, NL. vol. 1486, No. 1, Jun. 2000. pp. 171-183.
Haermaelae A. S. et al. "Cholesterol Transport from Plasma Membranes to Intracellular Membranes is Inhibited by 3-Beta-(2-(Diethylamino)Ethoxy)and Rost-5-en-17-one" *Biochemica et Biophysica Acta*—Lips and Lipid Metabolism, Elsevier Science BV Amsterdam, NL. vol. 1211, No. 3, Mar. 1994, pp. 317-325.
Lange Y et al. "Cholesterol Movement in Niemann-Pick Type C Cells and in Cells Treated with Amphiphiles." *Journal of Biological Chemistry*, American Society of Biochemical Biologists, Birmingham, U.S. vol. 275, No. 23, Jun. 9, 2000. pp. 17468-17475.
Lange Y. et al. "Cholesterol Homeostatis Modulation By Amphiphiles." Journal of Biological Chemistry, American Society of Biochemical Biologists, Birmingham, US. vol. 269, No. 47, Nov. 1994. pp. 29371-29374.
Liscum L. et al. "Intracellular Cholesterol Transport." *Journal of Lipid Research* 1999. United States, vol. 33, No. 9, 1992. pp. 1239-1254.
Supplemental, Partial European Search Report, corresponding to European Application No. 02776548.6, mailed Nov. 27, 2007, 4 pages.
Vippagunta et al. "Crystalline solids" Advanced Drug Delivery Reviews 48 (2001) 3-26.
Abdel-Malek, et al., "Mitogenic, Melanogenic and cAMP Responses of Cultured Neonatal Human Melanocytes to Commonly Used Mitogens", Journal of Cellular Physiology, 150:416-425 (1992).

Adams, et al., "The c-myc Oncogene Driven by Immunoglobulin Enhancers Induces Lymphoid Malignancy in Transgenic Mice", 318:533-538 (1985).
Alexander, et al., "Expression of the c-myc Oncogene Under Control of an Immunoglobulin Enhancer in Eu-myc Transgenic Mice", Molecular and Cellular Biology, 7(4):1436-1444 (1987).
Ancans, et al., "Activation of Melanogenesis by Vacuolar Type H4$^+$-ATPase Inhibitors in Amelanotic, Tyrosinase Positive Human and Mouse Melanoma Cells", FEBS Letters, 478:57-60 (2000).
Ansel, et al. *Pharmaceutical Dosage Forms and Drug Delivery Systems*, Sixth Ed., A Lea & Febiger Book, Williams & Wilkins, Baltimore (1995).
Bayer, et al., EMBASE 1998386460, J. Virology, 72(12):9645-9655 (1998) (Abstract).
Bennett, et al., "Line of Non-Tumorigenic Mouse Melanocytes . . . ", Int. J. Cancer, 39:414-418 (1987).
Benoist, et al., "In Vivo Sequence Requirements of the SV40 Early Promoter Region", Nature, 290:304-310 (1981).
Bouchard, et al., "Induction of Pigmentation in Mouse Fibroblasts by Expression of Human Tyrosinase cDNA", J. Exp. Med., 169:2029-2042 (1989).
Bowman, et al, "Bafilomycins: a Class of Inhibitors of Membrane ATPases From Microorganisms . . . ", Proc. Natl. Acad. Sci., 85:7972-7976 (1988).
Brilliant, et al., "Anatomy of Pigment Cell Genes Acting at the Cellular Lever", in *The Pigmentary System: Physiology and Pathophysiology*, Norlund, et al., eds., Oxford University Press, Chapter 18, pp. 217-229 (1998).
Brinster, et al., "Regulation of Methallothionein-thymidine Kinsase Fusion Plasmids Injected into Mouse Eggs", Nature, 296:39-42 (1982).
Chakraborty, et al., "Effect of Arbutin on Melanogenic Proteins in Human Melanocytes", Pigment Cell Research, 11:206-212 (1998).
Chang, et al., "Rat Gene Encoding the 78-kDa Glucose-Regulated Protein GRP78", Porc. Natl. Acad. Sci., 84:680-684 (1987).
Cohen, et al., Psychiat. Res. Repts., 1:11-13 (1995) Abstract.
Deboer, et al., "The tac Promoter: a Functional Hybrid Derived from the trp and iac Promoters", Proc. Natl. Acad. Sci., 80:21-25 (1983).
Dell'Angelica, et al., "Altered Trafficking of Lysosomal Proteins . . . ", Molecular Cell, 3:11-21 (1999).
Drose, et al., "Bafilomycins and Concanamycins as Inhibitors of V-ATPases and P-ATPases", The Journal of Experimental Biology, pp. 1-8 (1997).
Furumura, et al., "Characterization of Genes Modulated During Pheomelanogenesis . . . ", Proc. Natl. Acad. Sci., 95:7374-7378 (1998).
Gahl, et al., "Melanosomal Tyrosine Transport in Normal and Pink-Eyed Dilution Murine Melanocytes", Pigment Cell Res., 8:229-233 (1995).
Gardner, et al., "The Complete Nucleotide Sequence of an Infectious Clone of Cauliflower Mosaic Virus by M13mp7 Shotgun Sequencing", Nucleic Acids Research, 9(12):2871-2888 (1981).
Gardner, et al., "The Mouse Pink-Eyed Dilution Gene . . . ", Science, 257:1121-1124 (1992).
Gautier, et al., "DNA IV: enomeric and β-anomeric Tetrathymidylates . . . ", Nucleic Acids Research, 15(16):6625-6641 (1987).
Gilbert, et al., "Useful Proteins from Recombinant Bacteria", Sci. Am., 242(4):74-94 (1980).
Gossen, et al., "Tight Control of Gene Expression in Mammalian Cells . . . ", Proc. Natl. Acad. Sci., 89:5547-5551 (1992).
Gossen, et al., "Transcriptional Activation by Tetracyclines in Mammalian Cells", Science, 268:1766-1769 (1995).
Grosschedi, et al., "Introduction of a u-Immunoglobulin Gene into the Mouse Germ Line . . . ", Cell, 38:647-658 (1984).
Hammer, et al., "Diversity of Alpha-Fetoprotein Gene Expression in Mice . . . ", Research Articles, 235:53-58 (1987).
Hanahan, "Heritable Formation of Pancreatic β-cell Tumors in Transgenic Mice Expressing Recombinant Insulin/Simian Virus 40 Oncogenes", Nature, 315:115-122 (1985).
Harlow, et al. *Antibodies—A Laboratory Manual*, Cold Spring Harbor Laboratory (1988). (cover of book and page (i)).

Hashizume, et al., CA126:190762, JP 08337528 A2 (1996) (Abstract).
Hearing, "Invited Editorial: Unraveling the Melanocyte", Am. J. Hum. Genet., 52(1):1-7 (1993).
Herrera-Estrella, et al., "Expression of Chimaeric Genes Transferred into Plant Cells Using a Ti-plasmid-derived Vector", Nature, 303:209-213 (1983).
Herrera-Estrella, et al., "Light-Inducible and Chloroplast-Associated Expression of a Chimaeric Gene Introduced into Nicotiana Tabacum . . . ", Nature, 310:115-120 (1984).
Higgins, et al., "Niemann-Pick C1 is a Late Endosome-Resident Protein that Transiently . . . ", Molecular Genetics and Metabolism, 68:1-13 (1999).
Hu, et al., "Regulation of Melanogenesis by Human Uveal Melanocytes in Vitro", Exp. Eye Res., 64:397-404 (1997).
Iida, et al., "Potent Inhibitors of Tyrosinase Activity and Melanin", Planta Med., 61:425-428 (1995).
Imokawa, et al., "Skin Organ Culture Model for Examining Epidermal Melanization", Journal of Investigative Dermatology, 100:47-54 (1993).
Inoue, et al., "Sequence-Dependent Hydrolysis of RNA . . . ", FEB, 215(2):327-330 (1987).
Inoue, et al., "Synthesis and Hybridization Studies on Two Complementary . . . ", Nucleic Acids Research, 15(15):6131-6148 (1987).
Jimenez, et al., "Tyrosinases from Two Different Loci are Expressed by Normal and by Transformed Melanocytes", Journal of Biological Chemistry, 266(2):1147-1156 (1991).
Kelsey, et al., "Species-and Tissue-Specific Expression of Human a1-antitrypsin in Transgenic Mice", Genes & Development, 1:161-171 (1987).
Kobayashi, et al., "Late Endosomal Membranes Rich in Lysobisphosphatidic Acid Regulate . . .", Nature Cell Biology, 1:113-118(1999).
Kobayashi, et al., "The Tetraspanin CD63/Lamp3 Cycles Between Endocytic and Secretory Compartments", Molecular Biology of the Cell, 11:1829-1843 (2000).
Kollias, et al., "Regulated Expression of Human Ay-B- and Hybrid yB-Globin Genes . . . ", Cell, 46:89-94 (1986).
Korner, et al., "Mammalian Tyrosinase Catalyzes Three Reactions in the Biosynthesis of Melanin", Science, 217:1163-1165 (1982).
Kromberg, "Albinism and Skin Cancer in Southern Africa", Cliinical Genetics, 36:43-52 (1989).
Krumnlauf, et al., "Developmental Regulation of a-Fetoprotein Genes in Transgenic Mice", Molecular and Cellular Biology, 5(7):1639-1648 (1985).
Kuzumaki, et al., "Eumelanin Biosynthesis is Regulated by Coordinate Expression of Tyrosinase and Tyrosinase-Related Protein-1 Genes", Experimental Cell Research, 207:33-40 (1993).
Lamoreux, et al., "The Pink-Eyed-Dilution Protein and the Eumelanin/Pheomelanin Switch", Pigment Cell Research, 8:263-270 (1995).
Lange, "Circulation of Cholesterol Between Lysosomes and the Plasma Membrane", Journal of Biological Chemistry, 273(30):18915-18922 (1998).
Leder, et al., "Consequences of Widespread Deregulation of the c-myc Gene in Transgenic Mice", Cell, 45:485-495 (1988).
Lemaitre, et al., "Specific Antiviral Activity of a Poly (L-lysine)-conjugated Oligodeoxyribonucleotide Sequence . . . ," Proc. Natl. Acad. Sci, 84:648-652 (1987).
Lerner, et al., "Biochemistry of Melanin Formation", Physiol. Rev., 30(1):91-126 (1950).
Letsinger, et al., "Cholesteryl-conjured Oligonucleotides: Synthesis, Properties, and Activity . . . ", Proc. Natl. Acad. Sci., 86:6553-6556, (1989).
Liscum, et al., "Intracellular Cholesterol Transport", Biochem et Biophysica Acta, 1438:19-37 (1999).
Macdonald, "Expression of the Pancreatic Elastase I Gene in Transgenic Mice", Hepatoloty, 7(1):42S-51S (1987).
Magram, et al., "Developmental Regulation of a Cloned Adult . . . ", Nature, 315:338-340 (1985).
Manga, et al., "The Pink Eyed Dilution Gene and the Molecular Pathogenesis of Tyrosinase-Positive Albinism", Journal of Dermatology, 26:738-747 (1999).

Mason, et al., "The Hypogonadal Mouse: Reproductive Functions Restored by Gene Therapy", Science, 234(4782):1372-1378 (1986).
McLeod, et al., "Stimulation of Tyrosinase in Human Melanocytes by Pro-opiomelanocortin-derived Peptides", Journal of Endocrinology, 146:439-447 (1995).
Medline 67014260, Gibbard, Am. J. Psychiatry, 123(3):351-352 (1966) (Abstract).
Medline 89379530, George, Int.. J. Dermatoloty, 28(7):475-477 (1989) (Abstract).
Medline AN 1998010047, Sabroe, et al., Br. J. Dermatol., 137(3):386-390 (1997) (Abstract).
Moyer, "Genetic Variations in the Fine Structure and Ontogeny . . . ", Am. Zoology, 6:45-66 (1966).
Niekrasz, et al., "The Pig as Organ Donor for Man", Transplantation Proceedings, 24(2):625-626 (1992).
Nir, et al., "Ultrastructural Analysis of Arrestin Distribution in Mouse Photoreceptors During Dark/Light Cycle", Exp. Eye Res., 57:307-318 (1993).
Oetting, et al., "Mutations of the Human P Gene Associated with Type II Oculocutaneous Albinism (OCA2)", Human Mutation, 12(6):434 (1998).
Orlow, "The Biogenesis of Melanosomes", in The Pigmentary System: Physiology and Pathophysiology, Norlund, et al., eds, Oxford University Press, Chapter 6, pp. 97-106 (1998).
Orlow, et al., "High-Molecular Weight Forms of Tyrosinase and the Tyrosinase-Related Proteins", 103(2):196-201 (1994).
Orlow, et al., "Retinoic Acid is a Potent Inhibitor of Inducible Pigmentation in Murine and Hamster Melanoma Cell Lines", Journal of Investigative Dermatology, 64(4):461-464, (1990).
Orlow, et al., "The Pink-Eyed Dilution Locus Controls the Biogenesis of Melanosomes . . . ", Exp. Eye Res., 68:147-154 (1999).
Ornitz, et al., "Elastase I Promoter Directs Expression of Human Growth Hormone and SV40 T Antigen Genes to Pancreatic Acinar Cells in Transgenic Mice", Cold Spring Harb. Symp. Quant. Biol., 50:399-409 (1985).
Patel, CA130:295103, Proceedings Nat. Acad. Sc. USA, 96(4):1657-1662 (1999) (Abstract).
Pinkert, et al., "An Albumin Enhancer Located 10 kb Upstream Functions Along with its Promoter to Direct Efficient, Liver-Specific Expression in Transgenic Mice", Genes & Development, 1:268-276 (1987).
Potterf, et al., "Normal Tyrosine Transport and Abnormal Tyrosinase Routing . . . ", Experimental Cell Research, 244:319-326 (1998).
Product Information Sigma: Composition of the Medium Ham's F10, (2006).
Product Information Sigma: Composition of the Medium MCDB-153, (2006).
Ramsay, et al., "The Tyrosinase-positive Oculocutaneous Albinism Locus Maps to Chromosome 15q11.2-q12", Am. J. Hum. Genet., 51:879-884 (1992).
Readhead, "Expression of a Myelin Basic Protein Gene in Transgenic Shiverer Mice . . . ", Cell, 48:703-712 (1987).
Reish, et al., "Tyrosinase Inhibition Due to Interaction of Homocyst(e)ine with Copper", Am. J. Hum. Genet., 57:127-132 (1995).
*Remington's Pharmaceutical Sciences, 18th Edition*, Alfonso Gennaro, Editor, Mack Publishing Company, Easton, PA (1990).
Resendez, Jr., et al., "Identification of Hightly Conserved Regulatory Domains and Protein-Binding Sites in the Promoters of the Rat and Human Genes Encoding...", Molecular and Cellular Biology, 8(10):4579-4584 (1988).
Riley, "Molecules in Focus", Int. J. Biochem. Cell. Biol., 29(11):1235-1239 (1997).
Rinchik, et al., "A Gene for the Mouse Pink-Eyed Dilution Locus . . . ", Nature, 361:72-76 (1993).
Roff, et al., "Type C Niemann-Pick Disease: Use of Hydrophobic Amines to Study Defective Cholesterol Transport", Dev. Neurosci, 13:315-319 (1991).
Rosemblat, et al., "Identification of a Melanosomal Membrane Protein Encoded by the Pink-Eyed Dilution Gene", Proc. Natl. Acad. Sci., 91:12071-12075 (1994).

Rosemblat, et al., "Melanosomal Defects in Melanocytes from Mice Lacking Expression of the Pink-Eyed Dilution Gene", Experimental Cell Research, 239:344-352 (1998).

Russell, "Quantitative Histological Study of the Pigment Found in the Coat Color of Mutants of the House Mouse", Genetics, 34:146-166 (1949).

Sakai, et al., "Modulation of Murine Melanocyte Function in vitro by Agouti Signal Protein", EMBO Journal, 16(12):3544-3552 (1997).

Sarin, et al., "Inhibition of Acquired Immunodeficiency Syndrome Virus by Oligodeoxynucleoside Methylphosphonates", Proc. Natl. Acad. Sci., 85:7448-7451 (1988).

Schwartz, et al., *Surface Active Agents, Their Chemistry and Technology*, Interscience Publishers, Inc, New York, NY (1949).

Seiberg, et al., "Inhibition of Melanosome Transfer Results in Skin Lightening", Journal of Investigative Dermatology, 115(2):162-167 (2000).

Seiji, et al., "Subcellular Localization of Melanin Biosynthesis", Annals NY Acad. Sci., 100:497-533 (1963).

Shani, "Tissue-Specific Expression of Rat Myosin Light-Chain 2 Gene in Transgenic Mice", Nature, 314:283-286 (1985).

Sharom, et al., "Characterization of the ATPase Activity of P-glycoprotein From Multidrug-Resistent . . . ", Biochem J., 308:381-390 (1995).

Shirota, et al., "Tyrosinase Inhibitors from Crude Drugs", Biol. Pharm. Bull., 17(2):266-269 (1994).

Sidman, et al., "Pink Eyed Dilution (p) Gene in Rodents: Increased Pigmentation in Tissue Culture", Developmental Biology, 12:93-116 (1985).

Silvers, *The Coat Colors of Mice*, Springer-Verlag (1979).

Smith, et at., "Mapping the Collagen-Binding Site in the I Domain . . . ", Journal of Biological Chemistry, 275:4205-4209 (2000).

Spritz, "Multi-Organellar Disorders of Pigmentation", TIG, 15(9):337-340 (1999).

Stein, et al., "Physicochemical Properties of Phosphorothioate Oligodeoxynucleotides", Nucleic Acids Research, 16(8):3209-3221 (1988).

Strum, et al.. "Ultrastructural Localization of Peroxidase in Sumaxillarv Acinar Cells", Ultrastructure Research, 31:323-336 (1970).

Sviderskaya, et al., "Complementation of Hypopigmentation in p-Mutant Mouse . . . ", Journal of Investigative Dermatology, 108(1):30-34 (1997).

Swift, et al., "Tissue Specific Expression of the Rat Pancreatic Elastase Gene in Transgeneic Mice", Cell, 38:639-464 (1984).

Szycher, et al., High Perform. Biomater., pp. 807-812 (1991) (Abstract).

Tasaka, et al., "Effects of Certain Resorcinol Derivatives on the Tyrosinase Activity and the Growth of Melanoma Cells", Meth. Find Exp. Clin. Pharmacol., 20(2):99-109 (1998).

Van Der Krol, et al., "Modulation of Eukaryotic Gene Expression by Complementary RNA or DNA Sequences", BioTechniques, 6(10):958-976 (1988).

Villa-Komaroff, et al., "A Bacterial Clone Synthesizing Proinsulin", Proc. Natl. Acad. Sci., 75(8):3727-3731 (1978).

Virador, et al., "A Standardized Protocol for Assessing Regulators of Pigmentation", Analytical Biochemistry, 270:207-219 (1999).

Wagner, et al., "Nucleotide Sequence of the Thymidine Kinase Gene of Herpes Simplex Virus Type 1", Proc. Natl. Acad. Sci., 78(3):1441-1445 (1981).

Webster's II New Riverside University Dictionary, p. 96, p. 72, (1984).

Yamamoto, et al., "Identification of a Functional Promoter in the Long Terminal Repeat of Rous Sarcoma Virus", Cell, 22:787-797 (1980).

Yokoyama, et al., "Conserved Cysteine to Serine Mutation in Tyrosinase is Responsible for the Classical Albino Mutation in Laboratory Mice", Nucleic Acids Research, 18(24):7293-7298 (1990).

Zon, "Oligonucleotide Analogues as Potential Chemotherapeutic Agents", Pharmaceutical Research, 5(9):539-549 (1988).

Baulieu, E.E. et al. "Dehydroepiandrosterone (DHEA), DHEA sulfate, and aging: contribution of the DHEAge Study to a sociobiomedical issue," PNAS, 2000, vol. 97, No. 8, pp. 4279-4284.

* cited by examiner

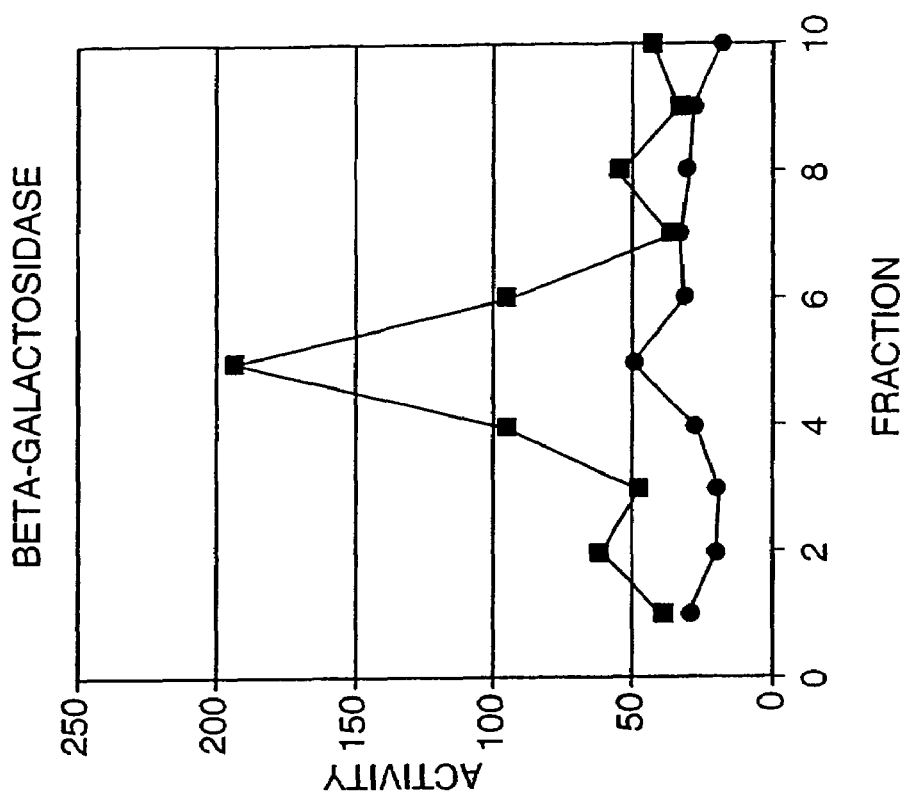
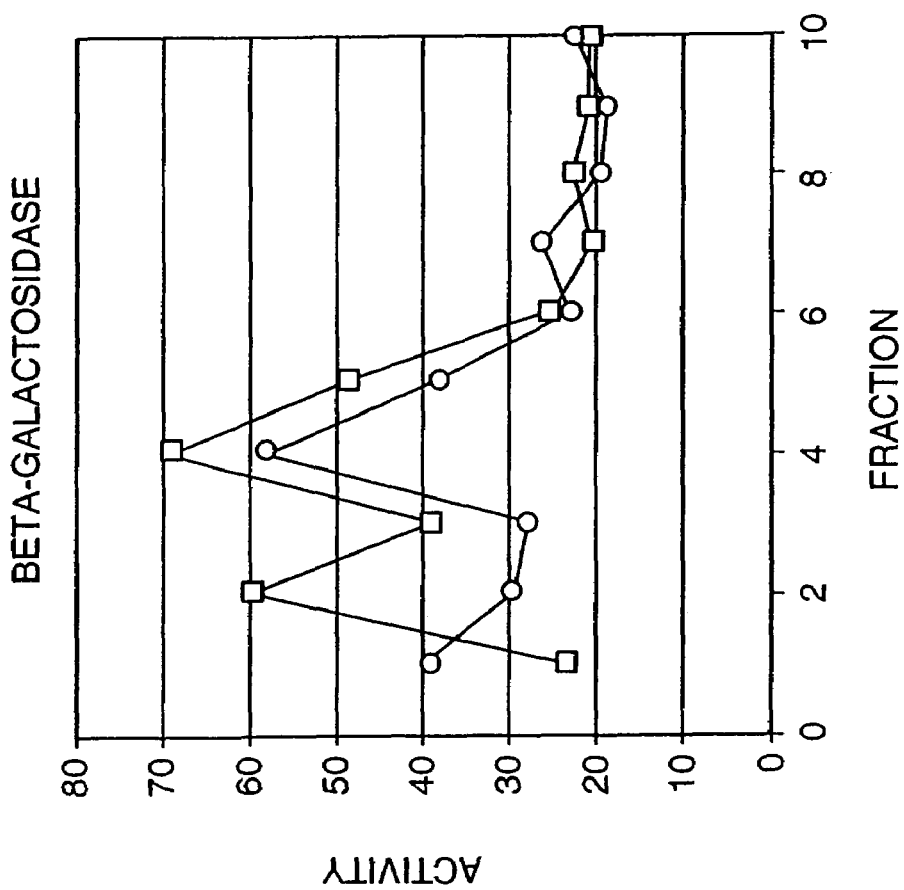

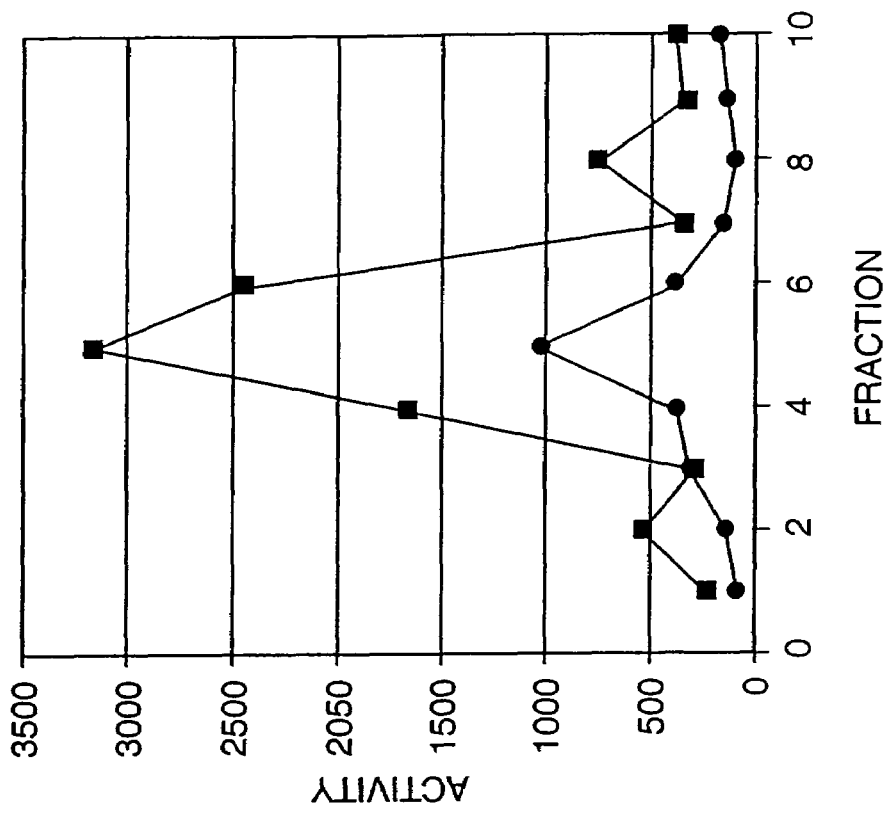
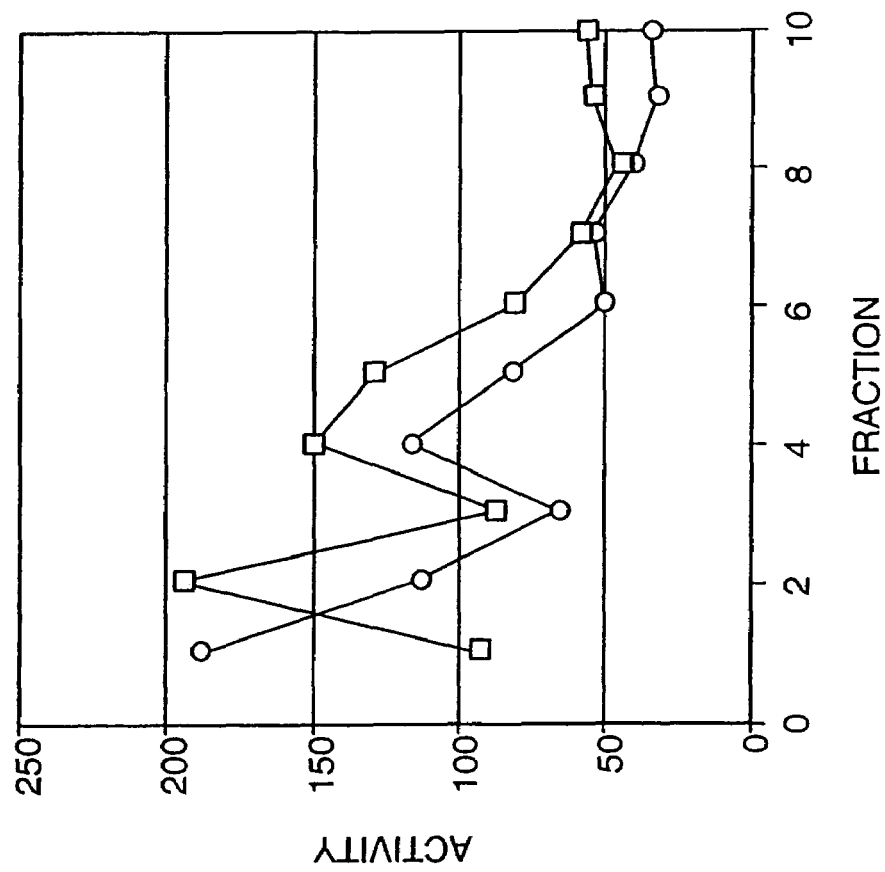

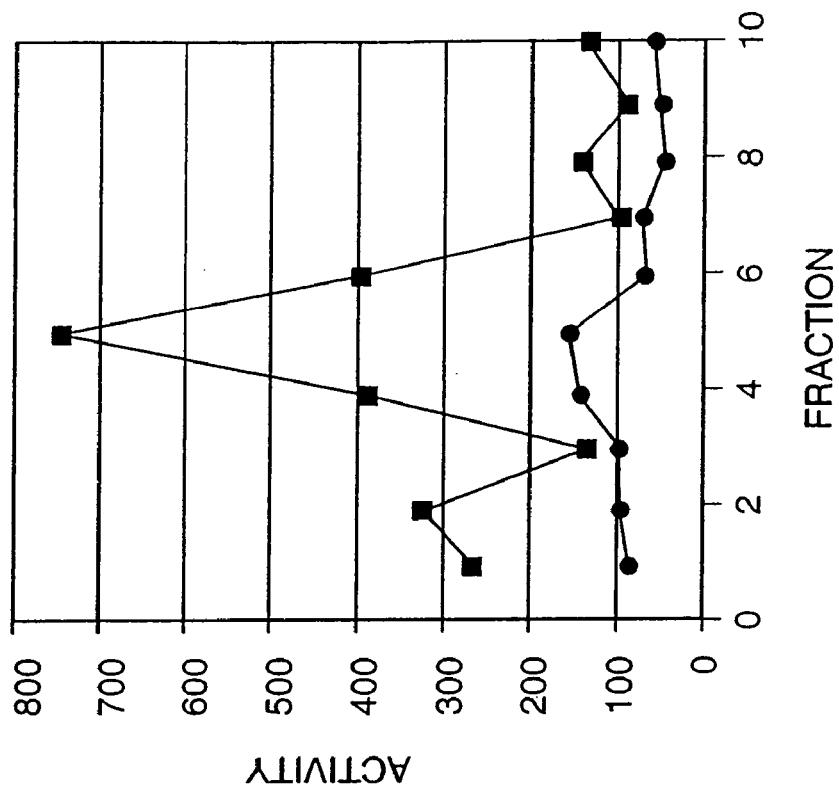
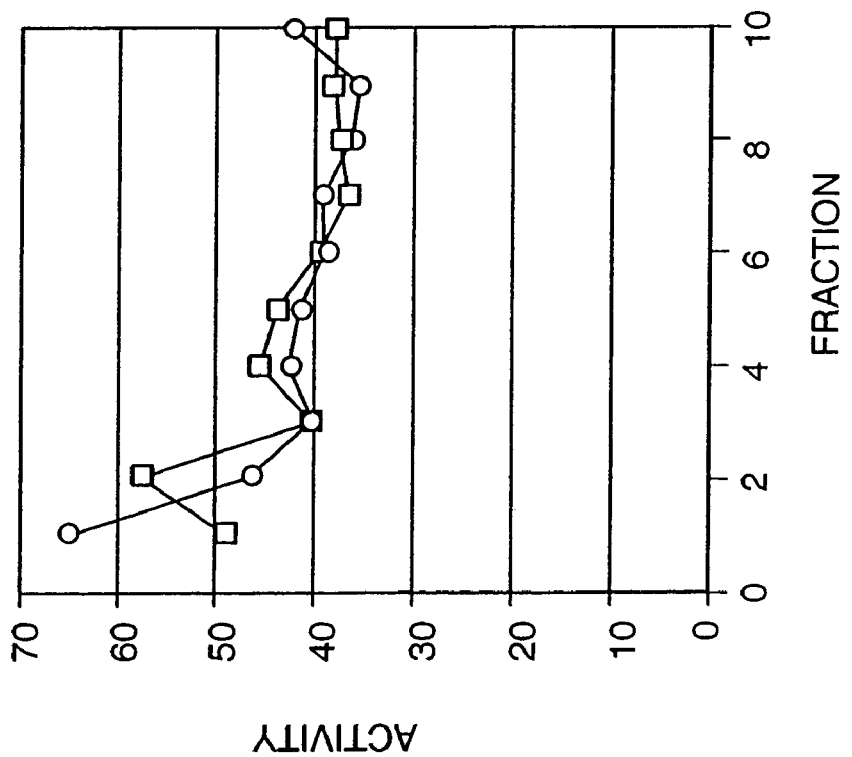

BETA-GLUCURONIDASE

BETA-GLUCURONIDASE

PTU - 300μM
IBMX - 100μM
IMP - Imipramine - 20μM

METHODS AND COMPOSITIONS THAT AFFECT MELANOGENESIS

CROSS-REFERENCE TO RELATED APPLICATIONS

This application is a divisional of U.S. application Ser. No. 10/758,335 filed Jan. 15, 2004, which is a divisional of U.S. application Ser. No. 09/827,428 filed Apr. 6, 2001, which is a continuation-in-part of U.S. application Ser. No. 09/599,487, filed Jun. 23, 2000, which claims priority from U.S. Provisional Application Ser. No. 60/141,563, filed Jun. 29, 1999, all of which are incorporated herein by reference in their entirety.

STATEMENT REGARDING FEDERALLY SPONSORED RESEARCH

This invention was made with government support under grant number EY10223 awarded by the U.S. Public Health Service. The government has certain rights in the invention.

BACKGROUND OF THE INVENTION

1. Field of the Invention

The invention relates to the fields of medicine and cell biology. More specifically, the invention relates to the fields of drug discovery and dermatology, particularly the biology of skin pigmentation.

2. Description of Related Art

Melanin is a dark pigment found in plants and animals that protects against ultraviolet radiation and provides decoration in the skin, eyes, hair, and fur of animals (reviewed in Riley, P. A., 1997, *Int. J. Biochem. Cell Biol.* 11:1235-39). There are two different types of melanin: brown/black eumelanin and yellow/red pheomelanin. Melanocytes are cells of the epidermis specialized to produce melanin. A sophisticated intercellular signaling system determines whether an individual melanocyte will produce eumelanin or pheomelanin (reviewed in Brilliant, M. H. and Barsh, G. S., 1998, in *The Pigmentary System: Physiology and Pathophysiology*, 217-29, Oxford University, New York (Nordlund, J. J. et al., eds)).

Melanocytes synthesize melanin inside of specialized organelles called melanosomes (reviewed in Orlow, S. J., 1998, in *The Pigmentary System: Physiology and Pathophysiology*, 97-106, Oxford University, New York (Nordlund, J. J. et al., eds)). Melanosomes are formed by the fusion of two types of vesicles. One type of vesicle, called a premelanosome, apparently derives directly from either the smooth endoplasmic reticulum or the trans-Golgi network. The other type of vesicle derives from the trans-Golgi network. Each of these types of vesicles contributes proteins to the melanosome necessary for its function.

Defects in the production of melanin result in pigmentation deficiencies such as albinism. Genetic analysis of abnormally pigmented strains of mice has identified more than 60 genes necessary for the normal production of melanin (reviewed in Silvers, W. K., 1979, *The Coat Colors of Mice: A Model for Mammalian Gene Action and Interaction*, Springer-Verlag, Basel). One of these genes encodes the enzyme tyrosinase. Tyrosinase protein is a multi-functional enzyme that catalyzes several steps in the production of melanin; tyrosinase activities include the rate-limiting steps of converting tyrosine to dihydroxyphenylalanine (DOPA), and DOPA to dopaquinone (reviewed in Lerner, A. B., and Fitzpatrick, T. B., 1950, *Physiol. Rev.* 30:91-126), as well as the oxidation of 5,6-dihydroxyindole to 5,6-indolequinone (Korner and Pawelek, 1982, *Science* 217:1163-1165). Both humans and mice lacking tyrosinase activity suffer a severe form of albinism.

Two tyrosinase-related proteins (TRP-1, encoded by the mouse brown gene, and TRP-2, encoded by the mouse slaty gene) also are important for melanogenesis (reviewed in Hearing, V. J., 1993, *Am. J. Hum. Genet.* 52:1-7). Each of the TRP proteins shares about 40% sequence identity with tyrosinase and with each other. Each of these three enzymes (tyrosinase, TRP-1 and TRP-2) is predicted to contain one transmembrane domain. Together, they form a high molecular weight complex associated with the melanosomal membrane (Orlow, S. J., et al., 1994, *J. Invest. Dermatol.* 103:196-201).

Another protein that is important for the production of melanin is the P protein. In mice, it is the product of the pink-eye dilution (p) gene. In humans, it is the product of the P gene. p-null mice produce significantly less melanin than wild-type mice (Silvers, supra). A wild-type human P gene, but not a mutant human P gene, can complement the hypopigmented phenotype of p-null mouse melanocytes (Sviderskaya, E. V., et al., 1997, *J. Invest. Dermatol.* 108:30-34). P protein is apparently needed for the production of eumelanin, but not of pheomelanin (Lamoreux, M. L., et al., 1995, *Pigment. Cell. Res.* 8:263-70).

Tyrosinase positive oculocutaneous albinism (Ty-pos OCA) or type 2 oculocutaneous albinism (OCA2) is the most common form of albinism worldwide. It results from mutations at the pink-eyed dilution gene (P) (King, R A. et al. (1995) Scriver, C R. et al. (eds) *The Metabolic Basis of Inherited Disease*, McGraw-Hill, New York. pp 4353-4392; Ramsay, M. et al. (1992) *Am. J. Hum. Genet.* 51:879-84; Rinchik, E M. et al. (1993) *Nature* 361: 72-76). Affected individuals have hypopigmented skin, hair and eyes (Manga P. et al. (1999) *J. Dermatol.* 26:738-47), and are thus at increased risk of developing UV-induced carcinomas (Kromberg, J G. et al. (1989) *Clin. Genet.* 36:43-52).

The p gene product (p), is predicted to have 12 transmembrane domains (Gardner, J M. et al. (1992) *Science* 257:1121-1124; Rinchik, E M. et al. (1993) *Nature* 361:72-76), and is present in melanocytes, the site of melanin synthesis (Rosemblat, S. et al. (1994) *Proc. Natl. Acad. Sci. (USA)* 91:12071-12075). While p appears to be involved exclusively in eumelanin synthesis (Russell, E S. (1949) *Genetics* 34:146-166), a precise function is yet to be assigned to the gene.

Several authors have suggested that P protein acts as a tyrosine transporter by pumping tyrosine into the melanosome where it is converted into melanin by tyrosinase activity (see, e.g., Rinchik, E. M., et al, 1993, *Nature* 361:72-76). First, the P protein bears some resemblance to transport proteins found in prokaryotes. Second, cultured p-null mutant mouse melanocytes, which produce much less melanin than cultured wild-type mouse melanocytes, make increased levels of melanin when high concentrations of tyrosine are added to the cells growth medium (Sviderskaya, E. V., et al., supra; Rosemblat, S. et al., 1998, *Exp. Cell Res.* 239:344-52). However, contradicting this suggestion, it has been found that tyrosine uptake by melanosomes is virtually the same in p-null and wild-type melanocytes (Gahl, W. A. et al., 1995, *Pigment. Cell. Res.* 8:229-233). This observation has led other authors to hypothesize that P protein is necessary for the transport into melanosomes of some other small molecule necessary for melanogenesis (summarized in Brilliant, M. H. and Barsh, G. S., 1998, supra).

Other authors have speculated that P protein plays a structural role in melanosomes (Lamoreux, M. L, et al., supra). The integrity of melanosomes is compromised in cells lacking P protein. Tyrosinase activity, and therefore melanin production, is greatly decreased in these defective melanosomes. Specifically, tyrosinase activity levels in melanocyte extracts of skin and eyes from p-null mice are lower than such extracts from wild-type mice (Lamoreux, M. L., et al., supra Chiu, E., et al, 1993, *Exp. Eye Res.* 57:301-05). Moreover, levels of tyrosinase, TRP-1 and TRP-2 proteins are lower in p-null tissue extracts than in wild-type extracts (Rosemblat, S. et al., 1998, supra). Additionally, a much greater percentage of tyrosinase, TRP-1, and TRP-2 proteins are found in their monomeric forms, rather than as part of a high molecular weight complex, in p-null tissue extracts than in wild-type extracts (Lamoreux, M. L., et al., supra; Chiu, E., et al., supra), and tyrosinase, TRP-1, and TRP-2 are all rapidly degraded in the ocular tissue of p-null mice (Chiu, E., et al., supra). Finally, several authors have observed that melanosomes in p-null tissues and cultured melanocytes are abnormal (Russell, E. S., 1949, *Genetics* 34:146-66; Rosemblat, S. et al., 1998, supra). In p-mutant melanocytes from mouse eye, very few melanosomes are observed (Orlow, S. J. and Brilliant, M. H., 1999, *Exp. Eye Res.* 68:147-54). In cultured mutant melanocytes, a greater than normal number of melanosomes is present, but they are smaller than those seen in wild-type melanocytes (Rosemblat, S. et al., 1998, supra).

Thus, although P protein is known to be critical for the production of normal amounts of melanin in the skin, hair and eyes, the function of the P protein in this process has remained elusive. Instead, researchers have looked to other molecular targets for inhibition studies. For example, tyrosinase's well-characterized enzymatic activity, amenability to biochemical analysis, and pivotal role in melanogenesis have made it an inviting target for inhibition studies (see, e.g., Tasaka, K, et al., 1998, *Meth. Find. Exp. Clin. Pharmacol.* 20:99-109; Iida, K, et al., 1995, *Planta Med.* 61:425-28; Reish, O., et al., 1995, *Am. J. Hum. Genet* 57:127-32; Shirota, S., et al, 1994, *Biol. Pharm. Bull.* 17:266-69; Kameyama, K., et al., 1989, *Differentiation* 42:28-36). Researchers have also focused on the effects of intercellular signaling molecules on melanogenesis (see, e.g., Furumura, M. et al., 1998, *Proc. Natl. Acad. Sci. (USA)* 95:737478; Sakai, C., et al., 1997, *EMBO J.* 16:3544-52; McLeod, S. D. et al., 1995, *J. Endocrinol.* 146:439-47).

Pigmentation disorders of mammals and *Drosophila* are known and in some cases have been linked to specific defects in proteins involved in intracellular protein trafficking (Spritz (1999) *Trends Genet* 15:337-340). For example, the hypopigmentation associated with Hermansky-Pudlak syndrome (HPS) appears to be related to the regulation of protein trafficking by the AP3 protein. (Dell'Angelica et al. (1999) *Mol. Cell* 3:11-21).

For many individuals of all ages, the inappropriate production or overproduction of melanin is a cosmetic problem. By way of example, many children develop freckles after exposure to the sun, and for individuals in middle or advanced age, chloasma, freckles, and pigmentary deposits after sunburn tend to occur or increase in frequency. In addition, these pigment deposits do not disappear quickly and are more likely to become permanent with advancing age.

A number of products have been developed to effect a decrease in skin pigmentation. One such product contains hydroquinone, a well known active substance for skin de-pigmentation (e.g., see U.S. Pat. No. 6,139,854). However, hydroquinone can have serious side effects if applied over a long period of time. For example, the application of hydroquinone to skin may lead to permanent de-pigmentation, and thus to increased photosensitivity of the skin when exposed to ultraviolet light. For that reason, in some countries hydroquinone is only allowed to be used for skin de-pigmentation in limited concentrations, and, in other countries, the product is banned completely for this application.

A variety of other substances have been proposed for the control or inhibition of skin pigmentation. Almost all of these substances work by either bleaching existing pigment or preventing new pigment synthesis by inhibiting the activity of tyrosinase, the principle rate-limiting enzyme in the production of melanin. For example, U.S. Pat. No. 6,123,959 describes the use of aqueous compositions comprising liposomes and at least one competitive inhibitor of an enzyme for the synthesis of melanin in combination with at least one non-competitive inhibitor of an enzyme for the synthesis of melanin. U.S. Pat. No. 6,132,740 describes the use of certain resorcinol derivatives as skin lightening agents. WO 99/64025A1 describes compositions for skin lightening which contain tyrosinase inhibiting extracts from dicotyledonous plant species indigenous to Canada. U.S. Pat. No. 5,580,549 describes an external preparation for skin lightening comprising 2-hydroxybenzoic acid derivatives and salts thereof as inhibitors of tyrosinase. WO 99/09011A1 describes an agent for inhibiting skin erythema and/or skin pigmentation, containing at least one carbostyril derivative and salts thereof. U.S. Pat. Nos. 5,214,028 and 5,389,611 describes lactoferrin hydrolyzates for use as a tyrosinase inhibitory agents.

Despite the development of these and other compositions to lighten skin, there remains a need in the art for the development of less toxic, safer alternatives to skin bleaching and more effective and efficient methods of inhibiting melanin production. The need for new and improved methods for lightening skin is evident in view of the cosmetic industry's estimate that the market for skin lighteners worldwide exceeds well over one billion dollars a year. Thus, there is a continuing need for the development of improved agents that limit or inhibit pigmentation in the skin.

SUMMARY OF THE INVENTION

The present invention provides novel screens for the identification of compounds that inhibit or increase melanogenesis in melanogenic cells. The development of these assays is based, in part, on the discovery that some compounds that inhibit melanogenesis do so by causing a mislocalization of tyrosinase, the key enzyme in melanin synthesis.

The P protein is a pivotal target for compounds and drugs to decrease or increase pigmentation of the skin, hair and/or eyes. Accordingly, in one aspect, the present invention provides, for the first time, screens for compounds that inhibit or enhance P protein function based, in part, on the discovery that P protein function is required for proper cellular localization of tyrosinase and other melanosomal proteins and is required for both full tyrosinase activity and melanogenesis in melanogenic cell types such as, for example, melanocytes and melanoma cells.

Wild-type melanogenic cells target tyrosinase primarily to melanosomes. Some tyrosinase is also secreted by these cells. P protein-compromised melanogenic cells mislocalize tyrosinase. They secrete significantly more tyrosinase than wild-type melanogenic cells, and also contain tyrosinase in non-melanosomal vesicles. Tyrosinase that is secreted from melanogenic cells, regardless of whether the cells have normal or inhibited P protein function, is enzymatically active in the growth or incubation medium, where it can convert tyrosine into melanin.

In one aspect, the present invention provides a method of screening for compounds that inhibit melanogenesis in melanogenic cells, comprising incubating these cells in medium containing a compound to be tested, and identifying compounds that cause a change in the cellular localization of tyrosinase in these cells. Mislocalization of tyrosinase can indicate inhibition of melanogenesis.

In a still further aspect, the present invention provides methods of screening for compounds that increase melanogenesis in melanogenic cells, comprising incubating melanogenic cells in medium containing a compound to be tested, and identifying compounds that cause a decrease in the amount of tyrosinase secreted by the cells relative to the amount of tyrosinase retained by the cell, wherein such relative decrease in the amount of tyrosinase secreted indicates that the compound is a candidate for a compound that increases melanogenesis.

Another aspect of the invention is based, in part, on the discovery that non-melanogenic cells can be made to produce active tyrosinase by transfecting them with a heterologous tyrosinase-encoding gene. The tyrosinase activity of these cells is dramatically increased by cotransfection with a heterologous P protein-encoding gene. Maximal tyrosinase activity in these cells is, therefore, dependent upon P protein function. When cells expressing both heterologous tyrosinase and heterologous P protein are treated with drugs that inhibit P protein function such as, for example, imipramine, the tyrosinase activity of these cells is reduced to that of cells expressing heterologous tyrosinase alone. Imipramine and other drugs that inhibit P protein function do not otherwise affect tyrosinase activity in cells that express heterologous tyrosinase but that do not express heterologous P protein.

Accordingly, in a further aspect, the present invention provides methods of screening for compounds that affect (e.g., either inhibit or increase) P protein function in cells that do not ordinarily express tyrosinase and/or P protein, comprising manipulating these cells so that they express both tyrosinase and P protein, and treating the cells with a compound to be tested. The tyrosinase activity of these cells is measured. Compounds that affect (e.g., inhibit or increase) the tyrosinase activity of these cells, but that do not affect the tyrosinase activity of cells expressing tyrosinase alone, are identified as compounds that affect tyrosinase in a P protein dependent manner.

In a further aspect, the present invention provides methods for modeling chemical compounds known to affect or mimic the function of P protein. Analogs of the modeled compound are selected or designed, and screened for the ability to affect or mimic P protein function. By using analogs of a compound known to affect or mimic P protein function, new and better compounds that affect or mimic P protein function can be discovered using the methods of the present invention.

In a still further aspect, the present invention provides methods for using, in medicinal and cosmetic compositions, compounds that affect or mimic the function of P protein, thereby treating a disease, condition, or disorder involving the production (underproduction or overproduction) of melanin.

The inventors have also determined that agents capable of modifying late endosomal/lysosomal transport modify pigmentation by altering the trafficking of tyrosinase and other proteins necessary for melanin synthesis. This discovery has been utilized to provide other aspects of the present invention, which include methods and pharmaceutical compositions comprising agents that modify late endosomal/lysosomal trafficking. These methods and pharmaceutical compositions are useful for decreasing and/or inhibiting melanin production and, therefore, decreasing, lowering or preventing the formation of skin pigmentation.

The invention thus further provides, in another aspect, a method of decreasing, lowering or preventing melanin production in a melanocyte, comprising contacting the melanocyte with a pharmaceutically effective amount of a compound that effects an alteration in late endosomal/lysosomal trafficking in the melanocyte wherein the alteration in late endosomal/lysosomal trafficking results in a decrease in melanin production in the melanocyte. In a certain embodiment, the alteration in late endosomal/lysosomal trafficking is effected by contacting the melanocyte with a compound that is an antagonist of late endosomal/lysosomal trafficking. In another certain embodiment, the alteration in late endosomal/lysosomal trafficking is an alteration in late endosomal/lysosomal cholesterol trafficking.

In certain embodiments, an alteration in late endosomal/lysosomal trafficking is effected by contacting the melanocyte with a compound selected from the group consisting of progesterone, a hydrophobic amine, sphingosine, and a compound of the formula

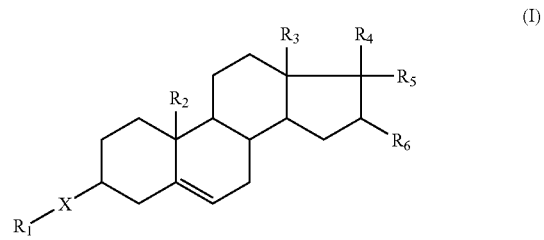

(I)

wherein X is O or S. In a preferred embodiment, X is O.

$R_1$ is —C(O)($C_1$-$C_6$)alkyl or —($CH_2$)$_n$—O—($C_1$-$C_6$) alkyl, or —($CH_2$)$_n$—$NR_7R_8$ where n is 0-3, where each of $R_7$ and $R_8$ are independently selected from H and ($C_1$-$C_6$)alkyl. Preferably, each of $R_7$ and $R_8$ are independently selected from —C(O)($C_1$-$C_3$)alkyl, —$CH_2$—O—($C_1$-$C_3$)alkyl, or —($CH_2$)$_2$—N($C_1$-$C_3$ alkyl)$_2$. More preferably, each of $R_7$ and $R_8$ is independently selected from —C(O)$CH_3$, —$CH_2$—O—$CH_3$, or —($CH_2$)$_2$—N($CH_3$)$_2$.

$R_2$ is H or ($C_1$-$C_6$)alkyl. In some embodiments, $R_2$ is ($C_1$-$C_3$)alkyl. In preferred embodiments, $R_2$ is —$CH_3$.

$R_3$ is H or ($C_1$-$C_6$)alkyl. In preferred embodiments, $R_3$ is ($C_1$-$C_3$)alkyl. In more preferred embodiments, $R_3$ is —$CH_3$.

$R_4$ is —C(O)($C_1$-$C_6$)alkyl. Preferably, $R_4$ is —C(O)($C_1$-$C_3$)alkyl. In more preferred embodiments, $R_4$ is —C(O)$CH_3$ or —C(O)$CH_2CH_3$.

$R_5$ is H or —($C_1$-$C_6$)alkyl. Preferably, $R_5$ is H or —$CH_3$. In another embodiment, $R_4$ and $R_5$ taken together are =O.

$R_6$ is H or —($C_1$-$C_6$)alkyl or —($CH_2$)$_n$—$NR_9R_{10}$, where each of $R_9$ and $R_{10}$ are independently selected from H and ($C_1$-$C_6$)alkyl. Preferably, $R_6$ is H or —$CH_3$, or —$CH_2CH_3$ or —$CH_2NH_2$. In another embodiment, $R_5$ and $R_6$ are combined with the carbon atoms to which they are attached to form a $C_5$-$C_8$ carbocyclic ring, and preferably a $C_6$ carbocyclic ring, which can be substituted by one to three of halogen, OH, —($C_1$-$C_6$)alkyl, —($C_1$-$C_6$)alkoxy, amino, =O, ($C_1$-$C_6$)alkylamino, di-(($C_1$-$C_6$)alkyl)amino, trifluoromethyl, or —$OCF_3$, which substituents can be substituted anywhere on the carbocyclic ring where it is possible to make such substitutions.

In certain embodiments, the compound is progesterone. In other embodiments, the compound is a hydrophobic amine. In particular embodiments, the hydrophobic amine is selected from the group consisting of a phenothiazine and a tricyclic antidepressant. In other embodiments, the compound is a phenothiazine. In certain embodiments of the invention, the phenothiazine is selected from the group consisting of trifluoperazine, chlorpromazine, prochlorperazine, triflupromazine, promazine, thioridazine, mesoridaine, piperacetazine, perphenazine, fluphenazine, acetophenazine, and thiethylperazine. In yet other embodiments, the compound is a tricyclic antidepressant. In certain embodiments, the tricyclic antidepressant is selected from the group consisting of imipramine, nortriptyline, protriptyline, trimipramine, and doxepin. In other particular embodiments, the compound is sphingosine. In another embodiment, the tricyclic antidepressant is not imipramine.

In still other embodiments, the compound is an antagonist of a late endosomal/lysosomal trafficking protein. In certain embodiments, the compound is of the formula

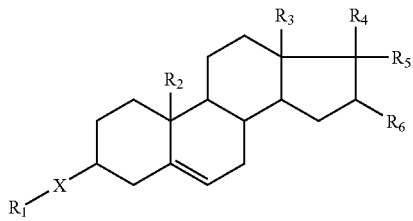
(I)

wherein the X and $R_1$-$R_6$ groups are as defined above. In a preferred embodiment, the compound is selected from the group consisting of:

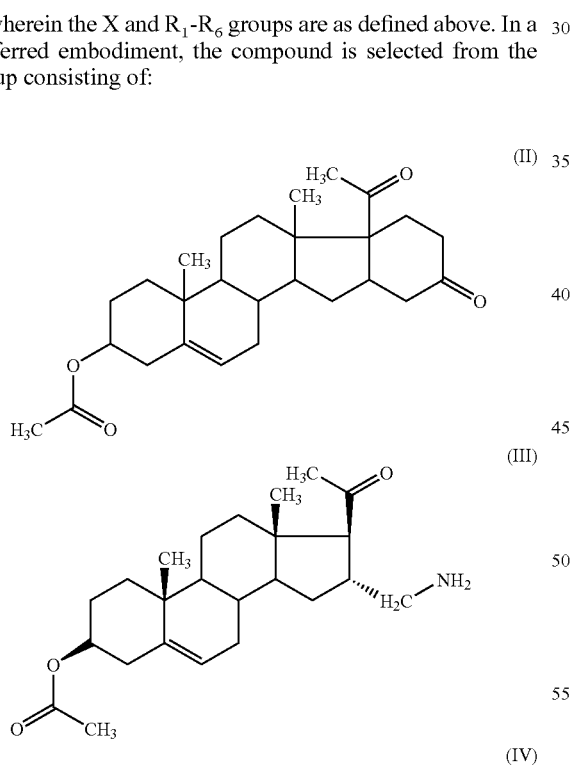
(II)

(III)

(IV)

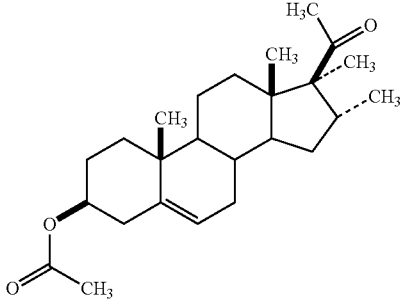
(V)

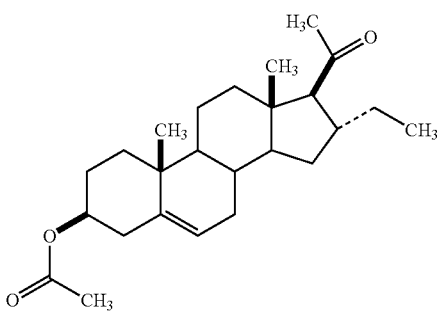
(VI)

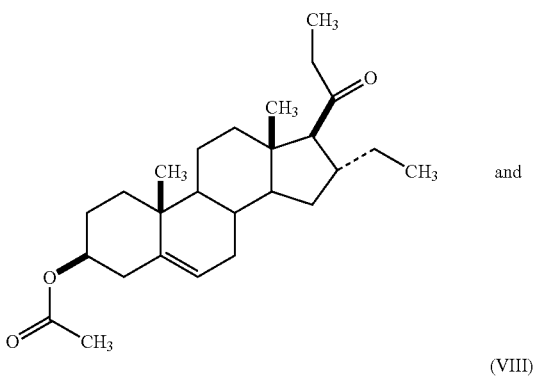
(VII)

and (VIII)

and any pharmaceutically acceptable salts or solvates thereof.

In another aspect, the invention provides a method of reducing skin pigmentation. In this method the skin of a patient in need of said treatment is contacted with a pharmaceutically effective amount of a compound that effects an alteration in late endosomal/lysosomal trafficking, wherein such an alteration results in a reduction of skin pigmentation. In a certain embodiment, the alteration in late endosomal/lysosomal trafficking is effected by contacting the skin with a compound that is an antagonist of late endosomal/lysosomal trafficking. In another certain embodiment, the alteration in late endosomal/lysosomal trafficking is an alteration in late endosomal/lysosomal cholesterol trafficking.

In certain embodiments, an alteration in late endosomal/lysosomal trafficking is effected by contacting the skin with a pharmaceutically effective amount of a compound selected from the group consisting of progesterone, a hydrophobic amine, sphingosine, and a compound of any of the formulae (I) through (VIII) as defined above, or a pharmaceutically acceptable salt or solvate thereof.

In certain embodiments, the compound is progesterone. In other embodiments, the compound is a hydrophobic amine. In particular embodiments, the hydrophobic amine is selected from the group consisting of a phenothiazine and a tricyclic antidepressant. In other embodiments, the compound is a phenothiazine. In particular embodiments, the phenothiazine is selected from the group consisting of trifluoperazine, chlorpromazine, prochlorperazine, triflupromazine, promazine, thioridazine, mesoridaine, piperacetazine, perphenazine, fluphenazine, acetophenazine, and thiethylperazine. In yet other embodiments, the compound is a tricyclic antidepressant. In certain embodiments, the tricyclic antidepressant is selected from the group consisting of imipramine, nortriptyline, protriptyline, trimipramine, and doxepin. In another embodiment, the tricyclic antidepressant is not imipramine. In some particular embodiments, the compound is sphingosine. In certain embodiments, the compound is an antagonist of a late endosomal/lysosomal trafficking protein. In certain embodiments, the compound has the formula of any of (I) through (VIII) as defined above, or a pharmaceutically acceptable salt or solvate thereof.

In yet another aspect, the invention provides a pharmaceutical composition for reducing skin pigmentation. This composition comprises a pharmaceutically effective amount of a compound that effects an alteration in late endosomal/lysosomal trafficking in a skin cell, and further comprises a pharmaceutically acceptable carrier. In a certain embodiment, the alteration in late endosomal/lysosomal trafficking is effected by contacting the melanocyte with a compound that is an antagonist of late endosomal/lysosomal trafficking. In another certain embodiment, the alteration in late endosomal/lysosomal trafficking is an alteration in late endosomal/lysosomal cholesterol trafficking. The pharmaceutical composition is preferably adapted for topical administration.

In certain embodiments, the compound that effects an alteration in late endosomal/lysosomal trafficking is selected from the group consisting of progesterone, a hydrophobic amine, sphingosine, and a compound of any of formulae (I) through (VIII) as defined above, or a pharmaceutically acceptable salt or solvate thereof.

In certain embodiments, the compound is progesterone. In other embodiments, the compound is a hydrophobic amine. In particular embodiments, the hydrophobic amine is selected from the group consisting of a phenothiazine and a tricyclic antidepressant. In some embodiments, the compound is a phenothiazine. In certain embodiments, the phenothiazine is selected from the group consisting of trifluoperazine, chlorpromazine, prochlorperazine, triflupromazine, promazine, thioridazine, mesoridaine, piperacetazine, perphenazine, fluphenazine, acetophenazine, and thiethylperazine. In other embodiments, the compound is a tricyclic antidepressant. In particular embodiments, the tricyclic antidepressant is selected from the group consisting of imipramine, nortriptyline, protriptyline, trimipramine, and doxepin. In another embodiment the tricyclic antidepressant is not imipramine. In other embodiments, the compound is sphingosine. In certain embodiments, the compound is an antagonist of a late endosomal/lysosomal trafficking protein. In certain embodiments, the compound has the structure of any of formulae (I) through (VIII) as defined above, or a pharmaceutically acceptable salt or solvate thereof.

In another aspect, the invention provides a method of activating melanogenesis. The method comprises contacting a melanocyte with diminished or absent P protein activity with a pharmaceutically effective amount of a compound that inhibits ATPases, whereby the inhibition of ATPases results in an activation of melanogenesis in the melanocyte. In a certain embodiment, the melanocyte with diminished or absent P protein activity is contacted with a pharmaceutically effective amount of a compound selected from the group consisting of bafilomycin, concanamycin, and derivatives thereof. In a preferred embodiment, the melanocyte with diminished or absent P protein activity is contacted with a pharmaceutically effective amount of bafilomycin, or a derivative thereof. In another preferred embodiment, the melanocyte with diminished or absent P protein activity is contacted with a pharmaceutically effective amount of concanamycin, or a derivative thereof.

In another aspect, the invention provides a method of treating tyrosinase-positive, oculocutaneous albinism in an individual. The method comprises contacting skin of the individual with a pharmaceutically effective amount of a compound that inhibits ATPases, whereby the inhibition of ATPases results in an activation of melanogenesis in the tyrosinase-positive, oculocutaneous albinistic individual. In a certain embodiment, the skin of the individual is contacted with a pharmaceutically effective amount of a compound selected from the group consisting of bafilomycin, or a derivative thereof, and concanamycin, or a derivative thereof. In a preferred embodiment, the skin of the individual is contacted with a pharmaceutically effective amount of bafilomycin, or a derivative thereof. In another preferred embodiment, the skin of the individual is contacted with a pharmaceutically effective amount of concanamycin, or a derivative thereof.

In another aspect, the present invention further provides a kit comprising a container comprising a pharmaceutical composition of the present invention as described above. The kit may further comprise a package insert comprising printed instructions directing the use of the pharmaceutical composition for modulating skin pigmentation, e.g., for either lightening or darkening the skin, as appropriate to the particular pharmaceutical composition.

BRIEF DESCRIPTION OF THE FIGURES

In FIG. 2A (left), tyrosine hydroxylase activity of melan-a cell extracts is measured in cpm [$^3$H]H$_2$O/60 micrograms protein/hr. In FIG. 2B (right), tyrosine hydroxylase activity in media from melan-a cells is measured in cpm [3H]H$_2$O/hr normalized to the amount of cell extract protein. The tyrosine hydroxylase activity of extracts from melan-a cells incubated with benztropine (column 2 in FIG. 2A.) and nitroquipazine (column 4 in FIG. 2A) is higher than that seen in untreated cells. The extracts from cells treated with imipramine (column 3 in FIG. 2A) show a reduced activity. The effects of the drugs on the enzyme activity of the cell extracts is not reflected in the activity of the enzyme secreted into the media. While benztropine has little effect on activity (column 2 in FIG. 2B), imipramine (column 3 in FIG. 2B) and nitroquipazine (column 4 in FIG. 2B) cause a significant increase in activity in the media.

FIG. 8A=small granule fractions. FIG. 8B=large granule fractions.

FIGS. 9A and 9B are graphic presentations demonstrating β-galactosidase targeting in melan-A and melan-P cells. β-galactosidase activity was measured in fractionated membranes from melan-a (squares) and melan-p cells (circles) as described below in Example 5. FIG. 9A=small granule fractions. FIG. 9B=large granule fractions.

FIGS. 10A and 10B are graphic presentations demonstrating β-hexosaminidase targeting in melan-A and melan-P cells. β-hexosaminidase activity was measured in fractionated membranes from melan-a (squares) and melan-p cells (circles) as described below in Example 5. FIG. 10A=small granule fractions. FIG. 10B=large granule fractions.

FIGS. 11A and 11B are graphic presentations demonstrating β-glucosidase targeting in melan-A and melan-P cells. β-glucosidase activity was measured in fractionated membranes from melan-a (squares) and melan-p cells (circles) as described below in Example 5. FIG. 11A=small granule fractions. FIG. 11B=large granule fractions.

FIG. 12A=small granule fractions. FIG. 12B=large granule fractions.

DETAILED DESCRIPTION OF THE INVENTION

Figure 1:
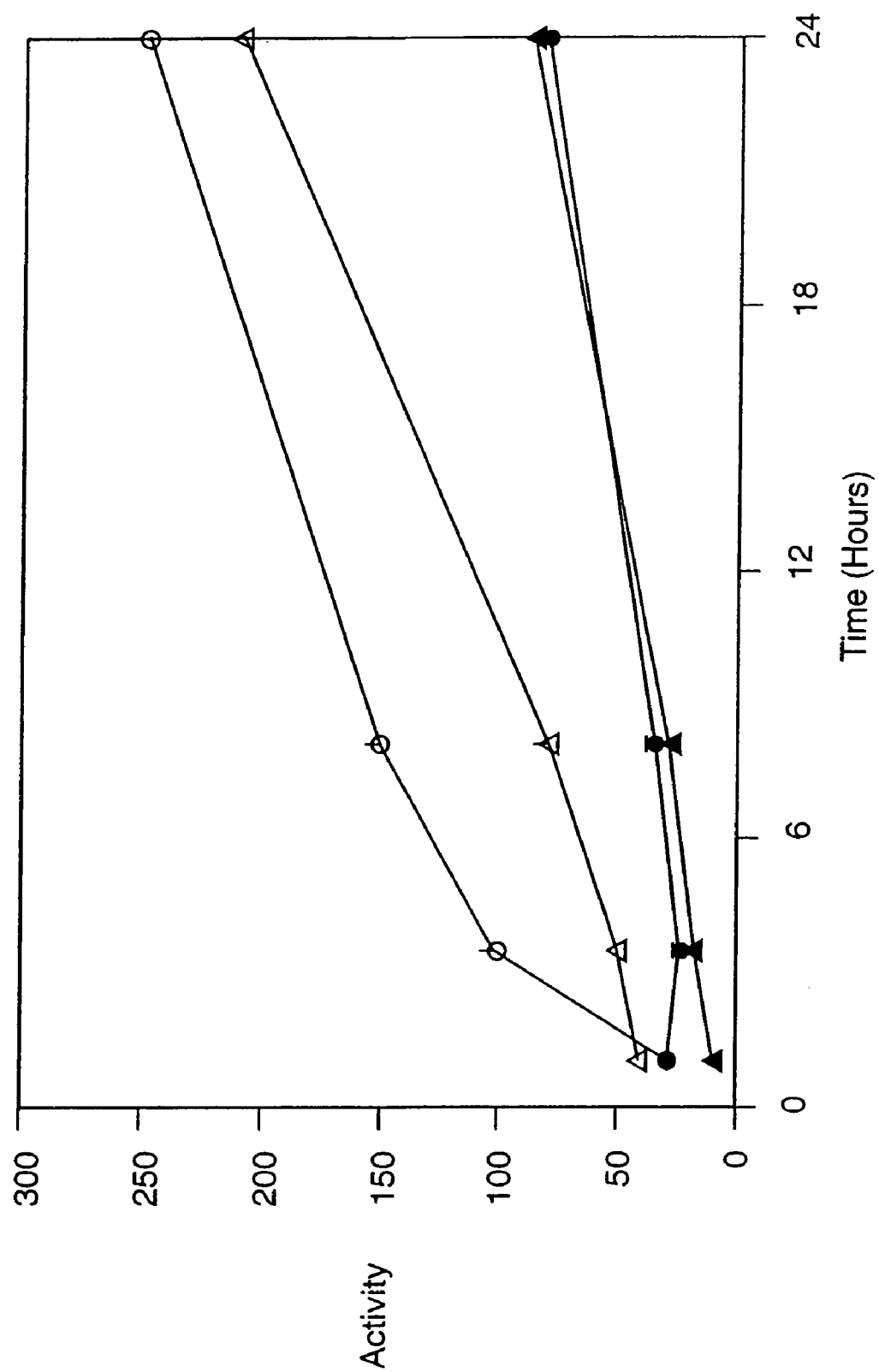
FIG. 1 is a graphic presentation of tyrosinase activity in media from cultured melanocytes. Melan-a melanocytes cultured from black mice, and melan-p melanocytes cultured from mice lacking a P gene transcript, were separately cultured in DMEM containing low (0.03 mM) or high (0.3 mM) tyrosine for the indicated time period. The activity of tyrosinase was determined at specific time intervals in media from melanocytes. The medium was dialyzed prior to determining the enzyme activity, which is expressed as cpm of tritiated water generated per hour. ▲ Melan-a, high tyrosine; • melan-a, low tyrosine; Δ melan-p1, high tyrosine; ○ melan-p1, low tyrosine. Increasing tyrosinase activity in the media removed from melan-p cells, which have no P protein transcripts, grown in the presence of 0.03 mM tyrosine, reflects an increased secretion of tyrosinase by these cells. In contrast, melan-a cells, which represent wild-type melanocytes, secrete significantly less tyrosinase into the media. Growing melan-p cells in the presence of high tyrosine partially alleviated the P-deficient phenotype.

The patent and scientific literature referred to herein establishes knowledge that is available to those with skill in the art. The issued patents, applications, and references that are cited herein are hereby incorporated by reference to the same extent as if each was specifically and individually indicated to be incorporated by reference.

The invention is based, in part, on the discovery that compounds that cause melanogenic cells to mislocalize tyrosinase (e.g., to increase the amount of tyrosinase secreted or the amount of tyrosinase found in non-melanosomal vesicles) also inhibit melanogenesis. For purposes of the present invention, the term "melanogenic cells" is defined as cells that contain pigmented melanosomes (e.g., melanocyte cells and melanoma cells). Melanogenic cells can include, for example, melanogenic cells that express heterologous melanosomal proteins. For example, in preferred embodiments, the coding sequence or sequences of the P protein gene, tyrosinase gene, TRP-1 gene, and/or TRP-2 gene in a mouse melanogenic cell can be mutated or deleted, and the cell engineered to express instead the corresponding coding sequence of the human P protein gene, tyrosinase gene, TRP-1 gene, and/or TRP-2 gene.

The present invention also relates to the discovery that the P protein is necessary to correctly localize tyrosinase predominantly to the membrane of melanosomes. Yet another aspect of the present invention is based on the finding that melanocytes treated with compounds that inhibit P protein function accumulate reduced amounts of intracellular melanin, and secrete increased amounts of tyrosinase into the growth medium. Still another aspect of the present invention relates to the discovery that, in the presence of the P protein, the enzymatic activity of tyrosinase protein in cultured cells is augmented. In yet another aspect, the present invention relates to the discovery that when melanocytes are contacted with inhibitors of late endosomal/lysosomal trafficking, thereby affecting tyrosinase localization, melanogenesis is inhibited and melanin synthesis is decreased. Accordingly, the present invention provides novel methods of screening for compounds that inhibit melanogenesis. Compounds identified using the methods of the present invention are useful for treating diseases and cosmetic defects associated with the underproduction or overproduction of melanin.

Also disclosed by the present invention is the fact that wild-type melanogenic cells with normal P protein function secrete some tyrosinase, and that compounds that increase secretion of tyrosinase in a P protein dependent manner also inhibit melanogenesis. Accordingly, the present invention provides novel methods of screening for compounds that increase melanogenesis by increasing the function of P protein. For purposes of this application, compounds that increase the function of P protein and compounds that decrease the function of P protein are collectively referred to herein as "compounds that affect the function of P protein." Still another aspect of the invention is a method of screening for compounds that increase melanogenesis by mimicking the function of P protein. For purposes of the invention, ?compounds that mimic the function of P protein? are compounds that are not P proteins, yet when they are administered to, or incubated with, melanogenic cells that do not contain P protein, they serve to restore at least in part the correct targeting of tyrosinase to the melanogenic membrane. Melanogenic cells that do not contain P protein may be cells that do not express P protein transcripts (such as melan-p cells, described herein) or melanogenic cells that do not express a functional P protein gene product.

It has also been determined that the inhibition of late endosomal/lysosomal trafficking in melanocytes results in a decrease or inhibition of melanogenesis, and the subsequent decrease in the amount of melanin in melanocytes results in a reduction in skin pigmentation. Thus, compounds that inhibit late endosomal/lysosomal trafficking have the affect of decreasing or inhibiting melanogenesis and reducing pigmentation in melanocytes and skin tissue.

The present invention also relates to the discovery that the inhibition of ATPases in melanocytes results in activation of melanogenesis. Thus, compounds that inhibit ATPases have the affect of activating melanogenesis and increasing the amount of melanin in melanocytes and skin tissue. This discovery is exploited for the treatment of tyrosinase positive oculocutaneous albinism to effect an increase in pigmentation.

Non-limiting examples of compounds or agents useful in the compositions and methods of the present invention include compounds that affect P protein function, e.g., imipramine; compounds that affect late endosomal/lysosomal trafficking, e.g., progesterone; hydrophobic amines; sphingosine; compounds that are in the same class or are derived from the compound U18666A; and compounds that inhibit ATPase activity, e.g., bafilomycin and concanamycin.

1 Methods of Screening for Inhibitors or Inducers of Melanogenesis 1.1 Methods of Screening for Inhibitors of Melanogenesis Using Melanogenic Cells In order for melanogenic cells to engage in robust melanogenesis, they must target their tyrosinase predominantly to the melanosomal membrane. Consequently, in one aspect, the methods of the present invention entail screening for compounds that cause melanogenic cells to mislocalize tyrosinase. P protein function is necessary for the correct cellular localization of tyrosinase.

Therefore, in another aspect, the methods of the present invention entail screening for compounds that inhibit P protein function, thereby causing melanogenic cells to mislocalize tyrosinase. Such methods are based, in part, on the discovery that cultured melanocytes that have been genetically altered to eliminate P protein function secrete significantly more tyrosinase into the growth medium than wild-type melanocytes.

Compounds such as, e.g., imipramine, that reduce or eliminate P protein function will have the desired effect. Thus, the cellular mislocalization of tyrosinase by cells treated with a test compound indicates that the test compound inhibits melanogenesis. Mislocalization of tyrosinase resulting in secretion can be detected initially by assaying either the level of tyrosinase activity in the medium or cells, or the level of tyrosinase protein in the medium or cells. Test compounds that cause an increase in secretion of tyrosinase, or a decrease in intracellular tyrosinase, are candidates for compounds that inhibit melanogenesis by inhibiting P protein function. Such candidate compounds can be further investigated for their effect on melanogenesis, and/or for their effects in both the presence and absence of P protein, as described more fully below. If the effect of the candidate compound depends upon the presence of P protein, then the compound inhibits the function of P protein.

Because growing P-protein-deficient melanocytes in the presence of high levels of tyrosine in the medium can partially rescue the P-protein-deficiency, it is preferable, but not necessary, that a screen for inhibitors of melanogenesis is carried out in the presence of low amounts of tyrosine in the media, e.g., 0.0 1-0.05 mM tyrosine, more preferably 0.014-0.03 mM tyrosme.

1.2 Methods of Screening for Inhibitors of Melanogenesis Using Assays for Tyrosinase activity Wild-type melanogenic cells grown in vitro culture will synthesize melanin inside of melanosomes as they do in vivo. In these cultured cells, tyrosinase is found predominantly in the melanosomal membrane, although some tyrosinase is also secreted. The tyrosinase that is found in the melanosomal membrane is held in place by a C-terminal transmembrane domain and has its active site disposed toward the melanosomal lumen. By contrast, in melanogenic cells inhibited for melanogenesis through either a mutation in P protein or a compound that inhibits P protein function, tyrosinase will be mislocalized. A significantly greater fraction of the cells' tyrosinase is secreted from the cells into the growth or incubation medium. Additionally, the secreted tyrosinase polypeptide will be shorter than that found in wild-type cells because it lacks its C-terminal membrane anchor. The secreted tyrosinase, however, is enzymatically active in the growth or incubation medium where it can synthesize melanin from extracellular tyrosine. Consequently, tyrosine-containing growth or incubation media from melanogenic cells that have been inhibited for melanogenesis will turn dark. The higher the concentration of tyrosine in the medium, the darker the medium becomes, and the higher the concentration of tyrosinase in the medium, the faster the medium darkens. Because melanogenic cells that are not inhibited for melanogenesis secrete significantly less tyrosinase, the tyrosine-containing growth or incubation media in which they are cultured will not become as dark.

This discovery can be used in a novel method of screening to identify compounds that inhibit or modulate melanogenesis. Melanogenic cells are grown in culture or incubated in medium containing tyrosine. The cells are treated with a test compound. If the test compound causes tyrosinase to be mislocalized and secreted from the treated cells, then tyrosine in the medium will be converted into melanin, darkening the medium. An assay is used wherein the color of the medium is compared to the color of the medium of the melanogenic cells grown or incubated under similar conditions but without the test compound (a control medium). If the medium of the cells treated with the test compound turns darker than the control medium, then the test compound is identified as candidate for a compound that inhibits melanogenesis.

More typically, in order to obtain at least semi-quantitative data, the media from the cells is first filtered, centrifuged and/or dialyzed prior to assay for tyrosinase activity. These types of treatments remove potentially confounding factors such as cells or particulate matter (e.g., melanosome or shed membranes) containing tyrosinase that could compete for substrate, and/or remove excess free tyrosine that might compete with labeled substrate. Any of a number of alternative ways of measuring tyrosinase can be carried out, such as by using any of the enzymatic tyrosinase activities including, but not limited to, converting tyrosine to dihydroxyphenylalanine (DOPA), DOPA to dopaquinone, and oxidation of 5,6-dihydroxyindole to 5,6-indolequinone. For example, when assaying for the tyrosine hydroxylase activity of tyrosinase, non-tyrosine or altered tyrosine substrates of tyrosinase can be used in addition to tyrosine. In one aspect, melanogenic cells are grown or incubated in culture with a test compound. After pretreatment of the medium, a non-tyrosine or altered tyrosine substrate of tyrosinase is added to the growth or incubation medium. The substrate can be a homolog, analog, or derivative of tyrosine which can be a natural product or produced synthetically. Tyrosinase activity in the medium converts the substrate into its product.

An assay is then used to detect the presence of the product and/or the absence of the substrate. One non-limiting assay is a calorimetric assay. In methods of screening for compounds that inhibit melanogenesis that use a calorimetric assay, a substrate is chosen that changes color when it is acted upon by tyrosinase. That is, the wavelength of light absorbed by the substrate is different than the wavelength of light absorbed by the products of the reaction catalyzed by tyrosinase. The wavelength of light absorbed by the substrate and/or by the products can be in the visible light range, the infrared range, or the ultraviolet range of the spectrum. The concentration of substrate, incubation time, and other reaction conditions can be chosen such that the speed and/or intensity of the color change is proportional to the amount of tyrosinase activity in the cells growth or incubation medium. The color change can be detected by direct observation, or measured by a device, such as a spectrophotometer and compared, e.g., to a standard curve prepared using varying amounts of product.

An example of a calorimetric assay is the DOPA oxidase assay. In one method of screening for compounds that inhibit melanogenesis using this assay, a compound to be tested for its ability to inhibit melanogenesis is added to the growth or incubation medium of melanogenic cells. After filtration, centrifugation and/or dialyzation of the medium, L-DOPA is added under conditions that would otherwise allow for tyrosinase to catalyze the formation of dopachrome from L-DOPA. In a preferred though non-limiting embodiment, the final concentration of L-DOPA in the medium is about $5 \times 10^{-3}$ M, the pH is about 7.4, and the temperature is about 25° C. Increased absorbance of the medium at 475 nm (relative to the absorbance at 475 nm of medium from similar cells grown under similar conditions but without the test compound) indicates the formation of dopachrome by tyrosinase in the medium and, therefore, the inhibition of melanogenesis by the test compound.

Alternatively, as dopachrome absorbs light within the visible range, the presence of dopachrome, and hence the inhibition of melanogenesis, can be determined by direct inspection of the reaction, without the aid of a spectrophotometer.

Another assay is a radiometric assay. In an alternative method of screening for compounds that inhibit melanogenesis using this assay, substrate is radioactively labeled and added to the growth or incubation medium to be assayed. If tyrosinase is present in the medium, it cleaves the substrate into a labeled product and an unlabeled product. The amount of radioactive substrate that has been converted into radioactive product is measured. The concentration of substrate, time of incubation, temperature of incubation, and other reaction conditions can be chosen so that the amount of radioactive product produced is proportional to the amount of tyrosinase in the growth or incubation medium being assayed. A greater amount of labeled product in the medium from cells treated with the test compound than in the medium of similar cells grown under similar conditions but without the test compound indicates that the test compound is a candidate for a compound that inhibits melanogenesis.

An example of this type of assay is the radiometric tyrosine hydroxylase assay. In this assay, the amount of $[^3H]H_2O$ released from $[^3H]$tyrosine as a result of the tyrosine hydroxylase activity of the tyrosinase enzyme is measured. In one method of screening for compounds that inhibit melanogenesis that uses this assay, media from melanogenic cells is harvested and cells removed. Additionally, the media can be dialyzed before assay. For assays, 1.5 µCi $[^3H]$tyrosine is added to the media and incubated for defined lengths of time at appropriate temperature for enzyme activity. Unreacted $[^3H]$tyrosine is removed from the medium by adsorption onto 10% (w/v) activated charcoal in 0.1 M citric acid, then treated with 50% (w/v) Dowex resin solution. The medium is mixed with scintillant and counted in a beta-counter. A significant increase in $[^3H]H_2O$ levels in the medium of cells that were treated with a test compound compared to $[^3H]H_2O$ levels in the medium of similar cells grown under similar conditions without test compound indicates that the test compound is a candidate for a compound that inhibits melanogenesis.

Yet another example of this type of assay is the radiometric melanin synthesis assay. In this assay, the amount of $[^{14}C]$ tyrosine or $[^{14}C]$DOPA incorporated into $[^{14}C]$melanin is measured. In a non-limiting example of a method of screening for compounds that inhibit melanogenesis that uses this assay, melanogenic cells are grown or incubated in medium containing a test compound. The medium is harvested and 1 µCi $[^{14}C]$tyrosine is added and incubated at the appropriate temperature for four hours. The reaction is terminated with ice-cold 10% (w/v) TCA and the mixture vortexed and frozen for 24 hours. The mixture is then thawed and centrifuged at 1000 g for 15 minutes at 4° C. The pellet is resuspended in ice-cold 5% TCA (w/v). This step is repeated twice. The final pellet containing $[^{14}C]$melanin is solubilized in Soluene®-350 (Packard Instrument Company, Meriden, Conn.) for four hours, mixed with scintillant, and counted. Alternatively, the pellet can be collected on filter paper and counted. A significant increase in $[^{14}C]$melanin levels in media of cells that were treated with a test compound compared to $[^{14}C]$melanin levels in media of similar cells grown under similar conditions, but without the test compound, indicates that the test compound is a candidate for a compound that inhibits melanogenesis.

Another assay is a fluorescence assay. In this assay, the substrate and/or its products are fluorescent. The wavelength of light absorbed and/or emitted by the substrate is different from the wavelength of light absorbed and/or emitted by the products. In a non-limiting example of a method of screening for compounds that inhibit melanogenesis that uses this assay, melanogenic cells are grown in culture in the presence or absence of the test compound. After a period of growth or incubation, the media is removed, tyrosinase substrate added, and a fluorometer used to measure the fluorescence of the growth or incubation medium. The concentration of substrate, time of incubation, temperature of incubation and other reaction conditions can be chosen so that the change in fluorescence is proportional to the levels of tyrosinase activity in the medium being analyzed. A significant difference in fluorescence levels of media from cells treated with a test compound compared to fluorescence levels of media from similar cells grown under similar conditions but without the test compound, indicates that the test compound is a candidate for a compound that inhibits melanogenesis.

Another type of assay involves the precipitation of reaction products. In an example of a method of screening for compounds that inhibit melanogenesis that uses this assay, a substrate of tyrosinase is incubated with the harvested growth or incubation medium under conditions that promote the activity of tyrosinase. The substrate is acted upon by tyrosinase to produce a reaction product that can be precipitated. The reaction product is precipitated. The reaction product can be precipitated from the medium by, for example, increasing or decreasing the temperature of the medium, increasing or decreasing the pH of the medium, increasing or decreasing the ionic strength or salt concentration of the medium, or otherwise altering the medium appropriately, or by centrifugation if the reaction product is insoluble. Substrate concentrations, time of incubation, temperature of incubation, and other reaction conditions can be chosen so that the amount of precipitable reaction product is proportional to the levels of tyrosinase activity in the medium being analyzed. A significant increase in the amount of reaction product precipitated from the media of cells treated with a test compound compared to the amount of reaction product precipitated from the media of similar cells grown under similar conditions but without the test compound indicates that the test compound is a candidate for a compound that inhibits melanogenesis.

1.3 Methods of Screening for Inhibitors of Melanogenesis Using Assays for Tyrosinase Protein The preceding methods of screening serve to identify inhibitors of melanogenesis using assays of tyrosinase activity (i.e., the protein's enzymatic activities). The present invention further provides a method of screening inhibitors of melanogenesis using assays for either extracellular or intracellular tyrosinase protein levels. As explained above, tyrosinase is primarily localized to the melanosomal membrane in melanogenic cells. Compounds that cause tyrosinase to be mislocalized serve to inhibit melanogenesis. In the following methods of screening, assays for determining tyrosinase protein levels and/or locations are used. This can be done using any of the standard techniques of protein detection known in the art. The protein detection assays employed herein can be those described in Harlow and Lane (Harlow, E. and Lane, D., 1988, *Antibodies: A Laboratory Manual*, Cold Spring Harbor Laboratory Press, Cold Spring Harbor, N.Y.), which is incorporated herein by reference in its entirety. These assays include, but are not limited to, immunological assays, including Western blots, solid-phase radioimmunoassays, in situ hybridizations, and immunoprecipitations Anti-tyrosinase antibodies are known in the art, and novel anti-tyrosinase antibodies can be generated using well-known techniques. Id.

In a non-limiting method of screening for compounds that inhibit melanogenesis, melanogenic cells are grown or incubated in medium containing a test compound. The presence, concentration, or amount of tyrosinase in the medium is determined using a protein detection assay as described above. Test compounds that cause treated cells to secrete more tyrosinase than similar cells grown or incubated under similar conditions but without the test compound are candidates for compounds that inhibit melanogenesis.

Another type of assay that can be used in this screen determines the cellular localization of tyrosinase protein. In wild-type melanogenic cells, most tyrosinase is targeted to the melanosomal membrane, while some tyrosinase is secreted. Mutations or compounds that inhibit melanogenesis (e.g., mutations or compounds that inhibit P protein function) can cause tyrosinase to be secreted to the medium in greater amounts or to be mislocalized to non-melanosomal vesicles. These non-melanosomal vesicles can be separated from melanosomes using subcellular fractionation techniques. In a non-limiting example of a method of screening for compounds that inhibit melanogenesis that uses this assay, melanogenic cells are grown or incubated in medium containing a test compound and the cells are harvested. The subcellular distribution of tyrosinase is then determined in these cells and compared to the subcellular distribution of tyrosinase in similar cells grown or incubated under similar conditions but without the test compound. The assay can incorporate any technique or combination of techniques known in the art, including subcellular fractionation (for example, by sucrose or Percoll density gradient centrifugation), Western blotting of the cells contents, and tyrosinase activity assays of each subcellular fraction. A decrease in the fraction of total tyrosinase protein found in the melanosomal fraction, or an increase in the fraction of total tyrosinase protein found in a non-melanosomal fraction, in cells treated with the test compound relative to cells not treated with the test compound indicates that the test compound inhibits melanogenesis.

Other qualitative assays can be used, such as, e.g., microscopic examination of cells treated with the test compound. For example, cell staining techniques, as known in the art, can be used. Cells are grown or incubated in medium containing tyrosine and in the presence of a test compound. The cells are stained using anti-tyrosinase antibodies, then examined microscopically. In a non-limiting example of a method of screening using this type of assay, melanogenic cells are grown or incubated in medium containing a test compound, and prepared for cell staining using techniques commonly known in the art. See, e.g., Harlow and Lane, 1988, supra. Prepared cells are stained using anti-tyrosinase antibodies. The anti-tyrosinase antibodies can be conjugated to a moiety allowing for its detection. Preferably, a secondary antibody is used. The secondary antibody recognizes and binds to the anti-tyrosinase antibody. Preferably, the secondary antibody is conjugated to a moiety allowing for its detection. Alternatively, a tertiary antibody can also be used. The tertiary antibody is preferably conjugated to a moiety allowing for its detection. Examples of moieties allowing for the detection of antibodies include fluorescent molecules (for example, fluoroscein, rhodamine, Hoechst 33258, or Texas red), enzymes (for example, horseradish peroxidase, alkaline phosphatase, or beta-galactosidase), gold particles, radioactive isotope, and biotin. An assay is selected based on the labeling moiety used. For example, fluorescence microscopy can be used to detect fluorescently labeled antibodies. For cells stained with enzyme-conjugated antibodies, the cells are further treated with an appropriate substrate for conversion by the antibody-bound enzyme, followed by examination by light microscopy. Gold-particle labeled antibodies can be detected using light or electron microscopy. Isotope-labeled antibodies can be detected using radiation-sensitive film. For cells stained with biotin-conjugated antibodies, the cells are further treated with streptavidin or avidin. The streptavidin or avidin is conjugated to a moiety that allows for detection such as, for example, a fluorescent molecule, an enzyme, gold particles, or radioactive isotope. Preferably, the cells are co-stained with an antibody or antibodies specific for particular subcellular compartments (e.g., endosomes, lysosomes, melanosomes, etc.). Using any one of these techniques, or any other known technique for detecting antibodies in antibody-stained cells, the subcellular distribution of tyrosinase can be determined. If the test compound causes an increased amount of tyrosinase to be found in non-melanosomal vesicles, and less tyrosinase in melanosomes, then it inhibits melanogenesis.

Another type of assay can be used to determine the presence or absence of the C-terminal portion of the tyrosinase protein. This assay depends, in part, on the discovery that melanogenic cells inhibited for melanogenesis (e.g., by mutations or compounds that inhibit P protein function) contain and secrete a version of tyrosinase that lacks the C-terminal portion of tyrosinase, including its transmembrane domain and its protein sorting signal. As explained above, this truncated form of tyrosinase nonetheless retains catalytic activity. In a non-limiting example of a method of screening based on this assay, melanogenic cells are grown or incubated in the presence of a test compound. An assay is selected that allows the length and/or mass of tyrosinase protein to be determined. For example, Western blots or other immunohistochemical techniques using antibodies that recognize the N-terminal or central portions of the tyrosinase protein, or other standard molecular biological techniques useful for the determination of protein length or mass, can be performed on extracts of these cells and/or on their growth or incubation medium. Antibodies appropriate for these assays can be prepared using standard immunological techniques. See, e.g., Harlow and Lane, 1988, supra. If the assay reveals the presence of a shorter or lower molecular weight form of tyrosinase, relative to similar cells grown or incubated under similar conditions but without the test compound, then the test compound inhibits melanogenesis. Alternatively, Western blots or other immunohistochemical techniques using antibodies recognizing the C-terminal portion of tyrosinase (e.g., the anti-PEP7 antibody prepared as described in Jimenez et al., 1991, *J. Biol. Chem.* 266:1147-1156) can be used in the assay. In these assays, a reduction in the amount of tyrosinase protein detected by the antibodies indicates that the test compound inhibits melanogenesis, because the truncated tyrosinase lacks the sequences recognized by the antibodies.

Both full length tyrosinase, and the truncated tyrosinase found in and secreted by melanogenic cells with inhibited or absent P protein, remain catalytically active when run on non-denaturing polyacrylamide gels. This observation is the basis, in part, of another assay for the truncated tyrosinase protein. Thus, melanogenic cells can be grown or incubated in medium containing a compound to be tested. Either the growth or incubation medium is collected, or cell extracts are prepared, and subjected to non-denaturing polyacrylamide gel electrophoresis. Smaller, more flexible proteins will migrate farther than larger proteins with more complicated three-dimensional structure. Filter paper or a membrane (e.g., nitrocellulose) is soaked in L-DOPA and applied to the gel. Active tyrosinase in the gel converts L-DOPA into melanin, creating dark spots on the filter or membrane indicating the location and, therefore, the relative size, of tyrosinase. If cells treated with the test compound produce two spots on the filter or membrane, wherein one spot indicates tyrosinase of the same size as produced by similar cells grown under similar conditions but without the test compound, and the other spot indicates tyrosinase of smaller relative size, then the test compound is a candidate for a compound that inhibits melanogenesis.

Full length tyrosinase in wild-type melanogenic cells with normal P protein function is found primarily in the insoluble fraction of cell extracts. To be released, it must be solubilized with a detergent (e.g., Triton X-100™). In contrast, the smaller truncated version of tyrosinase in melanogenic cells with inhibited P protein function is found in vesicles in the soluble fraction. These observations are the basis, in part, of another assay that can be used to detect truncated tyrosinase in P protein-compromised cells. Thus, melanogenic cells are grown or Incubated in medium containing a compound to be tested. The cells are harvested and can be subjected to a detergent phase separation to separate membrane-anchored proteins from soluble proteins. For example, the cells can be solubilized on ice in a buffer containing Triton X-114™ detergent. Insoluble contaminants can be spun out at 4° C. Then the supernatant, which contains solubilized proteins, is phase-separated at room temperature or elevated temperatures into a detergent phase and an aqueous phase. The ratio of tyrosinase in the detergent phase (which will contain tyrosinase proteins containing the C-terminal portion of the protein which anchors tyrosinase in the membrane) to tyrosinase in the aqueous phase (which will contain tyrosinase proteins which lack the C-terminal portion) is determined. Alternatively, cells are harvested and membranes disrupted by a freeze/thaw cycle or cycles. The disrupted cells are then separated into a soluble fraction and a membrane-bound, insoluble fraction. The ratio of soluble tyrosinase in the soluble fraction to insoluble, membrane-bound tyrosinase in the membrane fraction is determined. If cells treated with the test compound have higher levels of soluble tyrosinase than insoluble, membrane-bound tyrosinase than that from similar cells grown under similar conditions but without the test compound, then the test compound is a candidate for a compound that inhibits melanogenesis.

1.4 Other Methods of Screening for Inhibitors of Melanogenesis

As described above, the mislocalization and secretion of tyrosinase, and the reduction of tyrosinase activity, are not the only results of an inhibition of melanogenesis. Other melanogenic enzymes are also affected, as is the biogenesis of melanosomes.

Inhibition of melanogenesis by mutations that inhibit P protein function can cause a marked alteration in the amount of several melanogenic proteins produced in melanocytes, Including the TRP-1, TRP-2, and LAMP-1 gene products (Orlow, S. J., and Brilliant, M. H., 1999, supra). In the eyes of wild-type mice, the levels of TRP-1 and TRP-2 gene products are high at birth, fall sharply, increase gradually to another peak at about 2 weeks, then permanently fall to undetectable levels by about 40 days. In mice that lack P protein function, for example, the levels of these proteins are much lower at birth and are undetectable after only a few days (id.).

Another effect of inhibited melanogenesis caused by a mutation which inhibits P protein function is the disruption of a high molecular weight complex comprising tyrosinase, TRP-1 protein, and TRP-2 protein (Orlow, S. J. et al., 1994, supra). For purposes of the present invention, the term "high molecular weight complex" is defined as a group of proteins bound to each other via covalent and/or non-covalent bonds that remain associated with each other during non-denaturing gel filtration, HPLC, or sucrose gradient sedimentation and have an apparent molecular weight of between about 200 kD and about 700 kD. In wild-type melanogenic cells, this "melanogenic complex," which is associated with the melanosome, contains a significant fraction of the cells' complement of tyrosinase, TRP-1 protein and TRP-2 protein. In melanogenic cells inhibited for melanogenesis by inhibition of P protein function, very little of any of these proteins is found in high molecular weight complexes.

Another assay takes advantage, in part, of these effects. In a non-limiting example of a method of screening for compounds that inhibit melanogenesis that uses this type of assay, melanogenic cells are grown or incubated in medium containing a compound to be tested. The cells are harvested, disrupted, and fractionated. This fractionation can be done, for example, using sucrose gradient sedimentation. Aliquots from the sedimentation are assayed for the presence of melanogenic proteins such as, for example, by using assays for tyrosinase, TRP-1, and/or TRP-2 activity, or by using immunohistochemical assays, such as immunoblotting. Increased amounts of any of these three proteins in low density aliquots and/or decreased amounts of any of these three proteins in high density aliquots, relative to similar cells grown or incubated under similar conditions but without the test compound, indicate that the test compound is a candidate for a compound that inhibits melanogenesis.

Another consequence of inhibited melanogenesis can be the aberrant development of melanosomes. Wild-type melanogenic cells typically contain abundant, fully developed, darkly pigmented melanosomes. Such fully developed, darkly pigmented melanosomes are less abundant or absent in melanocytes inhibited for melanogenesis due to a mutation in the P protein-encoding gene when they are grown or incubated in medium containing low concentrations of tyrosine. Rather, these cells contain an unusually large number of immature melanosomes. This phenomenon is the basis, in part, for another assay that can be used. In a non-limiting example of a method of screening for compounds that inhibit melanogenesis that uses this type of assay, melanogenic cells are grown or incubated in medium containing a test compound. The number, size, shape, and/or color of the melanosomes in the cells is assayed. Such assays are well known in the art. For example, cells can be fixed and stained and examined using light microscopy. Alternatively, cells can be fixed, stained, sectioned, and examined using electron microscopy. Alternatively, cells can be fractionated using density centrifugation. Mature melanosomes are denser than immature melanosomes, and so can be separated from them on the basis of density using well known techniques. Cells treated with a test compound that have melanosomes that are altered in number, size, shape, and/or color compared to melanosomes from similar cells grown or incubated under similar conditions but without the test compound indicates that the test compound inhibits melanogenesis.

1.5 Methods of Screening for Inhibitors of P Protein Function

As explained above, the P protein plays a pivotal role in melanogenesis. Melanocytes with loss of function mutations in the P protein-encoding gene are inhibited for melanogenesis. In P deficient or P inhibited cells, inhibition of melanogenesis is correlated with mislocalization of tyrosinase. Whereas in wild-type melanocytes tyrosinase is localized primarily to melanosomes, in melanocytes with loss of function mutations in the P protein-encoding gene, tyrosinase is predominantly secreted or found in non-melanosomal vesicles. Inhibition of melanogenesis and the mislocalization of tyrosinase can be mimicked by treating wild-type melanocytes with compounds that inhibit the function of P protein (e.g., imipramine).

These discoveries are the basis, in part, for a number of screens for inhibitors of melanogenesis. These screens serve to identify inhibitors of melanogenesis by identifying inhibitors of P protein function. Thus, melanogenic cells are grown or incubated in medium containing a compound to be tested for its ability to inhibit P protein function. The effect, if any, of the compound can be determined using, for example, any one of the assays described above. In a non-limiting embodiment, the activity of tyrosinase in the growth or incubation medium of the cells can be measured. For example, tyrosine can be added to the medium, and its conversion to melanin monitored. Alternatively, non-tyrosine or altered tyrosine substrates of tyrosinase can be added to the medium, and their conversion into reaction products by tyrosinase can be followed by, for example, colorimetric assays (e.g., the DOPA oxidase assay), radiometric assays (e.g., the radiometric hydroxylase or radiometric melanin synthesis assays), fluorescence assays, or by the precipitation of reaction products. These assays are described in detail herein above.

Alternatively, the assays of tyrosinase protein may be used. These assays can measure, for example, the amount of tyrosinase in the growth or incubation medium of the cells treated with the compound to be tested, the cellular localization of tyrosinase (e.g., by subcellular fractionation of the cells, or by staining and microscopic examination of the cells), or the length or mass of the tyrosinase molecules within the cells. These assays are described in detail herein above.

Other assays that can be used include those that measure other effects of the inhibition of P protein function. For example, these assays can measure the amount or activity of TRP-1 and/or TRP-2 protein in cells treated with the compound to be tested, the abundance or composition of the high molecular weight melanogenic complex, or the presence or absence of aberrant melanosomes. These assays are described in detail herein above.

Still another assay that can be used involves measuring the intracellular targeting, intracellular levels and/or secretion of a certain class of lysosomal hydrolases. Normally, newly synthesized lysosomal hydrolases are transported from the trans-Golgi network to a late endosome compartment, portions of which are thought to eventually fuse with or form lysosomes. These lysosomes, containing most of the intercellular lysosomal hydrolase activity, can be detected in a large granule fraction prepared from fractionated cells. As illustrated below by way of a non-limiting example, some, but not all, lysosomal hydrolases are not correctly targeted to the lysosome-containing large granule fraction from melan-p cells as opposed to melan-a cells. In particular, lysosomal hydrolases that are transported from the trans-Golgi network to the late endosome via binding to the mannose-6-phosphate/insulin-like growth factor type II receptor (the "M6P/IGF-II receptor") do not accumulate in the large granule fraction. Such incorrectly targeted lysosomal hydrolases include $\beta$-hexosaminidase, $\beta$-glucosidase, $\beta$-glucuronidase and $\beta$-galactosidase. In contrast, acid phosphatase, which is not transported to the late endosome via the M6P/IGF-II receptor, correctly accumulates in the large granule fraction in both melan-a and melan-p cells. Thus, P protein function is also necessary for the correct targeting of lysosomal enzymes that are transported to the late endosome via the M6P/IGF-II receptor. The default pathway for such enzymes is secretion into the exterior of the cell.

These results are the basis, in part, for additional methods of screening for compounds that affect P protein function. Accordingly, in lieu of, or in addition to, assays for the mislocalization of tyrosinase, one can screen for the effect of a test compound on the level and/or localization of any lysosomal hydrolase that is normally transported to the late endosome via the M6P/IGF-II receptor including, but not limited to, $\beta$-hexosaminidase, $\beta$-glucosidase, $\beta$-glucuronidase and $\beta$-galactosidase. Since these lysosomal hydrolases are, like tyrosinase, proteins and more particularly enzymes, any of the methods described above to assay for the presence of tyrosinase's enzymatic activity and/or protein can be adapted to assay lysosomal hydrolases. Assays for the enzymatic activity of these enzymes are well known in the art (and, in part, illustrated below by way of a non-limiting example), as are their amino acid structures and antibodies that recognize the same. For example, one can assay for the presence and/or levels of lysosomal hydrolases in whole cells or cell extracts, in the large granule fraction of a cell extract, and/or in the medium from cells treated with test compounds. Compounds that cause either a decrease in accumulation of such lysosomal enzymes in cells or, more particularly, the large granule fraction, or an increase in secretion of such lysosomal enzymes, are candidates for compounds that inhibit the function of P protein; such candidate compounds are then further analyzed using one of the other methods of the invention.

1.6 Methods of Screening for Compounds that Increase Melanogenesis, Increase P Protein Function and/or Mimic P Protein Function As explained above, wild-type melanogenic cells typically secrete a portion of their tyrosinase into in vitro culture medium. Although the secreted tyrosinase is enzymatically active, it cannot contribute to melanogenesis, which occurs inside the cells melanosomes. As described above, the level of melanogenesis within melanogenic cells is proportional to the fraction of tyrosinase that is localized to melanosomes. Compounds that decrease the amount of tyrosinase localized to melanosomes serve to inhibit melanogenesis. Conversely, compounds that reduce the amount of tyrosinase that is secreted, and thereby increase the amount of tyrosinase localized to melanosomes, are expected to increase melanogenesis. As explained above, P protein activity is required for the localization of tyrosinase to melanosomes. Thus, compounds that increase the activity of P protein in melanogenic cells, as well as compounds that mimic the activity of P protein, will increase melanogenesis by reducing the amount of tyrosinase that is secreted.

A number of screens based, in part, on these observations and predictions can be used to identify compounds that increase melanogenesis, increase the function of P protein, and/or mimic the function of P protein. For example, variations of the assays described above using melanogenic cells to identify inhibitors of melanogenesis and P protein function can be used. Melanogenic cells are grown or incubated in vitro in medium containing a compound to be tested for its ability to increase melanogenesis, increase P protein function or mimic P protein function. The effect, if any, of the compound can be determined using, for example, any one of the assays described above. For example, the activity of tyrosinase in the growth or incubation medium of the cells can be measured. A decrease in the activity of tyrosinase in the medium may indicate that less tyrosinase is being secreted, and that the compound might therefore increase melanogenesis or P protein function.

Alternatively, or in addition, melanogenic cells that do not contain P protein (e.g., melan-p cells) can be used to screen for compounds that mimic P protein function. In one type of assay that can be used in the invention, melanogenic cells that do not contain P protein are incubated in medium containing a compound to be tested for its ability to mimic P protein function and increase melanogenesis. In contrast to normal melanogenic cells, such melanogenic cells that do not contain P protein are light colored in culture (as well as in the animal). If the melanogenic cells that do not contain P protein turn darker in the presence of the compound than in the absence of the compound, then the compound mimics P protein function in whole or in part. The color of the cells can be measured qualitatively such as, for example, by visual inspection, or quantitatively, such as, for example, by reflectance. Alternatively, melanogenic cells that do not contain P protein are treated with the compound to be tested, and the amount of tyrosinase secreted into the medium is assayed. If the amount of tyrosinase in the medium from melanogenic cells that do not contain P protein (e.g., melan-p cells) decreases when the cells are treated with the test compound, then the test compound is a candidate for a compound that mimics P protein function. Tyrosinase activity in the medium can be measured, for example, by using any of the techniques described above. For example, tyrosine can be added to the medium, and its conversion to melanin monitored.

Alternatively, assays of tyrosinase protein may be used. These assays can measure, for example, the amount of tyrosinase in the growth or incubation medium of the cells treated with the compound to be tested, the cellular localization of tyrosinase (e.g., by subcellular fractionation of the cells, or by staining and microscopic examination of the cells), or the length or mass of the tyrosinase molecules present within the cells. A decrease in the amount of tyrosinase protein secreted into the medium, or an increase of tyrosinase protein in melanosomes, indicates that the test compound is a candidate for a compound that increases melanogenesis or mimics or enhances P protein function. If the test compound causes similar effects in melanogenic cells that do not contain Pr protein (e.g., melan-p cells), such a result would indicate that the compound mimics P protein function. These assays are described in detail herein above.

Other assays that can be used include those that measure other effects of an increase in P protein function, mimic of P protein function, and/or an increase in melanogenesis. For example, these assays can measure the amount of TRP-1 and/or TRP-2 protein or activity in cells treated with the compound to be tested, the abundance or composition of the high molecular weight melanogenic complex, or the presence or absence of aberrant melanosomes as described above. An increase in the amount of TRP-1 and/or TRP-2 protein or activity, an increase in the amount of these proteins found in high molecular weight melanogenic complexes, or an increase in the number of high molecular weight complexes, indicates that the test compound is a candidate for a compound that increases melanogenesis or P protein function. If the test compound causes similar effects in melanogenic cells that do not contain P protein (e.g., melan-p cells), such a result would indicate that the compound mimics P protein function. These assays are described in detail herein above.

In a variation of these screens, the amount of secreted tyrosinase is compared to the amount of intracellular tyrosinase. Melanogenic cells are grown or incubated in medium containing a compound to be tested. Using, for example, any of the assays described above, the amount of tyrosinase in the growth or incubation medium is determined and the amount of tyrosinase within these cells is also determined. The ratio of intracellular tyrosinase to secreted tyrosinase is then calculated. If this ratio is higher for cells treated with the compound to be tested than for similar cells grown under similar conditions but without the compound, then the compound increases melanogenesis. In a non-limiting preferred embodiment, such a change in the ratio of intracellular tyrosinase to secreted tyrosinase is observed without a change (e.g., reduction) in the total amount of tyrosinase produced by the cell. Similarly, if melanogenic cells that do not contain P protein (e.g., melan-p cells) are grown or incubated in medium containing the compound to be tested, and the ratio of intracellular tyrosinase to secreted tyrosinase is higher for cells treated with the compound than for untreated cells, then the compound can mimic P protein function, and thereby increase melanogenesis.

1.7 Methods of Screening for Compounds that Affect P Protein Function Using Non-Melanogenic Cells Most non-melanogenic cells do not express P protein or tyrosinase. For purposes of the present invention, the term "non-melanogenic cells" is defined as cells that do not contain melanosomes. However, non-melanogenic cells can be made to express both P protein and tyrosinase, and to synthesize melanin. For purposes of the present invention, the term "cells made to express both P protein and tyrosinase" is defined as cells that do not ordinarily express P protein and/or tyrosinase, but are caused to express both P protein and tyrosinase using any technique known in the art such as, e.g., molecular genetic techniques. For example, heterologous tyrosinase and/or P protein genes can be introduced into the cells by, e.g., transfection, transformation, or transduction. For purposes of the present invention, the term "heterologous" is defined as describing a gene or gene product that does not naturally exist in that organism, or a gene or gene product that is not normally expressed in that cell type. Alternatively, endogenous, but normally quiescent, tyrosinase and/or P protein-encoding genes can be activated to express tyrosinase and/or P protein (e.g. through targeted homologous recombination of transcriptional control sequences, or any other activation method). Several methods of the present invention are based, in part, on the discovery that non-melanogenic cells expressing P protein and tyrosinase together have almost four times as much tyrosinase activity as cells expressing tyrosinase alone. Cells expressing P protein, but not tyrosinase, do not have detectable tyrosinase activity, showing that P proteins effect on tyrosinase activity in these cells is completely dependent on the expression of tyrosinase.

The tyrosinase activity of cells made to express both tyrosinase and P protein is sensitive to the action of compounds that inhibit P protein function. When these cells are treated with, for example, imipramine, the tyrosinase activity of these cells is markedly reduced. The effect of these compounds on tyrosinase activity is totally dependent on the presence of active P protein. Cells expressing tyrosinase but not P protein have tyrosinase activities that are unaffected by the presence of the compound at the concentrations tested.

These observations are exploited in a number of methods of screening for compounds that affect (e.g., decrease or increase) P protein function. Cells that do not otherwise have detectable tyrosinase and/or P protein are made to express both of these proteins. The cells are grown or incubated in medium that contains a compound to be tested. The tyrosinase activity of extracts of these cells is measured. Tyrosinase activity can be measured using any of the assays discussed above, including the radiometric tyrosine hydroxylase assay, colorimetric DOPA oxidase assay, the DHICA converting assay, an assay for the ability to convert [$^{14}$C]DOPA into TCA precipitable material, or by any other method known in the art. If the tyrosinase activity of the extracts of cells-treated with the test compound is lower than the tyrosinase activity of the extracts of similar cells grown under similar conditions but without the test compound, and if the compound does not otherwise decrease tyrosinase activity in the extracts of cells expressing tyrosinase but not P protein, then the compound decreases P protein function. Conversely, if the tyrosinase activity of the extracts of cells treated with the test compound is higher than the tyrosinase activity of the extracts of similar cells grown under similar conditions but without the test compound, and if the compound does not otherwise increase tyrosinase activity in the extracts of cells expressing tyrosinase but not P protein, then the compound increases P protein function.

Another method of screening using non-melanogenic cells made to express tyrosinase and P protein exploits, in part, the discovery that these cells, if incubated long enough, turn black with melanin deposition. Cells expressing tyrosinase and P protein, or tyrosinase but not P protein, are treated with a compound to be tested. The cells are incubated for a period of time sufficient to allow cells expressing both tyrosinase and P protein, but which are not treated with the test compound, to accumulate melanin. The melanin content of treated and untreated cells can be assayed by visual inspection or spectrophotometric analysis of the cells, or by using other techniques well known in the art. If the melanin content of the cells expressing both tyrosinase and P protein and treated with the test compound is lower than the melanin content of similar cells not treated with the compound, then the compound can decrease melanogenesis. If the melanin content of cells expressing tyrosinase but not P protein is not substantially altered by the presence or absence of the compound, then the compound inhibits P protein function. Conversely, compounds that cause an increase in melanin formation in these cells, relative to similar cells grown under similar conditions but without the compound, increase melanogenesis. If the compound also fails to increase melanin formation in non-melanogenic cells expressing a tyrosinase-encoding gene but not a P protein-encoding gene, then the compound increases P protein function.

Alternatively, broken cell extract systems can be devised to study intracellular trafficking of tyrosinase. In a non-limiting example, donor Golgi membranes and cytosol from wild-type melanocytes can be combined with melanosomes prepared from cells of a mouse with a mutation in the tyrosinase gene that inactivates the enzyme. One could then observe the transfer of tyrosinase from the wild-type donor Golgi membranes to the tyrosinase-deficient melanosomes. Addition of a compound that inhibits P protein function would inhibit such transfer.

For those methods using heterologous genes, the heterologous tyrosinase and P protein-encoding genes can be derived from any suitable source. Preferably, they are derived from an animal source. More preferably, they are derived from a mammalian source such as the mouse cells used below in illustrating embodiments. Even more preferably, they are derived from a primate source such as humans. Tyrosinase-encoding genes are well known in the art (see, for example, expression of the human gene cDNA in Bouchard et al, 1989, *J. Exp. Med.* 169 (6), 2029-2042, and the MEDLINE database at accession nos., for example, NM_000372, M27160, and U01873), as are P protein-encoding genes (see for example, Rinchik et al., 1993, *Nature* 361 (6407), 72-76, and the MEDLINE database at accession nos., for example, NM 000275 and U19152 for the human gene).

Expression cassettes are typically used to express heterologous genes in the chosen cell. Each expression cassette contains regulatory sequences designed to express, for example, the tyrosinase-encoding gene and/or the P protein-encoding gene. For expression in prokaryotic cells, preferably each coding sequence found in the expression cassette is operatively linked to at least one regulatory sequence, i.e., a promoter sequence. By "operatively linked" is meant that the regulatory sequence functions to regulate the coding sequence (e.g., controls the timing or amount of expression of the coding sequence, determines initiation or termination of transcription or translation, or affects message stability). For expression in eukaryotic cells, preferably each coding sequence found in the expression cassette is "operatively linked" to at least two regulatory sequences, i.e., a promoter and a polyA sequence. Each expression cassette is operatively linked to the polynucleotide sequence of a vector. Each vector preferably contains polynucleotide sequences that allow for its selection, replication, and maintenance in transfected cells, either as an autonomous extrachromosomal element, or as an integrated component of one or more chromosomes in the transfected cells. Vectors containing expression cassettes that can be adapted to express almost any coding sequence are well known in the art and commercially available. Non-limiting examples of such vectors are illustrated below using the pcDNA vectors available from Invitrogen (San Diego, Calif.).

Any promoter that facilitates a sufficiently high rate of expression can be used in the expression cassette. The promoter can be constitutive or inducible. See, e.g., Resendez et al., 1988, *Mol. Cell Biol.* 8:4579-4584; and Chang et al., 1987, *Proc. Natl. Acad. Sci. USA* 84:680-684, which describe inducible promoters. The choice of the promoter depends on what cell type is used in the screen and the desired level of expression of the heterologous genes encoding tyrosinase and/or P protein. See, e.g., Gossen et al., 1995, *Science* 268: 1766-1769; Gossen and Bujard, 1992, *Proc. Natl. Acad. Sci. USA* 89:5547-5551 and U.S. Pat. Nos. 5,851,984; 5,849,997; 5,827,687; 5,811,260; 5,789,215; 5,665,578; 5,512,483; 5,302,517; 4,959,313; and 4,935,352, which describe useful promoter sequences.

Further non-limiting examples of promoter sequences and elements include the SV40 early promoter region (Bemoist and Chambon, 1981, *Nature* 290:304-310), the promoter contained in the 3' long terminal repeat of Rous sarcoma virus (Yamamoto, et al., 1980, *Cell* 22:787-797), the herpes thymidine kinase promoter (Wagner et al., 1981, *Proc. Natl. Acad. Sci.* (*USA*) 78:1441-1445), the regulatory sequences of the metallothionein gene (Brinster et al., 1982, *Nature*

296:3942); prokaryotic expression vectors such as the β-lactamase promoter (Villa-Kamaroff, et al., 1978, *Proc. Natl. Acad. Sci.* (*USA*) 75:3727-3731), and the tac promoter (DeBoer, et al., 1983, *Proc. Natl. Acad. Sci.* (*USA*) 80:21-25); see also "Useful proteins from recombinant bacteria" in Scientific American, 1980, 242:74-94; plant expression vectors comprising the nopaline synthetase promoter region (Herrera-Estrella et al., *Nature* 303:209-213) or the cauliflower mosaic virus 35S RNA promoter (Gardner, et al., 1981, *Nucl. Adds Res.* 9:2871), and the promoter of the photosynthetic enzyme ribulose biphosphate carboxylase (Herrera-Estrella et al., 1984, *Nature* 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: the elastase I gene control region, which is active in pancreatic acinar cells (Swift et al. (1984) *Cell* 38:639-646; Omitz et al., 1986, *Cold Spring Harbor Symp. Quant. Biol.* 50:399-409; MacDonald, 1987, *Hepatol.* 7:425-515); the insulin gene control region, which is active in pancreatic beta cells (Hanahan, 1985, *Nature* 315:115-122); the immunoglobulin gene control region, which is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region, which is active in testicular, breast, lymphoid and mast cells (Leder et al., 1986, *Cell* 45:485-495); the albumin gene control region, which is active in liver (Pinkert et al., 1987, *Genes and Devel.* 1:268-276); the alpha-fetoprotein gene control region, which is active in liver (Krumlauf et al., 1985, *Mol. Cell. Biol.* 5:1639-1648; Hammer et al., 1987, *Science* 235:53-58); the alpha 1-antitrypsin gene control region, which is active in the liver (Kelsey et al., 1987, *Genes and Devel.* 1:161-171); the beta-globin gene control region, which is active in myeloid cells (Mogram et al., 1985, *Nature* 315:338-340; Kollias et al., 1986, *Cell* 46:89-94); the myelin basic protein gene control region, which is active in oligodendrocyte cells in the brain (Readhead et al., 1987, *Cell* 48:703-712); the myosin light chain-2 gene control region, which is active in skeletal muscle (Sani, 1985, *Nature* 314:283-286); and the gonadotropic releasing hormone gene control region, which is active in the hypothalamus (Mason et al., 1986, *Science* 234:1372-1378).

Another regulatory element that can be used in the expression cassette for eukaryotic cell expression is a polyA sequence (or polyA signal), which should be capable of efficiently inducing polyadenylation of a transcript specific for the coding sequence to which the polyA sequence is operatively linked. See, e.g., U.S. Pat. Nos. 5,861,290; 5,851,984; 5,840,525 and 5,627,033, which discuss polyA sequences.

In another non-limiting embodiment, the expression cassette used according to the present invention may further comprise an enhancer element, a 5' or 3' untranslated sequence (or region), one or more introns, a sequence that regulates RNA stability, or a combination of more than one of these elements. Any sequence that falls into any of these categories can be used in the vector of the present invention. See U.S. Pat. Nos. 5,861,290; 5,851,984; 5,840,525; 5,681,744 and 5,627,033, which discuss these regulatory elements. The term "5' untranslated sequence" refers to the sequence of an mRNA molecule between the transcription initiation site and the translation initiation site. The term "3' untranslated sequence" refers to the sequence of an mRNA molecule between the translation termination site and the polyA tail.

The heterologous genes used in these assays are typically introduced into the chosen cells by transfection, transduction, transformation, or any other suitable technique known in the art. For example, electroporation, calcium phosphate coprecipitation, microinjection, lipofection, etc., can be used. See, e.g., U.S. Pat. Nos. 5,814,618 and 5,789,215, which describe transfection methods. The cells that take up the heterologous gene or genes, either through integration into their genome or by maintenance as part of an extrachromosomal element, are then preferably selected by standard techniques. Thus, a selectable marker can be included in the vector which allows a cell that has the marker, and thus cells that contain the vector and the heterologous gene or genes, to be isolated from cells that do not have the marker. Whether a selectable marker is necessary to prepare the cells used in these assays depends on the particular method by which the vector is introduced into the cells. For example, if the vector is introduced into the cells via microinjection, a selectable marker may be less useful than if electroporation is used because the transformation frequency tends to be higher for microinjection. For example, the marker can enable a cell to grow under selective conditions, i.e. conditions under which the cell could not grow if it did not have the marker (e.g., the neomycin resistance gene and the hypoxanthine phosphoribosyltransferase gene). A marker can also provide another means by which to identify the cell which took up the heterologous polynucleotide molecule or vector (e.g., by preferential staining). See, e.g., U.S. Pat. Nos. 5,851,984 and 5,789,215, which describe selectable markers.

The cells used in these assays can typically be derived from any source. The cells used in these assays can be cells derived from a mammalian animal, for example: a sheep, cow, pig, or other farm animal; a cat, dog, or other domesticated animal; a mouse, rat, or other rodent; a monkey, ape, or other primate; and most preferably a human. Alternatively, the cells used in these assays can be derived from non-mammalian animals such as, for example, a bird, fish, reptile, amphibian, or insect. Cells derived from animals for use in these assays can be of any type such as, for example, fibroblasts, glial cells, keratinocytes, hepatocytes, ependymal cells, bone marrow cells, hippocampal cells, stem cells, embryonic stem cells, hematopoietic stem cells, olfactory mucosa cells, adrenal cells, leukocytes, lymphocytes, chromaffin cells, neurons, cells of the immune system, macrophages, Schwann cells, oligodendrocytes, astrocytes, germline cells, somatic cells, epithelial cells, endothelial cells, adrenal medulla cells, osteoblasts, osteoclasts, myoblasts, pancreatic cells (e.g., of the islets of Langerhans), or a mixture of more than one of the above cell types, etc. Alternatively, the cells used in these assays can be derived from a plant source such as, for example, a dicotyledon such as, e.g., tobacco, or a monocotyledon, such as, e.g., corn. Alternatively, the cells used in these assays can be derived from a unicellular eukaryotic organism such as, for example, a protozoan or a yeast or other unicellular fungus. Methods of growing these cells are specific to each cell type and within the skill of the art.

In a preferred embodiment, established cell lines from any of these sources can be used for these assays. Examples of suitable cell lines include, but are not limited to, Chinese Hamster Ovary (CHO) cells, HeLa cells, NRK cells, A293 cells, and COS cells, which are commercially available; e.g., from the American Type Culture Collection, Manassas, Va. The cells should have the ability to proliferate when grown in in vitro culture. Following introduction of the heterologous gene or genes into the cells, and selection for cells that have taken up the heterologous gene or genes, such cells, in a preferred embodiment, should be useful to establish a cell line that can be grown, stored, re-grown, etc., for extended periods of time in in vitro culture. See, e.g., U.S. Pat. No. 5,814,618, which describes cells useful for the assays of the present invention.

1.8 High-Throughput Methods of Screening for Compounds that Affect or Mimic P Protein Function The methods of screening for compounds that affect or mimic P protein function described above can be used to test individual compounds or small numbers or large numbers of compounds contemporaneously. High-throughput methods of screening, as known in the art, are preferable.

For purposes of the present invention, the term "high-throughput method of screening" is defined as a method of screening that allows for large numbers of compounds to be tested concurrently. Each or all of the steps in screening compounds that affect or mimic P protein function are amenable to high throughput methods of screening for candidate compounds. Preferably, the high-throughput methods of screening are partially or fully automated, reducing the amount of attention required to test each compound. For example, an increase in the amount of tyrosinase secreted into the medium, or total levels of tyrosinase activity, can be detected easily in the formats (such as, e.g., 96 well plates) typically used in high-throughput methods of screening. High-throughput methods of screening are well known in the art and can be performed in any of a number of formats. Laboratory automation, including robotics technology, can significantly decrease the time necessary to screen large numbers of compounds, and is commercially available from, for example, Tecan (Research Triangle Park, N.C.), Scitec Laboratory Automation SA (Lausanne, Switzerland), Rosys (New Castle, Del.), Rixan Associates Inc. (Dayton, Ohio), CRS Robotics (Burlington, Ontario Canada), Fanuk Robotics, and Beckman-Coulter Sagian (Indianapolis, Ind.), to name just a few companies. Upon identifying candidate compounds, secondary methods of screening can be performed to determine the cellular and/or in vivo effects of the candidate compounds on P protein function.

1.9 Secondary Methods of Screening and Additional Methods of Screening for Compounds that Affect or Mimic P Protein Function Each of the above methods of screening can be used by itself to identify compounds that are likely to affect or mimic P protein function. Alternatively, a plurality of methods of screening can be used serially to confirm, or to determine more accurately, the P protein affecting properties of one or more compounds. For example, any of the above methods of screening can be used as a primary method of screening, followed by a secondary method of screening. For purposes of the present invention, the term "primary method of screening" is defined as the first method of screening used to test the ability of a compound to affect or mimic P protein function. For purposes of the present invention, the term "secondary method of screening" is defined as any method of screening that is not the primary method of screening. The use of secondary methods of screening is particularly important when the primary method of screening is based on the identification of compounds that lower the activity of tyrosinase or the amount of melanin produced, or that lower the amount of tyrosinase secreted. Direct inhibitors of tyrosinase will also cause a reduction in the activity of tyrosinase and the amount of melanin produced, or can cause a reduction in tyrosinase activity, but would not necessarily affect P protein function.

Any of the methods of screening described above can also be used as a secondary method of screening. For example, one can identify candidate compounds using as a primary screen the assay for an effect on tyrosinase activity in cells made to express tyrosinase and P protein, yet which don't affect tyrosinase activity in cells made to express tyrosinase alone. Promising compounds from this primary screen can then be tested in a secondary screen in an assay for their effect on cellular localization of tyrosinase and/or lysosomal enzymes in melanogenic cells. Of the methods of screening described above, the ones which rely upon identification of the mislocalization of tyrosinase protein or activity or size are preferred as secondary methods of screening.

In one embodiment, a secondary screen is employed to distinguish the effects of test molecules that effect the melanogenic pathway in general and P Protein in particular, and those that inhibit protein synthesis, trafficking and proteolysis. For example, in an assay for activators of P protein function, a secondary screen can simply entail visually examining the test melanocytes to ensure a darker color and, therefore, an increase in P protein activity, rather than a general inhibition of protein synthesis, trafficking or proteolysis by the test molecule and resulting decrease in tyrosinase secretion. Alternatively, the cells can be histologically examined, preferably by electron microscopy, optionally together with DOPA staining (as described in Example 4, infra), to determine their melanosome content. A true activator of P protein activity will promote the maturation of melanosomes from stages I-III to stages III-IV, whereas an inhibitor of protein synthesis, trafficking and proteolysis is unlikely to promote melanosome maturation.

Other methods of screening can be used. For example, compounds can first be screened for binding affinity to purified P protein. Alternatively, a compound identified by a primary method of screening as affecting P protein function can be tested for direct binding to purified P protein in vitro, or by copurification with P protein from P protein-expressing cells treated with the compound. Each of these methods of screening can determine whether the compound binds directly to P protein. A compound that can bind directly to P protein and which also affects tyrosinase activity or localization or some other aspect of melanogenesis is likely to directly affect P protein function. Alternatively, a compound identified by a primary method of screening as affecting P protein function can be tested for the ability to affect tyrosinase directly. For example, the test compound can be added to a system that contains tyrosinase but not P protein. Such a system can be, for example, an in vitro system containing purified or partially purified tyrosinase protein free or essentially free of P protein. Alternatively, it can be a cell that expresses tyrosinase but not P protein. If the effect of the test compound on tyrosinase is P protein independent, then the test compound does not affect P protein function. If the effect of the test compound on tyrosinase is also observed in the absence of cellular trafficking (e.g., on purified tyrosinase protein, and not in cells), then the test compound does not mimic P protein function.

While preferred primary methods of screening, especially those that are high-throughput methods of screening, are those with the lowest costs (that is, can be performed as quickly, with as little human supervision, and using as few materials as possible), secondary methods of screening can be more time, labor, and material-intensive. This is because the secondary methods of screening are performed only on test compounds that are identified by the primary method of screening as affecting or mimicking P protein function. These compounds are expected to be a small fraction of the total number of compounds tested in any large scale, high-throughput screening effort. Examples of methods of screening that are better suited for secondary screens than for primary screens include administration of a test compound to an animal (e.g., topically, subcutaneously, or orally) or to animal skin equivalents grown in culture, where lightening of the skin or skin equivalent indicates that the compound inhibits P protein function. Or, for compounds that mimic P protein function, the secondary screen can include administration of the test compound to a melan-p animal or animal skin equivalent, where darkening of the skin or skin equivalent indicates that the compound mimics P protein function.

Primary and secondary methods of screening can be used in another way to identify compounds that affect or mimic P protein function. Once a compound that affects or mimics P protein function is identified by using, for example, a primary method of screening, chemical analogs of the compound can be selected or created. For purposes of the present invention, the term "chemical analog" is defined as a compound that is chemically related to another chemical compound. The relationship is preferably structural as known in the art such as where, for example, the two compounds differ only in the location of a substituent, such as, e.g., a hydroxyl or alkyl group, or are chemical homologs of each other. Alternatively, the relationship might be functional such as where, for example, both compounds affect the same mechanism, such as, e.g., where both compounds are kinase inhibitors. Methods for designing or selecting chemical analogs are described below in Section 2.3. These chemical analogs can then be tested for the ability to affect or mimic P protein function using, for example, any method described above. The secondary method of screening can be the same as the primary method of screening, or it can be a different method of screening. Chemical analogs are sought which have a stronger effect on P protein function than the original test compound. This procedure can be repeated serially to identify or create compounds of increasing efficacy.

1.10 Other Compounds Identified by the Methods of Screening

The methods of screening of the invention as described herein, supra, are also useful and easily adaptable by those skilled in the art for the identification of other compounds that inhibit or induce melanogenesis. By way of a non-limiting example, the methods of screening of the invention may be used to identify compounds that effect an alteration in late endosomal/lysosomal trafficking, and therefore, reduce or inhibit melanogenesis and/or pigmentation. Such compounds are also useful as skin lightening agents.

In a certain embodiment, the methods of screening may be used to identify compounds that effect an alteration in late endosomal/lysosomal cholesterol trafficking and thereby reduce or inhibit melanogenesis and/or pigmentation. Such compounds are also useful as skin lightening agents. Intracellular cholesterol originates from two sources: (1) endocytosis of plasma lipoproteins, which contain free and esterified cholesterol and triglycerides; and (2) endogenous synthesis of free cholesterol in the endoplasmic reticulum (ER). Both endocytosed cholesterol and endogenously synthesized cholesterol are trafficked within the cell and ultimately are distributed to various membranes, stored as cholesterol ester in lipid droplets, or exported in plasma lipoproteins. In general, the trafficking of cholesterol involves endocytosis of plasma lipoproteins that are delivered to late endosomes/lysosomes for hydrolysis of esterified cholesterol and movement of subsequent free cholesterol from the late endosome/lysosome to the ER or plasma membrane (PM). From the ER, cholesterol may be trafficked to the trans-Golgi network (TGN), and from there to the plasma membrane. Cholesterol can also move from the PM back to the ER (Liscum et al. (1999) *Biochim. Biophys. Act* 1438:19-37). Although exact mechanisms involved in late endosomal/lysosomal cholesterol trafficking are not well understood, at least one protein is specifically known to be involved. Defective Niemann Pick type C1 (NPC1) protein has been slow to demonstrate the movement of cholesterol to the PM and to the ER, trapping free cholesterol in a lysosomal or a cholesterol-sorting compartment (Cruz et al. (2000) *J. Biol. Chem.* 275:4013-21).

The screening methods of the invention may by utilized to identify compounds that effect an alteration in late endosomal/lysosomal trafficking, and, in some instances, effect an alteration in late endosomal/lysosomal cholesterol trafficking.

2 Compounds for Inhibiting or Inducing Melanogenesis 2.1 Compounds for Inhibiting, Increasing or Mimicking P Protein Function Compounds that can be screened in accordance with the present invention include but are not limited to small organic molecules that are able to gain entry into a cell and affect P protein activity. A number of compound libraries are commercially available from companies such as Pharmacopeia (Princeton, N.J.), Arqule (Medford, Mass.), Enzymed (Iowa City, Iowa), Sigma-Aldrich (St. Louis, Mo.), Maybridge (Trevillett, United Kingdom), Trega (San Diego, Calif.) and PanLabs (Bothell, Wash.), to name just a few sources. One also can screen libraries of known compounds, including natural products or synthetic chemicals, and biologically active materials, including proteins, for compounds that affect or mimic P protein function.

One class of preferred compounds for use in the methods of the present invention comprises chemical analogs of imipramine. As described above, imipramine inhibits P protein function. Imipramine is a tricyclic tertiary amine used in the treatment of depression. See Gilman, A. G. et al., eds, 1990, *Goodman and Gilman's The Pharmacological Basis of Therapeutics*, Eighth Edition, 405-14, Pergamon Press, New York. Other tricyclic tertiary amines used in the treatment of depression such as, for example, amitriptyline, trimipramine, or doxepin (Sigma, St. Louis, Mo.) (see id.) can be test compounds in screens for compounds that affect P protein function. Secondary amines used in the treatment of depression such as, for example, desipramine, nortriptyline, protriptyline, amoxapine, or maprotiline (Sigma, St. Louis, Mo.) (see id.) also are preferred compounds for the screens of the present invention. These chemical analogs of imipramine all share structural and functional characteristics with imipramine. Other chemical analogs of imipramine that are preferred compounds for use in the methods of the present invention include chemicals with functional and/or structural similarities to imipramine. For example, the atypical antidepressants such as, for example, trazodone and fluoxetine (Sigma, St. Louis, Mo.), lack structural similarity with imipramine (see id.), but share the functional property with imipramine of being useful antidepressants, and so are preferred compounds for the screens of the present invention. Tricyclic compounds, tertiary amines, and secondary amines without antidepressant effects also are preferred compounds of the present invention.

Another class of compounds that can be used to inhibit the function of P protein are P protein-encoding gene antisense nucleic acids. A P protein-encoding gene antisense nucleic acid as used herein refers to an oligonucleotide or polynucleotide molecule having a nucleic acid sequence capable of hybridizing to a portion of a P protein-encoding RNA (preferably mRNA) by virtue of some degree of sequence complementarity. The antisense nucleic acid should be complementary to either a coding and/or noncoding region of a P protein mRNA such that it inhibits P protein function by reducing the amount of P protein synthesized.

The antisense nucleic acids of the present invention can be oligonucleotides that are double-stranded or single-stranded, RNA or DNA, or a modification or analog thereof, which can be directly administered to a cell, or to the skin of an animal, or which can be produced intracellularly by transcription of heterologous, introduced sequences.

In one embodiment, the present invention is directed to methods for inhibiting the expression of a P protein-encoding nucleic acid sequence in a prokaryotic or eukaryotic cell comprising providing the cell with an effective amount of a composition comprising a P protein-encoding gene antisense nucleic acid of the present invention.

The P protein-encoding gene antisense nucleic acids of the present invention are at least about six nucleotides in length and are more preferably oligonucleotides ranging from about 6 to about 50 oligonucleotides. In specific aspects, the oligonucleotide is at least about 10 nucleotides, at least about 15 nucleotides, at least about 100 nucleotides, or at least about 200 nucleotides in length. The oligonucleotides can be DNA or RNA, or chimeric mixtures or derivatives, and modified versions thereof, which can either be single-stranded or double-stranded. The oligonucleotide can be modified at the base moiety, sugar moiety, or phosphate backbone level. The oligonucleotide may include other appending groups such as peptides, or agents facilitating transport across the cell membrane (see, e.g., Letsinger et al., 1989, *Proc. Natl. Acad. Sci. (USA)* 86:6553-6556; Lemaitre et al., 1987, *Proc. Natl. Acad. Sci. (USA)* 84:648-652; PCT Publication No. WO 88/09810, published Dec. 15, 1988), hybridization-triggered cleavage agents (see, e.g., Krol et al., 1988, *BioTechniques* 6:958-976), or intercalating agents (see, e.g., Zon, 1988, *Pharm. Res.* 5:539-549). In a preferred aspect of the present invention, a P protein-encoding gene antisense oligonucleotide is a single-stranded DNA molecule.

The oligonucleotide may be modified at any position on its structure with substituents generally known in the art. The P protein-encoding gene antisense oligonucleotide may comprise at least one modified base moiety which is selected from a group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

In another embodiment, the oligonucleotide comprises at least one modified sugar moiety selected from a group including, but not limited to, arabinose, 2-fluoroarabinose, xylulose, and hexose. In yet another embodiment, the oligonucleotide comprises at least one modified phosphate backbone component selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. In yet another embodiment, the oligonucleotide is an alpha-anomeric oligonucleotide. An alpha-anomeric olignucleotide forms specific double-stranded hybrids with complementary RNA in which, contrary to the usual beta-units, the strands run parallel to each other (Gautier et al., 1987, *Nucl. Acids Res.* 15:6625-6641).

The oligonucleotide may be conjugated to another molecule such as, e.g., a peptide, hybridization triggered cross-linking agent, transport agent, hybridization-triggered cleavage agent, etc.

Oligonucleotides of the present invention may be synthesized by standard methods known in the art including, e.g. by use of an automated DNA synthesizer (such as are commercially available from Biosearch, Applied Biosystems, etc.). As examples, phosphorothioate oligonucleotides may be synthesized by the method of Stein et al., 1988, *Nucl. Acids Res.* 16:3209, and methylphosphonate oligonucleotides can be prepared by use of controlled pore glass polymer supports using the method of Sarin et al., 1988, *Proc. Natl. Acad. Sci. (USA)* 85:7448-7451, etc.

In a specific embodiment, the P protein antisense oligonucleotide comprises catalytic RNA, or a ribozyme (see, e.g., PCT International Publication WO 90/11364, published Oct. 4, 1990; Sarver et al., 1990, *Science* 247:1222-1225). In another embodiment, the oligonucleotide is a 2'-0-methylribonucleotide (Inoue et al., 1987, *Nucl. Acids Res.* 15:6131-6148), or a chimeric RNA-DNA analogue (Inoue et al., 1987, *FEBS Lett.* 215:327-330).

In an alternative embodiment, the P protein-encoding gene antisense nucleic acid of the invention is produced intracellularly by transcription from an heterologous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the P protein-encoding gene antisense nucleic acid. Such a vector can remain episomal or become chromosomally integrated, as long as it can be transcribed to produce the desired antisense RNA. Such vectors can be constructed by standard recombinant DNA technology methods known in the art. Vectors can be plasmids, viral vectors, or others known in the art as useful for replication and expression in mammalian cells. Expression of the sequence encoding the P protein-encoding gene antisense RNA can be regulated by any promoter known in the art to act in such cells. Such promoters can be inducible or constitutive, and can include but are not limited to those listed above.

The antisense nucleic acids of the invention comprise a sequence complementary to at least a portion of an RNA transcript of a P protein-encoding gene, preferably a human P protein-encoding gene. However, absolute complementarity, although preferred, is not required, as long as the antisense nucleic acid has sufficient complementarity to be able to hybridize with the RNA, forming a stable duplex. In the case of double-stranded P protein-encoding gene antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a P protein-encoding gene RNA it may contain and still form a stable duplex (or triplex, as the case may be). One skilled in the art can determine the mismatch tolerance by use of standard procedures to, e.g., determine the melting point of the hybridized complex.

Compounds effective at increasing or mimicking P protein function include bafilomycin A1 and concanamycin A. Bafilomycins and concanamycins are unusual macrolide antibiotics which have been isolated from *Streptomyces* (Drose, S. et al. (1997) *J. Exp. Biol* 200:1-8). These compounds have been shown to inhibit the activity of vacuolar ATPases (V-AT-Pases) at nanomolar concentrations and ATPases with phosphorylated states (P-ATPases) at micromolar concentrations (Bowman, E J. et al (1988) *Proc. Natl. Acad. Sci.* (*USA*) 85:7972-6). Furthermore, bafilomycin A1 and concanamycin A and B have been shown to inhibit p-glycoprotein ATPase activity at micromolar concentrations (Sharom, F. J. et al. (1995) *Biochem. J.* 308:381-90). At nanomolar concentrations, bafilomycin A1 and concanamycin A activate melanogenesis in certain amelanotic melanoma cells that nonetheless express tyrosinase (Ancans, J. et al. (2000) *FEBS Lett.* 478:57-60).

The present invention provides for these compounds and analogs thereof for the activation of melanogenesis in melan-p-melanocytes. Bafilomycin A1 and concanamycin A may be isolated from *Streptomyces as* previously described or may be obtained from Sigma (St. Louis, Mo.).

2.2 Compounds that Inhibit Late Endosomal/Lysosomal Trafficking

Compounds that can be screened in accordance with the present invention include, but are not limited to, small organic molecules that are able to gain entry into a cell and alter or inhibit late endosomal/lysosomal trafficking. A number of compound libraries are commercially available from companies such as Pharmacopeia (Princeton, N.J.), Arqule (Medford, Mass.), Enzymed (Iowa City, Iowa), Sigma-Aldrich (St. Louis, Mo.), Maybridge (Trevillett, United Kingdom), Trega (San Diego, Calif.) and PanLabs (Bothell, Wash.), to name just a few sources. Libraries of known compounds, including natural products or synthetic chemicals, and biologically active materials, including proteins, for compounds that alter or inhibit late endosomal/lysosomal trafficking may also be screened.

An alteration in late endosomal/lysosomal trafficking may be effected by contacting the melanocyte with a compound such as progesterone, a hydrophobic amine, sphingosine, an antagonist of a late endosomal/lysosomal trafficking protein, or a compound of the formula

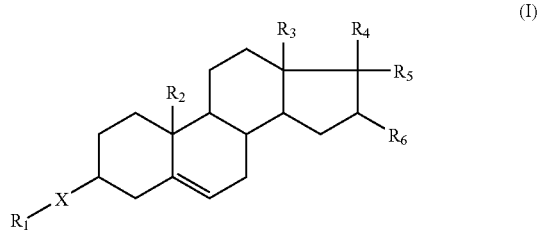

(I)

wherein X is O or S. In a preferred embodiment, X is O.

$R_1$ is —C(O)($C_1$-$C_6$)alkyl or —($CH_2$)$_n$—O—($C_1$-$C_6$) alkyl, or —($CH_2$)$_n$—$NR_7R_8$ where n is 0-3, where each of $R_7$ and $R_8$ are independently selected from H and ($C_1$-$C_6$)alkyl. Preferably, each of $R_7$ and $R_8$ are independently selected from —C(O)($C_1$-$C_3$)alkyl, —$CH_2$—O—($C_1$-$C_3$)alkyl, or —($CH_2$)$_2$—N($C_1$-$C_3$ alkyl)$_2$. More preferably, each of $R_7$ and $R_8$ is independently selected from —C(O)$CH_3$, —$CH_2$—O—$CH_3$, or —($CH_2$)$_2$—N($CH_3$)$_2$.

$R_2$ is H or ($C_1$-$C_6$)alkyl. In some embodiments, $R_2$ is ($C_1$-$C_3$)alkyl. In preferred embodiments, $R_2$ is —$CH_3$.

$R_3$ is H or ($C_1$-$C_6$)alkyl. In preferred embodiments, $R_3$ is ($C_1$-$C_3$)alkyl. In more preferred embodiments, $R_3$ is —$CH_3$.

$R_4$ is —C(O)($C_1$-$C_6$)alkyl. Preferably, $R_4$ is —C(O)($C_1$-$C_3$)alkyl. In more preferred embodiments, $R_4$ is —C(O)$CH_3$ or —C(O)$CH_2CH_3$.

$R_5$ is H or —($C_1$-$C_6$)alkyl. Preferably, $R_5$ is H or —$CH_3$. In another embodiment, $R_4$ and $R_5$ taken together are =O.

$R_6$ is H or —($C_1$-$C_6$)alkyl or —($CH_2$)$_n$—$NR_9R_{10}$, where each of $R_9$ and $R_{10}$ are independently selected from H and ($C_1$-$C_6$)alkyl. Preferably, $R_6$ is H or —$CH_3$, or —$CH_2CH_3$ or —$CH_2NH_2$. In another embodiment, $R_5$ and $R_6$ are combined with the carbon atoms to which they are attached to form a $C_5$-$C_8$ carbocyclic ring, and preferably a $C_6$ carbocyclic ring, which can be substituted by one to three of halogen, OH, —($C_1$-$C_6$)alkyl, —($C_1$-$C_6$)alkoxy, amino, =O, ($C_1$-$C_6$)alkylamino, di-((($C_1$-$C_6$)alkyl)amino, trifluoromethyl, or —$OCF_3$, which substituents can be substituted anywhere on the carbocyclic ring where it is possible to make such substitutions.

The term "alkyl", as used herein, unless otherwise indicated, includes saturated monovalent hydrocarbon radicals having straight, branched or cyclic moieties or combinations thereof. Any substituents or functional groups on the alkyl group, as indicated herein, can be substituted anywhere on the alkyl group.

The term "halo", as used herein, refers to halogen and, unless otherwise indicated, includes chloro, fluoro, bromo and iodo.

Compounds of formula I may contain chiral centers and, therefore, may exist in different enantiomeric and diastereomeric forms. This invention relates to all optical isomers, stereoisomers and tautomers of the compounds of formula I, and mixtures thereof, and to all pharmaceutical compositions and methods of treatment defined above that contain or employ them, respectively.

Formula I, as defined above, also includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

The present invention also relates to the pharmaceutically acceptable acid addition and base salts of any of the aforementioned compounds of formula I. The acids which are used to prepare the pharmaceutically acceptable add addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

The compounds useful according to the invention that are basic in nature are capable of forming a wide variety of different salts with various inorganic and organic adds. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic add in an aqueous solvent medium or in a suitable organic solvent, such as methanol or ethanol. Upon careful evaporation of the solvent, the desired solid salt is readily obtained.

Those compounds useful according to the invention that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of formula I. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantifies of reagents are preferably employed in order to ensure completeness of reaction and maximum yields of the desired final products.

Compounds of generic formula (I) are disclosed and may be synthesized following procedures detailed in WO 00/58549 and U.S. Pat. Nos. 5,232,917, 3,210,386, 3,389,051, and 2,794,815.

The compounds useful according to the invention, and their pharmaceutically acceptable salts, are useful in the treatment of disorders of human pigmentation, including solar and simple lentigines (including age/liver spots), melasma/chloasma and postinflammatory hyper-pigmentation. Such compounds reduce skin melanin levels by inhibiting the production of melanin, whether the latter is produced constitutively or in response to UV irradiation (such as sun exposure). Thus, some of the active compounds used in this invention can be used to reduce skin melanin content in non-pathological states so as to induce a lighter skin tone, as desired by the user, or to prevent melanin accumulation in skin that has been exposed to UV irradiation. They can also be used in combination with skin peeling agents (including glycolic acid or trichloroacetic acid face peels) to lighten skin tone and prevent repigmentation. Other compounds useful according to the invention, and their pharmaceutically acceptable salts, are useful in the treatment of skin conditions where insufficient skin pigmentation is produced, or where the subject, for cosmetic purposes, simply wishes to develop a "sunless tan".

The appropriate dose regimen, the amount of each dose administered, and specific intervals between doses of the active compound will depend upon the particular active compound employed, the condition of the patient being treated, and the nature and severity of the disorder or condition being treated. Preferably, the active compound is administered in an amount and at an interval that results in the desired treatment of or improvement in the disorder or condition being treated.

For skin lightening, an active compound used in the present invention can also be used in combination with sun screens (UVA or UVB blockers) to prevent repigmentation, to protect against sun or UV-induced skin darkening or to enhance their ability to reduce skin melanin and their skin bleaching action. For skin lightening, an active compound used in the present invention can also be used in combination with retinoic acid or its derivatives or any compounds that interact with retinoic acid receptors and accelerate or enhance the invention's ability to reduce skin melanin and skin bleaching action, or enhance the invention's ability to prevent the accumulation of skin melanin. For skin lightening, an active compound used in the present invention can also be used in combination with 4-hydroxyanisole. For skin lightening, the active compounds used in this invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

Figure 16:
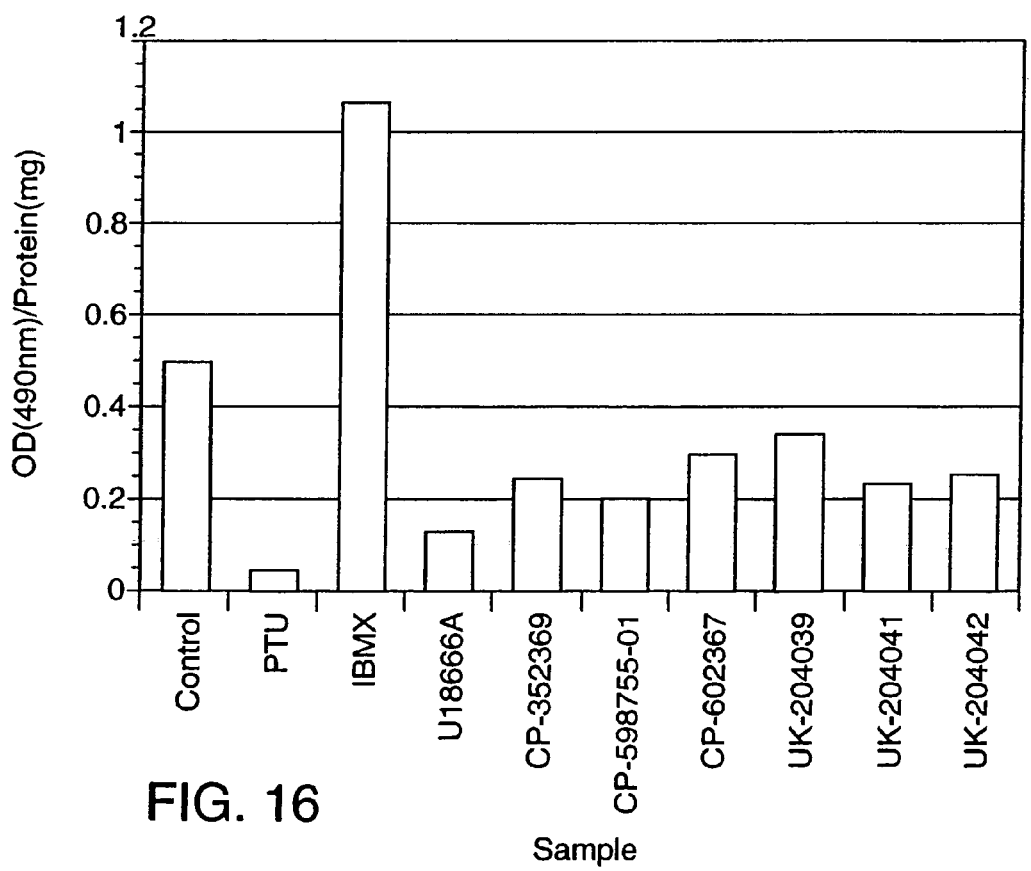
FIG. 16 is a graphic representation providing melanin optical density (OD) determinations for melan-a melanocytes incubated with derivatives of U18666A. Control cells received no drug treatment, and test cells were treated with 300 µM PTU (Sigma, St. Louis, Mo.), 100 µM IBMX (Sigma, St. Louis, Mo.), 2.5 µM U18666A, and 5 µM U18666A analogs: 5 µM CP-59875501, 5 µM CP-602367, 5 µM UK-204039, 5 µM UK-204041, and 5 µM UK-204042 (Pfizer, Inc., Groton, Conn.).

Non-limiting examples of compounds that cause an alteration in late endosomal/lysosomal trafficking of cholesterol include U18666A (formula VIII) and its derivatives (e.g., formulae II-VII), either alone or in combination. Useful examples of U18666A derivatives include CP-598755-01 (formula III), CP-602367 (formula IV), CP-352369 (formula II), UK-204039 (formula V), UK-204041 (formula VI), and UK-204042 (formula VII). Generic formula I presented herein is derived from U18666A and its derivatives presented herein (also see FIG. 16).

Progesterone is another compound useful in the methods and compositions of the invention to decrease melanin production or to reduce skin pigmentation. Progesterone may be obtained from a variety of sources, e.g., Sigma (St. Louis, Mo.).

Alternatively, hydrophobic amines may be utilized in the methods and compositions of the invention. By the term "hydrophobic amine" is meant a compound having structure comprising a hydrophobic ring structure with a hydrophilic side chain containing a cationic amine functional group. Preferred hydrophobic amines include phenothiazines and tricyclic antidepressants. Particularly preferred phenothiazines include trifluoperazine, chlorpromazine, prochlorperazine, triflupromazine, promazine, thioridazine, mesoridaine, piperacetazine, perphenazine, fluphenazine, acetophenazine, and thiethylperazine. (Sigma, St. Louis, Mo.). Tricyclic antidepressants are other preferred hydrophobic amines that can be utilized in the methods and compositions of the invention. Particularly preferred tricyclic antidepressants include imipramine, nortriptyline, protriptyline, trimipramine, and doxepin (Sigma, St. Louis, Mo.).

Another compound useful in the methods and compositions of the invention is sphingosine, which is commercially available from, e.g., Sigma (St. Louis, Mo.).

Antagonists of a late endosomal/lysosomal trafficking protein are also useful in the methods and compositions of the invention to decrease melanin production or to reduce skin pigmentation. By the phrase "antagonist of a late endosomal/lysosomal trafficking protein" is meant an agent that interferes with or reduces the activity of a protein involved directly or indirectly with late endosomal/lysosomal cholesterol trafficking and that results in an alteration in this trafficking. By way of a non-limiting example, the agent that alters late endosomal/lysosomal trafficking may be a small organic molecule, or a protein, or a polysaccharide, etc.

By way of a non-limiting example, an antagonist of late endosomal/lysosomal trafficking may be a protein, for example, an antibody, that binds exclusively to a trafficking protein, proteolipid, proteoglycan, etc. (see Kobayashi et al. (1999) *Nature Cell Biol.* 1:113-116, which discloses an antibody that specifically binds phospholipid lysobiphosphatidic add as an antagonist to cholesterol trafficking).

The production of antibodies against specific antigenic determinants is well known in the art and is specifically described in *Current Protocols in Immunology*, Coligan et al. eds., (2000) John Wiley & Sons, New York, N.Y., and in Harlow & Lane, *Antibodies: A Laboratory Manual* (1988) Cold Spring Harbor Press, Cold Spring Harbor, N.Y.

The invention also provides compounds useful to decrease melanin production or to reduce skin pigmentation of the formula

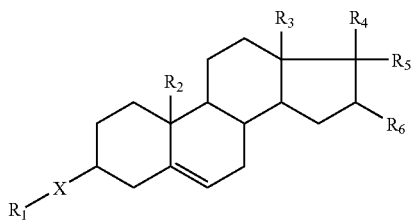

wherein X and $R_1$-$R_6$ are as described supra. Specific compounds of formula (I) include

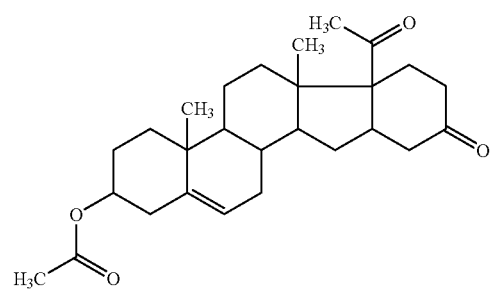

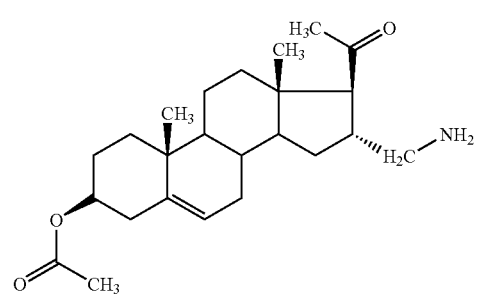

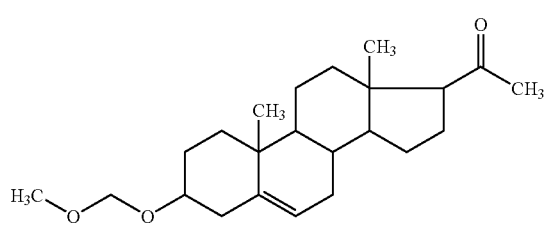

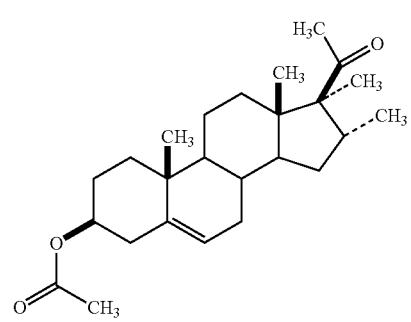

-continued

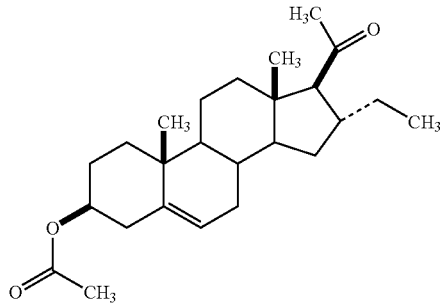

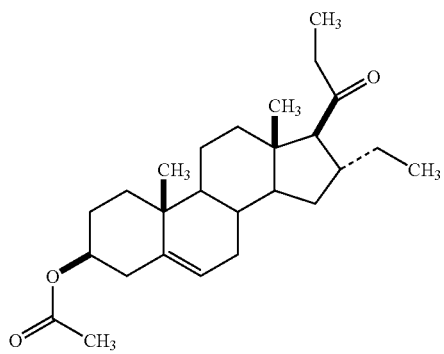

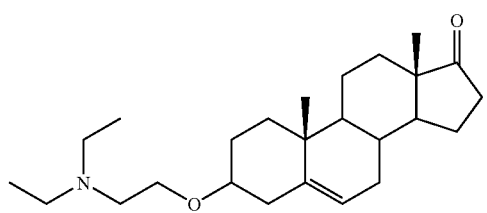

and any pharmaceutically acceptable salts or solvates thereof.

2.3 Rational Drug Design

Compounds identified by the methods of the invention or compounds disclosed herein may serve as the basis for molecular modeling techniques for the design of chemical analogs that are more effective. For example, chemical analogs of imipramine, or any of the other preferred compounds listed above, can be created using these or other modeling techniques. Examples of molecular modeling systems are the CHARM (Polygen Corporation, Waltham, Mass.) and QUANTA (Molecular Simulations Inc., San Diego, Calif.) programs. CHARM performs the energy minimization and molecular dynamics functions. QUANTA performs the construction, graphic modeling and analysis of molecular structure. QUANTA allows interactive construction, modification, visualization, and analysis of the behavior of molecules with each other.

For example, once a compound that affects or mimics P protein function and/or alters or inhibits late endosomal trafficking is identified, the compound can be used to generate a hypothesis. Such a hypothesis can be generated from any one of the preferred compounds of the present invention using, e.g., the program, Catalyst (Molecular Simulations Inc., San Diego, Calif.). Furthermore, Catalyst can use the hypothesis to search proprietary databases such as, for example, the Cambridge small molecule database (Cambridge, England), as well as other databases or compound libraries, e.g., those cited above, to identify additional examples of the compounds of the present invention.

Compounds of the present invention can further be used to design more effective analogs using modeling packages such as Ludi, Insight II, $C^2$-Minimizer and Affinity (Molecular Simulations Inc., San Diego, Calif.). A particularly preferred modeling package is MacroModel (Columbia University, New York, N.Y.).

The compounds of the present invention can further be used as the basis for developing a rational combinatorial library. Such a library can also be screened to identify more effective compounds. While the nature of the combinatorial library is dependent on various factors such as the particular compound chosen from the preferred compounds of the present invention to form the basis of the library, as well as the desire to synthesize the library using a resin, it will be recognized that the compounds of the present invention provide requisite data suitable for combinatorial design programs such as $C^2$-QSAR (Molecular Simulations Inc., San Diego, Calif.).

3 Methods of Inhibiting or Inducing Melanogenesis 3.1 Methods of Inhibiting Melanogenesis by Increasing or Mimicking P Protein Function Compounds that affect or mimic the function of P protein can be used to treat animals or, preferably, humans that have diseases, conditions, or disorders caused by the production or overproduction of melanin. Such diseases, conditions, or disorders include those that can be characterized by discolorations of the skin or hair such as, for example, hyperpigmentation caused by inflammation or from diseases such as melasma, or brown spots such as "café au lait" macules. Alternatively, a subject may wish to lighten the color of his or her hair or skin. Compounds that increase the function of P protein or that mimic the function of P protein can be used to treat animals or, preferably, humans that have diseases, conditions, or disorders caused by the underproduction of melanin such as, for example, post-inflammatory hypopigmentation, pityriasis alba, and certain forms of albinism such as, for example, OCA II albinism. Additionally, such compounds can be used to darken the color of one's hair or skin. For the purposes of this application, the terms "treatment", "therapeutic use", and "medicinal use" shall refer to any and all uses of the compositions of the invention which remedy a disease state or one or more symptoms, or otherwise prevent, hinder, retard, or reverse the progression of disease or one or more other undesirable symptoms in any way whatsoever.

3.2 Methods of Inhibiting Melanogenesis by Altering or Inhibiting Late Endosomal/lysosomal Trafficking The invention further provides methods and pharmaceutical compositions for inhibiting skin pigmentation comprising the use of agents that modify late endosomal/lysosomal trafficking. These methods and pharmaceutical compositions are useful for decreasing and/or inhibiting melanin production and, therefore, for reducing skin pigmentation. These agents may be used singly, in combination with one another, or in combination with other drugs that inhibit pigmentation. By way of a non-limiting example, other drugs that inhibit pigmentation include agents such as tyrosinase inhibitors. Preferably, the methods and compositions of the invention are for application to a vertebrate, more particularly to a mammal, and most preferably to a human.

Several pharmacological agents are known to inhibit or alter late endosomal/lysosomal trafficking. Hydrophobic amines, such as U18666A, progesterone, and sphingosine inhibit cholesterol movement from the PM to the ER, from the late endosome/lysosome to the ER, and from the late endosome/lysosome to the PM (Liscum et al. supra). These agents serve as a pharmacological model for the defective NPC1 protein (Lange et al (1998) *J. Biol. Chem.* 273:18915-22; Roff et al. (1991) *Dev. Neurosci.* 13:315-19). Furthermore, trafficking of the NPC1 protein itself is altered by U18666A, shifting the protein from late endosomes to the trans-Golgi network and lysosomes (Higgins et al. (1999) *Mol. Gen. Metab.* 68:1-13). U18666A has also been shown to alter the trafficking of CD63/lamp3, a protein normally associated with the internal membranes of multivesicular-multilamellar late endosomes and IGF2/MPR normally associated with the trans-Golgi network (Kobayashi et al. (2000) *Mol. Biol. Cell.* 11:1829-43; Kobayashi et al. (1999) *Nat. Cell Biol.* 1:113-118). The exact mechanism by which these agents alter late endosomal/lysosomal trafficking is not yet understood.

The invention takes advantage of the discovery that the inhibition of late endosomal/lysosomal trafficking results in a decrease in melanin production in melanocytes. Accordingly, in one aspect, the invention provides a method of decreasing melanin production in a melanocyte, comprising contacting the melanocyte with a pharmaceutically effective amount of a compound that effects an alteration in late endosomal/lysosomal trafficking in the melanocyte. The resulting alteration in late endosomal/lysosomal trafficking brings about a decrease in melanin production in the melanocyte.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent.

By the phrase "decrease in melanin production" is meant a detectable lowering of the amount of melanin synthesized de novo by a melanocyte exposed to a compound that alters late endosomal/lysosomal trafficking, as compared with the amount of melanin synthesized de novo by a control, untreated melanocyte. The term "lowering" preferably refers to about 10% to about 100% decrease in the amount of melanin synthesized de novo. More preferably, the term "lowering" refers to about a 25% to about a 100% decrease in the amount of melanin synthesized de novo. Most preferably, the term "lowering" refers to about a 50% to about a 100% decrease in the amount of melanin synthesized de novo.

The term "late endosomal/lysosomal trafficking" is used herein to refer to the movement of proteins, lipids, or other compounds between different cellular compartments. These locations include the movement of such compounds from the late endosome to the lysosome, from the lysosome to the late endosome, from the late endosome or lysosome to the trans Golgi network, and from the trans Golgi network to the late endosome or lsysome.

An alteration in late endosomal/lysosomal trafficking may be effected by contacting the melanocyte with a compound such as progesterone, a hydrophobic amine, sphingosine, an antagonist of late endosomal/lysosomal trafficking, or any of the compounds of the formulae (I)-(VIII) as defined supra.

Compounds of generic formula (I) are disclosed and may be synthesized following procedures detailed in WO00/58549 and U.S. Pat. Nos. 5,232,917, 3,210,386, 3,389,051, and 2,794,815.

As one skilled in the art would know in view of this disclosure, the compounds used in the methods of the present invention may be used alone or in combination with each other. Moreover, the methods of the invention also include the additional use of other compounds known in the art to affect melanin synthesis such as tyrosinase inhibitors. Such inhibitors are known to those skilled in the art and include various derivatives of resorcinol, hydroquinone, kojic acid, melamine, and various types of plant extracts, among others.

Thus, the invention relates both to methods of modulating the pigmentation of skin in which the active compound used according to the invention, or a pharmaceutically acceptable salt thereof, and one or more of the other active ingredients referred to above are administered together, as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

For example, any of the compounds used according to a skin-lightening method of the invention may be used in combination with a tyrosinase inhibitor or other skin-whitening agent as currently known in the art or to be developed in the future, including any one or more of those agents described in the following patent publications: U.S. Pat. No. 4,278,656 to Nagai et al, issued Jul. 14, 1981; U.S. Pat. No. 4,369,174 to Nagai et al., issued Jan. 18, 1983; U.S. Pat. No. 4,959,393 to Torihara et al., issued Sep. 25, 1990; U.S. Pat. No. 5,580,549 to Fukuda et al., issued Dec. 3, 1996; U.S. Pat. No. 6,123,959 to Jones et al., issued Sep. 26, 2000; U.S. Pat. No. 6,132,740 to Hu, issued Oct. 17, 2000; U.S. Pat. No. 6,159,482 to Tuloup et al., issued Dec. 12, 2000; WO 99/32077 by L'Oreal, published Jul. 1, 1999; WO 99/64025 by Fytokem Prod. Inc., published Dec. 16, 1999; WO 00/56702 by Pfizer Inc., published Sep. 28, 2000; WO 00/76473 by Shiseido Co. Ltd., published Dec. 12, 2000; EP 997140 by L'Oreal SA, published May 3, 2000; JP 5221846 by Kunimasa Tomoji, published Aug. 31, 1993; JP 7242687 by Shiseido Co. Ltd., published Sep. 19, 1995; JP 7324023 by Itogawa H, published Dec. 12, 1995; JP 8012552 by Shiseido Co. Ltd., published Jan. 16, 1996; JP 8012554 by Shiseido Co. Ltd., published Jan. 16, 1996; JP 8012557 by Shiseido Co. Ltd., published Jan. 16, 1996; JP 8012560 by Shiseido Co. Ltd., published Jan. 16, 1996; JP 8012561 by Shiseido Co. Ltd., published Jan. 16, 1996; JP 8134090 by Fujisawa, published May 28, 1996; JP 8168378 by Kirinjo KK, published Jul. 2, 1996; JP 8277225 by Kansai Koso KK, published Oct. 22, 1996; JP 9002967 by Sanji Shoji KK, published Jan. 7, 1997; JP 9295927 by Yagi Akira, published Nov. 18, 1997; JP 10072330 by Kansai Kouso, published Mar. 17, 1998; JP 10081626 by Kamiyama KK, published Mar. 31, 1998; JP 10101543 by Kansai Kouso KK, published Apr. 21, 1998; JP 11071231 by Maruzen Pharm., published Mar. 16, 1999; JP 11079934 by Kyodo Nyugyo, published Mar. 23, 1999; JP 11246347 by Shiseido Co. Ltd., published Sep. 14, 1999; JP 11246344 by Shiseido Co. Ltd., published Sep. 14, 1999; JP 2000-080023 by Kanebo Ltd., published Mar. 21, 2000; JP 2000-095663 by Kose KK, published Apr. 4, 2000; JP 2000-159681 by Hai Tai Confectionary Co. Ltd., published Jun. 13, 2000; JP 2000-247907 by Kanebo Ltd., published Sep. 12, 2000; JP-9002967 by Sanki Shoji KK, published Jan. 7, 1997; JP-7206753 by Nikken Food KK, published Aug. 8, 1995; JP-5320025 by Kunimasa T, published Dec. 3, 1993; and JP-59157009 by Yakurigaku Chuou KE, published Sep. 6, 1984; among others; which patent publications are incorporated herein by reference.

Any of the compounds used according to a skin-darkening method of the invention may be used in combination with "sunless tanning" agents as currently known in the art or to be developed in the future, including any one or more of those agents described in the following patent publications: U.S. Pat. No. 5,591,423 to Fuller, issued Jan. 7, 1997; U.S. Pat. No. 5,628,987 to Fuller, issued May 13, 1997; EP 993826 by L'Oreal, published Apr. 19, 2000; and WO 99/56740 by Galderma Res. & Dev., published Nov. 11, 1999; among others; which patent publications are incorporated herein by reference.

Non-limiting examples of compounds that cause an alteration in late endosomal/lysosomal trafficking include U18666A and its derivatives (e.g., formulae II-VII), either alone or in combination. Particular derivatives have been described above. Progesterone is another compound useful in the methods and compositions of the invention to decrease melanin production or to reduce skin pigmentation.

Alternatively, hydrophobic amines may be utilized in the methods and compositions of the invention. By the term "hydrophobic amine" is meant a compound having structure comprising a hydrophobic ring structure with a hydrophilic side chain containing a cationic amine functional group. Preferred hydrophobic amines include phenothiazines and tricyclic antidepressants. Particularly preferred phenothiazines include trifluoperazine, chlorpromazine, prochlorperazine, triflupromazine, promazine, thioridazine, mesoridaine, piperacetazine, perphenazine, fluphenazine, acetophenazine, and thiethylperazine, as described above. Tricyclic antidepressants are other preferred hydrophobic amines to be utilized in the methods and compositions of the invention. Particularly preferred tricyclic antidepressants are imipramine, nortriptyline, protriptyline, trimipramine, and doxepin, as described above. Another compound useful in the methods and compositions of the invention is sphingosine.

In another aspect, the invention provides a method of reducing skin pigmentation. In this method the skin is contacted with a pharmaceutically effective amount of a compound that effects an alteration in late endosomal/lysosomal trafficking, wherein an alteration in late endosomal/lysosomal trafficking results in a reduction of skin pigmentation.

By the phrase "reducing skin pigmentation" is meant a detectable decrease in the amount of melanin in the skin, preferably causing a lightening of the skin as a result of a lowering of the amount of melanin synthesized de nova. The term "lowering" preferably refers to a about 10% to about a 100% decrease in the amount of melanin synthesized de novo. More preferably, the term "lowering" refers to about a 25% to about a 100% decrease in the amount of melanin synthesized de novo. Most preferably, the term "lowering" refers to about a 50 to about a 100% decrease in the amount of melanin synthesized de nova. This lowering of melanin synthesized de novo is preferably visually distinguishable to the naked eye, i.e., would not require the aid of a microscope or other such means to detect its occurrence.

The invention also provides for a reduction in skin pigmentation by contacting the skin topically with an effective amount of a compound that alters late endosomal/lysosomal trafficking in the skin. Useful compounds for these methods of the invention include those disclosed above.

4 Pharmaceutical Applications

For pharmaceutical uses, it is preferred that the compound that affects or mimics P protein function or that inhibits late endosomal/lysosomal trafficking is part of a pharmaceutical composition. Pharmaceutical compositions, comprising an effective amount of such a compound in a pharmaceutically acceptable carrier, can be administered to a patient, person, or animal having a disease, disorder, or condition which is of a type that produces, or overproduces, melanin.

The amount of compound which will be effective in the treatment of a particular disease, disorder, or condition will depend on the nature of the disease, disorder, or condition, and can be determined by standard clinical techniques. Where possible, it is desirable to determine in vitro the cytotoxicity of the compound to the tissue type to be treated, and then in a useful animal model system prior to testing and use in humans.

The compound can be administered for the reduction or increase of melanin synthesis by any means that results in contact of the active agent with its site of action in the body of a mammal. The compounds can be administered by any conventional means available for use in conjunction with pharmaceuticals, either as individual therapeutic agents or in a combination of therapeutic agents. Each can be administered alone, but is preferably administered with a pharmaceutical carrier selected on the basis of the chosen route of administration and standard pharmaceutical practice. The pharmaceutical compositions of the invention can be adapted for oral, parenteral, rectal, and preferably topical, administration, and can be in unit dosage form, in a manner well known to those skilled in the pharmaceutical art. Parenteral administration includes but is not limited to, injection subcutaneously, intravenously, intraperitoneally or intramuscularly. However, topical application is preferred.

5 Cosmetic Applications

In addition to pharmaceutical uses, the methods of the current invention are useful for cosmetic purposes. Cosmetic applications for methods of the present invention include the topical application of compositions containing one or more compounds to enhance or otherwise alter the visual appearance of skin or hair. Occurrences in the skin or hair of noticeable but undesired pigmentation as a result of melanin production, overproduction or underproduction can be treated using the methods of the present invention.

6 Endpoints and Dosages

An effective dosage and treatment protocol can be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can extrapolate doses for efficacy and avoidance of toxicity to other species, including humans.

Before human studies of efficacy are undertaken, Phase I clinical studies in normal subjects can help establish safe doses. Numerous factors can be taken into consideration by a clinician when determining an optimal dosage for a given subject. Primary among these is the toxicity and half-life of the chosen compound that affects or mimics P protein function or that inhibits late endosomal/lysosomal trafficking. Additional factors include the size of the patient, the age of the patient, the general condition of the patient, the particular disease, condition, or disorder being treated, the severity of the disease, condition, or disorder being treated, the presence of other drugs in the patient, the effect desired, and the like. The trial dosages would be chosen after consideration of the results of animal studies and the clinical literature.

One of ordinary skill in the art will appreciate that the endpoint chosen in a particular case will vary according to the disease, condition, or disorder being treated, the outcome desired by the patient, subject, or treating physician, and other factors. Where the composition is being used to lighten or darken skin color such as, for example, to reverse hyperpigmentation caused by, for example, inflammation or diseases such as melasma, or to lighten or darken hair color, any one of a number of endpoints can be chosen. For example, endpoints can be defined subjectively such as, for example, when the subject is simply "satisfied" with the results of the treatment. For pharmacological compositions, the endpoint can be determined by the patient's, or the treating physicians, satisfaction with the results of the treatment. Alternatively, endpoints can be defined objectively. For example, the patients or subjects skin or hair in the treated area can be compared to a color chart. Treatment is terminated when the color of the skin or hair in the treated area is similar in appearance to a color on the chart. Alternatively, the reflectance of the treated skin or hair can be measured, and treatment can be terminated when the treated skin or hair attains a specified reflectance. Alternatively, the melanin content of the treated hair or skin can be measured. Treatment can be terminated when the melanin content of the treated hair or skin reaches a specified value. Melanin content can be determined in any way known to the art, including by histological methods, with or without enhancement by stains for melanin.

7 Methods of Administration

The compound that affects or mimics P protein function or that inhibits late endosomal/lysosomal trafficking or that inhibits ATPases (i.e., the active agent or ingredient) can be administered topically, e.g., as patches, ointments, creams, gels, lotions, solutions, or transdermal administration. The compound can also be administered orally in solid or semisolid dosage forms, such as hard or soft-gelatin capsules, tablets, or powders, or in liquid dosage forms, such as elixirs, syrups, or suspensions. Additionally, the compound can also be administered parenterally, in sterile liquid dosage forms or in suppository form.

Because in vivo use is contemplated, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Useful pharmaceutical dosage forms for administration of compounds that affect or mimic P protein function or that inhibit late endosomal/lysosomal trafficking or that inhibit ATPases are described below.

The pharmaceutical compositions can be applied directly to the skin. Alternatively, they can be delivered by various transdermal drug delivery systems, such as transdermal patches as known in the art. For example, for topical administration, the active ingredient can be formulated in a solution, gel, lotion, ointment, cream, suspension, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos. Actual methods for preparing topical formulations are known or apparent to those skilled in the art, and are described in detail in *Remington's Pharmaceutical Sciences*, 1990 (supra); and *Pharmaceutical Dosage Forms and Drug Delivery Systems*, 6th ed., Williams & Wilkins (1995).

In order to enhance the percutaneous absorption of the active ingredients, one or more of a number of agents can be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

A topically applied composition of the invention contains a pharmaceutically effective agent that affects or mimics P protein function or that inhibits late endosomal/lysosomal trafficking or that inhibits ATPases as described herein, and those ingredients as are necessary for use as a carrier, such as an emulsion, a cream, an ointment, an ophthalmic ointment, an aqueous solution, a lotion or an aerosol. Non-limiting examples of such carriers are described in more detail below and may be found in International Patent Publication WO 00/62742, published Oct. 26, 2000, U.S. Pat. No. 5,691,380 to Mason et al., issued on Nov. 25, 1997 and U.S. Pat. No. 5,968,528 to Deckner et al., issued on Oct. 19, 1999, U.S. Pat. No. 4,139,619 to Chidsey, III, issued on Feb. 13, 1979 and U.S. Pat. No. 4,684,635 to Orentreich et al., issued on Aug. 4, 1987 which are incorporated herein by reference. Suitable pharmaceutical carriers are further described in *Remington's Pharmaceutical Sciences*, 17th ed., Mack Publishing Company, Easton, Pa. (1990) a standard reference text in this field.

The pharmaceutical compositions of the invention may also include optional components. Such optional components should be suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds of the invention. The *CTFA Cosmetic Ingredient Handbook*, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigents, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g. iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

In addition to the pharmaceutically effective amount of an agent disclosed herein, the topical compositions of the present invention also comprise a dermatologically acceptable carrier. The phrase "dermatologically acceptable carrier", as used herein, means that the carrier is suitable for topical application to the skin, i.e., keratinous tissue, has good aesthetic properties, is compatible with the active agents of the present invention and any other components, and will not cause any safety or toxicity concerns. A safe and effective amount of carrier is from about 50% to about 99.99%, preferably from about 80% to about 99.9%, more preferably from about 90% to about 98%, and most preferably from about 90% to about 95% of the composition.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an ophthalmic ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al. Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g. mineral, oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991;

U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic, acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, *McCutcheon's, Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued to Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued to Sep. 29, 1992; U.S. Pat. No. 5,151,210 to Steuri et al. issued to Sep. 29, 1992; U.S. Pat. Nos. 5,120,532; 4,387,090; 3,155,591; 3,929,678; 3,959,461; *McCutcheon's, Detergents & Emulsifiers* (North American edition 1979) M.C. Publishing Co.; and Schwartz, et al., *Surface Active Agents, Their Chemistry and Technology*, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, *Cosmetics, Science and Technology*, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72-73 (1972), incorporated herein by reference, and/or an emollient. For example, an ointment may comprise from about 2% to about 10% of an emollient; from about 0.1% to about 2% of a thickening agent; and a pharmaceutically effective amount of an agent described herein.

By way of non-limiting example, 1000 g of topical cream is prepared from the following types and amounts of ingredients: a pharmaceutically effective amount of an agent disclosed herein, tegacid regular (150 g) (a self-emulsifying glyceryl monostearate from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 gm. The tegacid and spermaceti are melted together at a temperature of 70-80° C. The methylparaben is dissolved in about 500 g. of water and the propylene glycol, polysorbate 80, and 6-amino-1,2-dihydro-1-hydroxy-2-imino-4-piperidinopyrimidine free base are added in turn, maintaining a temperature of 75-80° C. The methylparaben mixture is added slowly to the tegacid and spermaceti melt, with constant stirring. The addition is continued for at least 30 minutes with additional stirring until the temperature has dropped to 40-45° C. Finally, sufficient water is added to bring the final weight to 1000 g. and the preparation stirred to maintain homogeneity until cooled and congealed.

By way of non-limiting example, 1000 g of a topical ointment is prepared from the following types and amounts of ingredients: a pharmaceutically effective amount of an agent disclosed herein, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The pharmaceutically effective amount of an agent disclosed herein, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment, e.g., an ophthalmic ointment, containing a pharmaceutically effective amount of an agent disclosed herein is prepared from the following types and amounts of ingredients: a pharmaceutically effective amount of an agent disclosed herein, light liquid petrolatum (250 g), wool fat (200 g), and enough white petrolatum to reach 1000 g. Briefly, the pharmaceutically effective amount of an agent disclosed herein is finely divided and added to the light liquid petrolatum. The wool fat and white petrolatum are melted together, strained, and the temperature adjusted to 45-50° C. The liquid petrolatum slurry is added, and the ointment stirred until congealed.

By way of non-limiting example, 1000 ml of an aqueous solution containing a pharmaceutically effective amount of an agent disclosed herein is prepared from the following types and amounts of ingredients: a pharmaceutically effective amount of an agent disclosed herein, polyethylene glycol 4000 (120 g) myristyl-gamma-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a pharmaceutically effective amount of an agent disclosed herein is prepared from the following types and amounts of ingredients: a pharmaceutically effective amount of an agent disclosed herein, N-methyl pyrolidone (40 g), and enough propylene glycol to reach 1000 g.

By way of non-limiting example, an aerosol containing a pharmaceutically effective amount of an agent disclosed herein is prepared from the following types and amounts of materials: a pharmaceutically effective amount of an agent disclosed herein, absolute alcohol (4.37 g), Dichlorodifluoroethane (1.43 g) and dichlorotetrafluoroethane (5.70 g). Briefly, the pharmaceutically effective amount of an agent disclosed herein is dissolved in the absolute alcohol and the resulting solution filtered to remove particles and lint. This solution is chilled to about minus 30° C. Then, to this is added the chilled mixture of dichlorodifluoromethane and dichlorotetrafluoroethane.

For oral administration, Gelatin capsules or liquid-filled soft gelatin capsules can contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5-15% polysorbate 80 or lecithin, suitable stabilizing agents and, if necessary, buffer substances. Antioxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

As will be understood by those in the art, the compositions and pharmaceutical compositions of the invention may be provided in the form of a kit. Kits of the invention comprise one or more specific compositions and/or pharmaceutical compositions of the invention that mimic and/or affect P protein function, inhibit late endosomal/lysosomal trafficking, or inhibit ATPases. Optionally, the kit further contains printed instructions as a label or package insert directing the use of such reagents to modulate skin pigmentation, i.e., to either lighten or darken skin as appropriate to the particular included composition. These compounds are provided in a container designed to prevent contamination, minimize evaporation or drying of the composition, etc. The compounds may or may not be provided in a preset unit dose or usage amount.

The invention having been described, the following examples are offered by way of illustration and not limitation.

EXAMPLES

Example 1

Targeting Function Screen

In this example, the effect of P protein on cellular targeting of tyrosinase was investigated. This function was then exploited in a screen for compounds that inhibit the activity of P protein.

Melan-a cells (a/a, P/P), an immortalized melanocyte line derived from C57BLI6J mice wild type at the p locus (Bennett et al., 1987, *Int. J. Cancer* 39:414-418), were maintained in culture in Dulbecco's modification of Eagle's medium (DME). Melan-p1 melanocytes from mice lacking all p gene transcripts due to the presence of overlapping deletions (a/a, $p^{cp}/p^{25H}$) (Sviderskaya et al., 1997, *J. Invest. Dermatol.* 108: 30-34) were maintained in Harn's F10 medium. Both media were supplemented with 10% fetal calf serum, 5% sodium pyruvate, 5% glutamate, 5 units/ml penicillin, 5 μg/ml streptomycin, 1% non-essential amino acids and 200 nM 12-O-tetradecanoyl phorbol 13-acetate. In addition, 200 pM cholera toxin was added to the melan-p1 cells.

Cells were maintained in the appropriate media, which was then replaced with tyrosine deficient DME medium (DME-D) supplemented with either 0.03 mM tyrosine for low tyrosine conditions or 0.3 mM tyrosine for high tyrosine conditions (Bennett, D. C. et al., 1987, *Int. J. Cancer* 39:414-418), (Sviderskaya et al., *J. Invest Dermatol.* 108:30-34). Aliquots of culture medium were withdrawn, dialyzed against 0.1 M sodium phosphate buffer, pH 6.8, and analyzed for tyrosinase activity using a radiometric tyrosine hydroxylase assay (Orlow, S. J. et al., 1990, *J. Invest. Dermatol.* 94:461-64).

For treatment with test compounds, cultured melan-a melanocytes were incubated for 48 hours in the presence of low tyrosine in the medium as above but in the presence of benztropine (10 micromolar final concentration), or imipramine (10 micromolar final concentration), or nitroquipazine, (30 micromolar final concentration), or left untreated. Incubation media were assayed for tyrosinase activity, as above.

Increasing tyrosinase activity in the media removed from melan-p cell cultures grown in the presence of low tyrosine indicates that these cells secrete relatively large amounts of tyrosinase into their incubation media (FIG. 1). By contrast, melan-a cells, which represent wild type melanocytes, secrete significantly less tyrosinase into the media (FIG. 1). While culture in the presence of excess tyrosine had little effect on melan-a cells, the amount of enzyme secreted by melan-p1 cells was reduced. As predicted above, tyrosine appears to partially correct the misrouting of tyrosinase in melan-p1 cells.

Treatment with benztropine did not alter the levels of tyrosinase activity secreted to the incubation medium of melan-a cells (FIG. 2). Treatment with either imipramine or nitroquipazine significantly increased the levels of tyrosinase activity found in the cells' incubation medium (FIG. 2).

Melan-a cells are melanocytes derived from wild type mice. They have fully functional P protein and tyrosinase, and produce melanin. Melan-p cells, however, are derived from p-null mice having a deletion of the entire p gene coding sequence. Thus, they produce no P protein. Consequently, melan-p cells have lower tyrosinase activity and make less melanin than melan-a cells.

This example, which can be performed with any type of melanogenic cell, demonstrates that melanocytes lacking P protein function secrete significantly more tyrosinase into their growth or incubation medium than do melanocytes with normal P protein function. This result is obtained either when the cells are genetically altered to reduce or eliminate P protein function, as in melan-p cells (FIG. 1), or when the cells are treated with a compound that inhibits P protein function, such as imipramine (FIG. 2B).

Example 2

Tyrosinase Activity Screen

In this example, the effect of P protein on the measurable enzymatic activity of tyrosinase from cells genetically engineered to express tyrosinase was investigated. Any melanogenic cell type that expresses both P protein and tyrosinase, or any cell type made to express both P protein and tyrosinase, can be substituted. This function was then exploited in a screen for compounds that inhibit the function of P protein.

Cultured melan-a melanocytes, as described above in Example 1, were incubated for 48 hours in the presence of benztropine (10 micromolar final concentration), or imipramine (10 micromolar final concentration), or nitroquipazine (30 micromolar final concentration), or left untreated. Cells were washed and extracted with 50 mM Tris-HCl (pH 7.4), 2 mM EDTA, 150 mM NaCl and 1% Triton X-100. Cell extracts were analyzed for tyrosinase activity using a radiometric tyrosine hydroxylase assay (Orlow, S. J. et al., 1990, supra).

Expression vectors were constructed to express P protein and tyrosinase genes in cultured cells. Specifically, the coding sequence for tyrosinase was removed as a HindIII-EcoRI fragment from clone TYBS (Yokohama et al., 1990, *Nucl. Acids. Res.* 18:7293-7298) and cloned into the HindIII/EcoRI sites of pcDNA I/lamp (Invitrogen, Calif.). Coding sequence for the P protein was removed as a BamHI-EcoRI fragment from MC2701 (Gardner et al., 1992, supra) and cloned into the BamHI/EcoRV sites of pcDNA3 and pcDNA3.1/V5/His-TOPO (Invitrogen, Calif.). COS cells were transfected with the pcDNA1-based plasmids and FuGENE™ 6 (Roche Molecular Biochemicals, Indianapolis, Ind.) as transfection agents for 48 hours. Cells were transformed with: (i) the vector alone; (ii) the vector carrying a tyrosinase-encoding gene; (iii) the vector carrying a P protein-encoding gene; or (iv) vectors carrying a tyrosinase-encoding gene and a P protein-encoding gene. Transformed cells were washed and extracted as above. Tyrosinase activity was then measured as above. Tyrosinase assays were performed on 60 micrograms of cell protein.

COS cells transfected with a vector carrying a tyrosinase-encoding gene, or with vectors carrying a tyrosinase-encoding gene and a P protein-encoding gene as above, were treated with benztropine, or imipramine, or nitroquipazine, or left untreated, as above, and cell extracts were then prepared as above. The tyrosinase activity of cell extracts was determined as above.

Figure 2A:
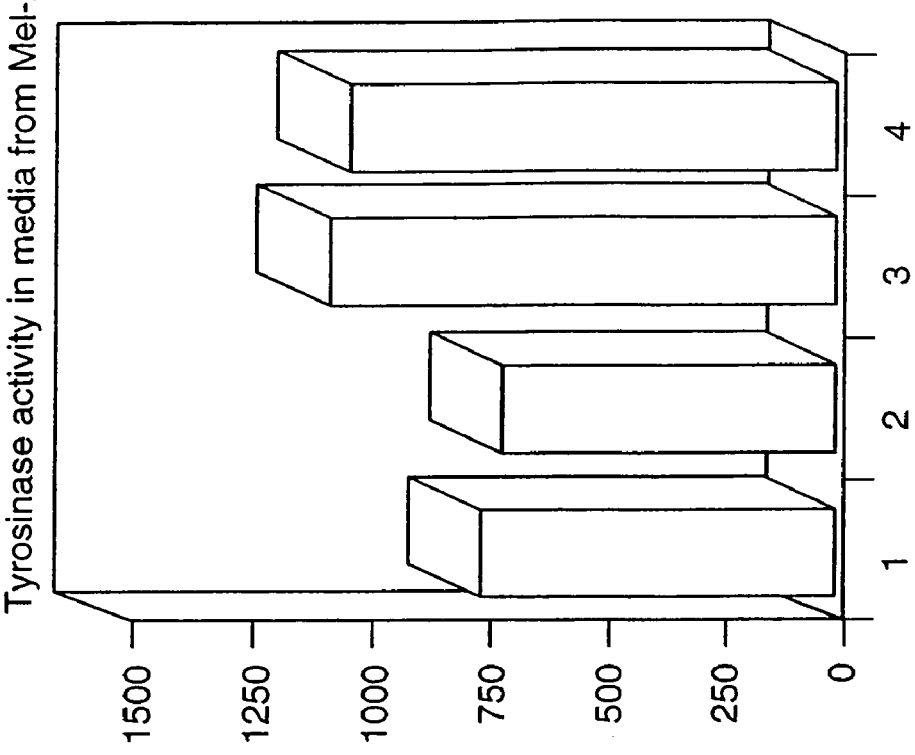
FIGS. 2A and 2B are graphic presentations of tyrosinase activity in cell extracts and media from melan-A cells. Cultured melan-a melanocytes were incubated for 48 hours in the presence of benztropine, imipramine, nitroquipazine, or left untreated. Incubation media or cell extracts were assayed for tyrosine hydroxylase activity, as in FIG. 1. Column 1, untreated melanocytes; Column 2, melanocytes treated with benztropine; column 3, melanocytes treated with 10,11-dihydro-n,n-dimethyl-5H-dibenz[b,f]azepine-5-propanamine (imipramine); Column 4, melanocytes treated with 6-nitro-2-(1-piperazinyl)-quinoline maleate (nitroquipazine).
Figure 2B:
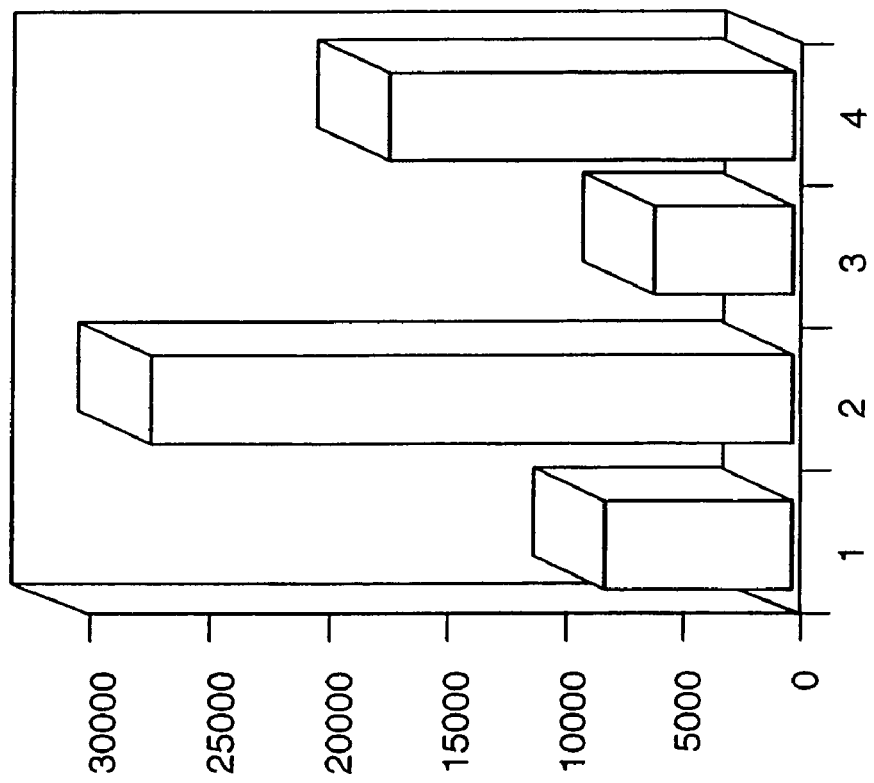

As shown in FIG. 2A, extracts from melan-a cells treated with benztropine or nitroquipazine had greater tyrosinase activities than untreated cells. Extracts from cells treated with imipramine had less tyrosinase activity than untreated cells.

Figure 3:
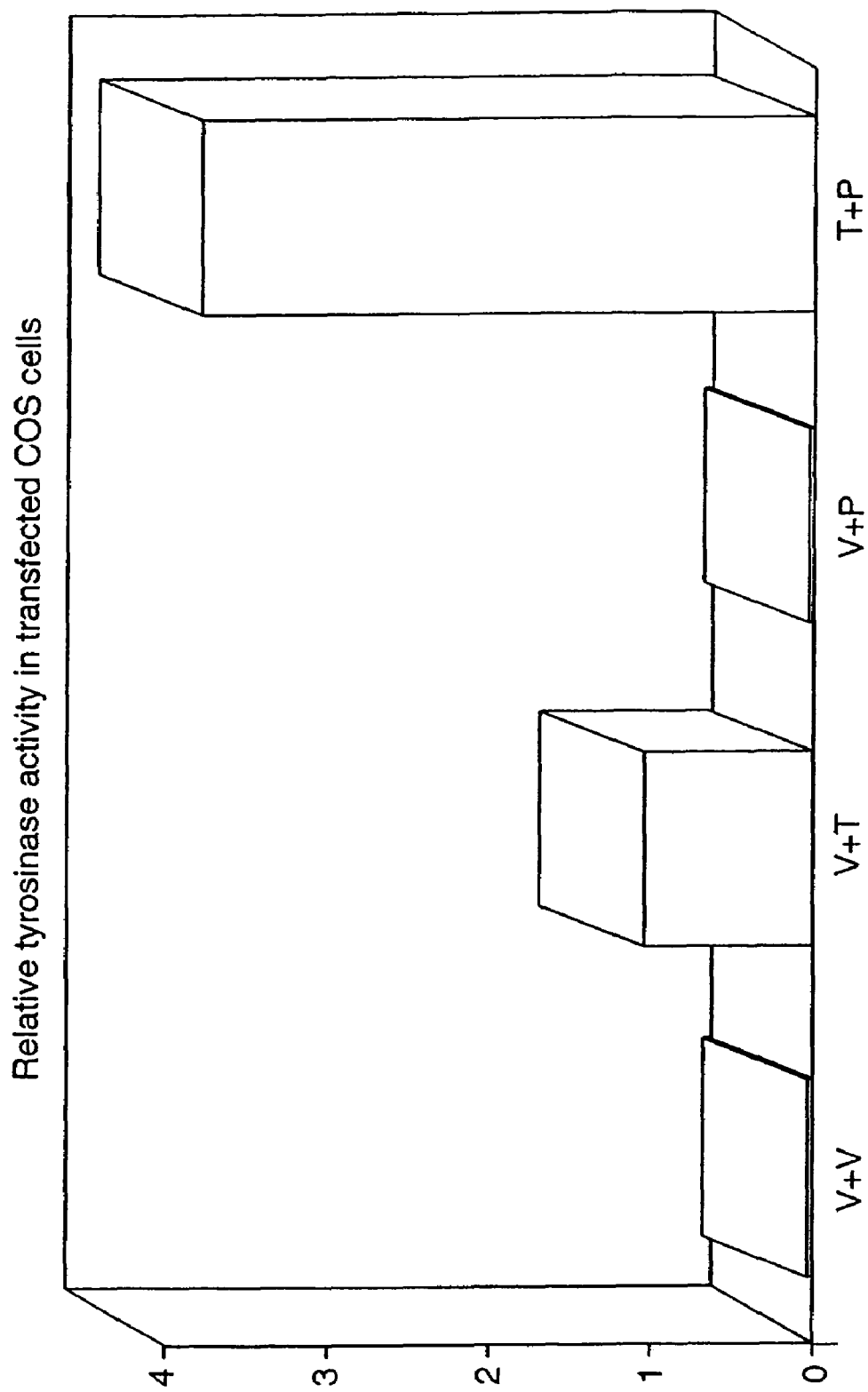
FIG. 3 is a graphic presentation of relative tyrosinase activity in transfected COS cells. COS cells were transfected with two doses of the vector alone (V+V), one dose of the vector alone and one dose of the vector carrying a tyrosinase-encoding gene (V+T), one dose of the vector alone and one dose of the vector carrying a P protein-encoding gene (V+P), or one dose each of the vectors carrying a tyrosinase-encoding gene and a P protein-encoding gene (T+P). Equal quantities of cell extract protein were assayed for tyrosine hydroxylase activity. Relative activities shown are calculated as the activity of the test sample divided by the activity of the V+T sample. The introduction of an expression plasmid carrying the tyrosinase gene (V+T) results in tyrosine hydroxylase activity in COS cells. This activity is the direct result of the tyrosinase-encoding plasmid, since transfection with the expression vector (V+V) alone does not generate any tyrosine hydroxylase activity. The tyrosine hydroxylase activity in cells carrying the tyrosinase-encoding plasmid can be increased almost 4-fold by co-transfection with the P gene expression plasmid (T+P). This increase is the result of an interaction between tyrosinase and P protein, since the introduction of P (V+P) without tyrosinase generates no tyrosine hydroxylase activity.

As shown in FIG. 3, extracts from COS cells transfected with the vector alone (V+V) or with the vector carrying the P protein-encoding gene (V+P) did not exhibit measurable tyrosinase activity. Extracts from cells transfected with the vector carrying the tyrosinase-encoding gene (V+T) had measurable tyrosinase activity, while extracts from cells transfected with the vectors carrying the tyrosinase-encoding gene and the P protein-encoding gene (T+P) had tyrosinase activity approximately four fold greater than the tyrosinase activity found in extracts of cells transfected with the vector carrying the tyrosinase-encoding gene alone (V+T).

Figure 4:
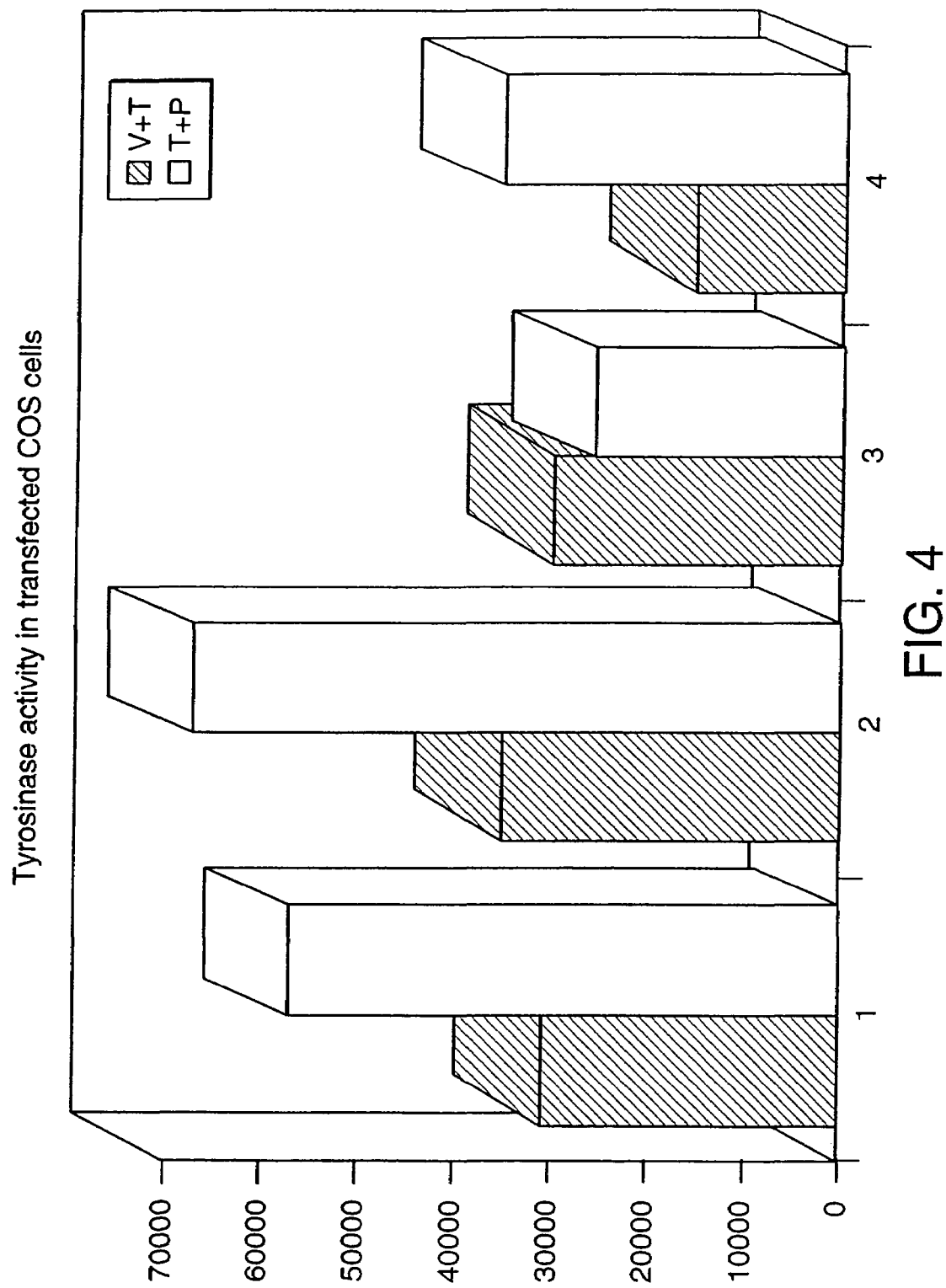
FIG. 4 is a graphic presentation of tyrosinase activity in transfected COS cells. COS cells transfected with a vector carrying a tyrosinase-encoding gene, or with a first vector carrying a tyrosinase-encoding gene and with a second vector carrying a P protein-encoding gene as in FIG. 3, were treated with benztropine, imipramine, nitroquipazine, or left untreated, as in FIG. 2. Cell extracts were prepared as in FIG. 3 The tyrosine hydroxylase activity of cell extracts was determined as in FIG. 1 as a measure of tyrosinase activity. Column 1, untreated transfectants; Column 2, transfectants treated with benztropine; Column 3, transfectants treated with imipramine; Column 4, transfectants treated with nitroquipazine. Tyrosine hydroxylase activity is measured in cpm [$^3$H]H$_2$O/60 micrograms protein/hr. Cells co-transfected with a tyrosinase-encoding gene and a P protein-encoding gene (T+P) show a higher tyrosine hydroxylase activity than cells transfected with a tyrosinase-encoding gene alone (V+T) (column 1). This effect is not altered by incubation of cells in the presence of benztropine (column 2) or nitroquipazine (column 4). The presence of imipramine, however, abolishes the effect of P protein while appearing to have little effect on the activity in the cells with tyrosinase alone (column 3).

FIG. 4 shows the separate effects of three compounds on P protein function. Nitroquipazine (4) caused extracts from tyrosinase-expressing COS cells to exhibit lower tyrosinase activity, regardless of whether the cells were expressing the P protein. Benztropine (2) did not have an appreciable effect on tyrosinase activity in these extracts. Imipramine (3) dramatically reduced the tyrosinase activity of cells expressing both P protein and tyrosinase, but had very little effect on cells expressing only tyrosinase.

This example illuminates the relationship between P protein function and tyrosinase activity in cell extracts. Melanocytes that express P protein can be made to mimic cells that lack P protein function through the use of compounds that inhibit P protein function. Melan-a cells are wild type for the P protein-encoding gene. Yet extracts taken from these cells after they are treated with imipramine have lower tyrosinase activity than untreated melan-a cells (FIG. 2). In contrast, extracts from cells treated with benztropine or nitroquipazine have higher tyrosinase activity than untreated cells (FIG. 2).

COS cells are derived from monkey kidney cells. Normally, they do not express tyrosinase or P protein. This example demonstrates that by transfecting COS cells with a tyrosinase-encoding gene and a P protein encoding gene, one can produce what might be considered an "artificial melanocyte." These cells express active tyrosinase and P protein (FIG. 3), and even produce melanin. Cotransfection of COS cells with both a tyrosinase-encoding gene and a P protein-encoding gene produces cells with approximately four times more tyrosinase activity than COS cells transfected with a tyrosinase-encoding gene alone (FIG. 3). This result demonstrates that P protein is expressed and active in these cells because the intracellular activity of tyrosinase was increased by P protein expression.

Extracts from COS cells that have been transformed with both a tyrosinase-encoding gene and a P protein-encoding gene and then treated with imipramine contained only about one third of the tyrosinase activity of similar cells not treated with imipramine (FIG. 4). The tyrosinase activity of COS cells that were transfected with only a tyrosinase-encoding gene and then treated with imipramine was not significantly different than the tyrosinase activity of extracts of similar cells not treated with imipramine (FIG. 4). These results indicate that imipramine reduces tyrosinase activity by inhibiting P protein function. By contrast, benztropine did not reduce the tyrosinase activity of extracts of transfected COS cells, whether or not they expressed P protein (FIG. 4). In addition, nitroquipazine reduced the tyrosinase activity of extracts of transfected COS cells, whether or not they expressed P protein (FIG. 4). This result indicates that nitroquipazine is not an inhibitor of P protein function.

Example 3

Secretion of Tyrosinase in Melan-p Cells Results from Proteolysis

Figure 5A:
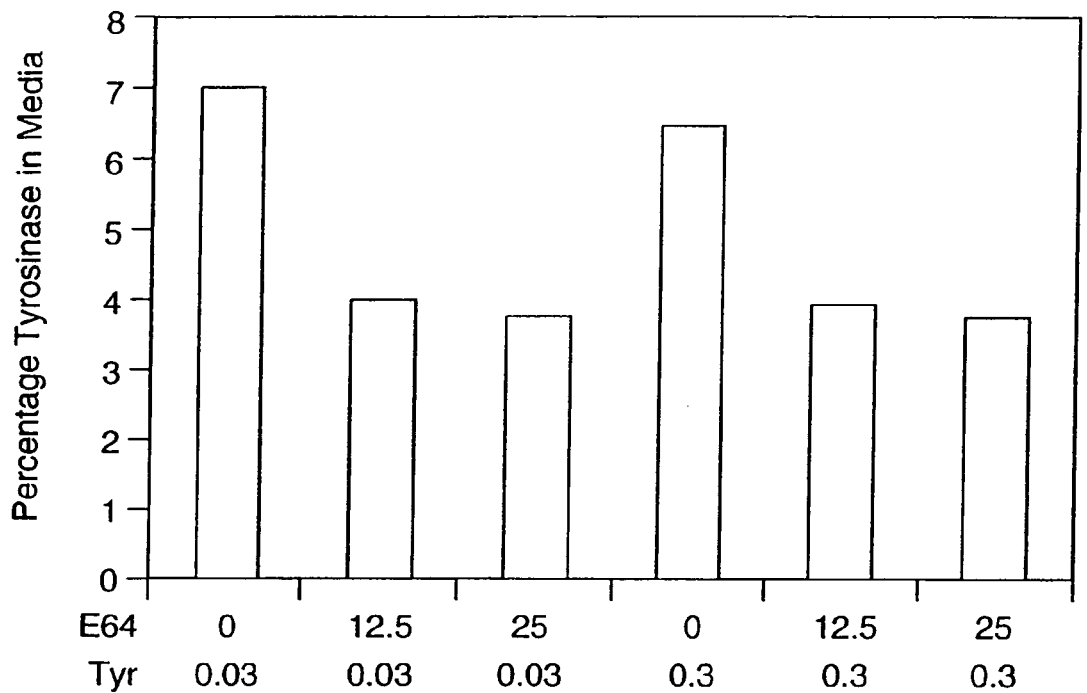
FIGS. 5A and 5B are graphic presentations demonstrating that the levels of secreted tyrosinase are elevated in melan-p1 and are reduced by inhibition of cysteinyl proteases. (A) Melan-p1 cells incubated in low (0.03 mM) tyrosine and high (0.3 mM) tyrosine (TYR) were treated for 48 hours with increasing concentrations of the protease inhibitor E64 (µM). The tyrosinase activity in the media is expressed as a percentage of total activity in the extract and medium. (B) The concentration of melanin was determined by solubilizing the cell pellet and measuring the absorbance at 470 nm.
Figure 5B:
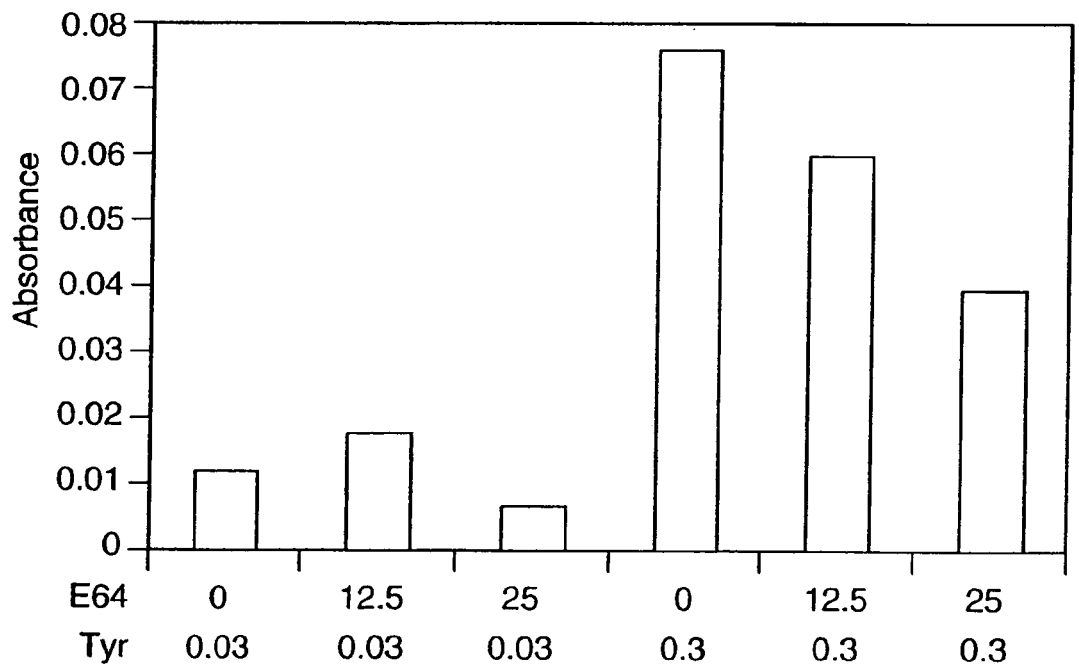

While we observed activity of tyrosinase in the medium, Potterf et al. (1998, *Exp. Cell Res.* 244:319-326) did not detect tyrosinase protein in the medium using αPEP7. Tyrosinase is a type I membrane protein anchored in the membrane, and it is thus likely that proteolysis, which leads to the clipping of the tail, is required for secretion. The truncated protein would not be detected by αPEP7, which is directed against the tail, although the catalytic domains would remain functional. We, therefore, examined the effects of a series of protease inhibitors on the secretion of tyrosinase by melan-a and melan-p1 cells. E64, an epoxysuccinyl peptide and a potent inhibitor of cysteine proteinases was found to be the most effective in reducing the amount of tyrosinase secreted into the media of melan-p1 cells (FIG. 5A), thus demonstrating that secretion of tyrosinase can be inhibited by blocking the activity of cysteinyl proteases.

If proteolysis and secretion of tyrosinase were the precipitating factor in the misrouting of tyrosinase, then E64 should increase melanin accumulation in melan-p1 cells. The effects of E64 were further investigated, and a potential synergy with tyrosine, which also reduced secretion into the media, examined. A range of E64 concentrations was tested at low (0.03 mM) and high (0.3 mM) tyrosine.

At 0.03 mM tyrosine, 12.5 µM E64 lowered secretion of tyrosinase into the medium from 7.1% to 4.0% (FIG. 5a), whereas at higher concentrations (25 µM), E64 was only slightly more effective (3.8% activity in media). E64 also reduced tyrosinase secretion at higher tyrosine concentrations (0.3 mM), reducing the tyrosinase in the medium from 6.5% to 3.9%. The higher concentration of E64 was not more effective. Surprisingly, E64 reduced intracellular melanin production at high concentrations of tyrosine. Thus, despite its ability to diminish proteolysis and secretion of tyrosinase from melan-p1 cells, E64 was not able to cause tyrosinase to re-route to the melanosome and begin melanin synthesis and deposition.

Example 4

Comparison of Ultrastructure and Distribution of Tyrosinase in Melan-a and Melan-p1 Cells Melanocytes were seeded into Lab-Tek chamber slides (Nunc, Inc., Naperville, Ill.) and grown to 90% confluence. Cultured melanocytes were fixed in wells with half-strength Karnovsky's fixative (Strum, et al. (1970) *J. Ultrastruct. Res.* 31(3):323-36) in 0.2 M sodium cacodylate buffer at pH 7.2 for 30 minutes at room temperature. For dihydroxyphenylalanine (DOPA) (Sigma, St. Louis, Mo.) histochemistry, fixed cells were incubated in 0.1% L-DOPA twice for 2.5 hours. The cells were washed 3 times in buffer and treated with 1.0% osmium tetroxide containing 1.5% potassium ferrocyanide (Strum, supra) for 30 minutes. The cells were washed, stained en bloc with 0.5% uranyl acetate for 30 minutes, dehydrated, and embedded in Eponate 12. Areas of the Epon case were cut out and mounted on Epon pegs and sectioned on an RMC MT 6000-XL ultramicrotome. Ultrathin sections were stained with aqueous solutions of uranyl acetate (2%) and lead citrate (0.3%) for 15 minutes each, and then viewed and photographed in a JEOL JEM-IOOCX transmission electron microscope.

Previous studies have shown that deficiency of the P protein results in both ultrastructural aberrations (Moyer, 1966, *Am. Zool.* 6:43-66; Sidman and Pearlstein, 1965, *Dev. Biol.* 12:93-116; Orlow and Brilliant, 1999, *Exp. Eye Res.* 68:147-154), as well as abnormal subcellular localization of tyrosinase (Potterf et al., 1998, supra). In order to investigate both features simultaneously, we determined the subcellular architecture and the distribution of tyrosinase in melan-a and melan-p1 cells by electron microscopy with and without DOPA histochemistry.

Figure 6B:
FIGS. 6A and 6B are representations of electronic micrographs demonstrating the ultrastructure of cultured melanocytes. The peri-nuclear area of melan-a (A) and melan-p1 (B) melanocytes demonstrate the Golgi apparatus (G). Melanosomes in the melan-a cell are of stage I, II, III, and predominantly stage IV (arrows). Melanosomes in melan-p1 cells are predominantly stage I and II with an occasional early stage III (arrowheads); no stage IV melanosomes were observed. BAR=1.0 micron.
Figure 6A:

As reported previously (Rosemblat et al., 1998, *Exp. Cell Res.* 239:344-352), cultured melan-a cells, wild type at the p locus, contained melanosomes that were predominantly of stage IV maturation (FIG. 6A). In contrast, p-null melan-p1 cells exhibited melanosomes that were predominantly stage I and II and occasionally stage III (FIG. 6B).

Figure 7A:
FIGS. 7A and 7B are representations of electronic micrographs demonstrating ultrastructure of cultured melanocytes processed for DOPA histochemistry. The perinuclear area of melan-a (A) and melan-p1 (B) melanocytes demonstrating the Golgi apparatus with DOPA reaction product in the cisternae and 50 nm vesicles of the TGN (G). The 50 nm vesicles are confined to the TGN in the melan-a cells and radiate away from the TGN in melan-p1 cells (arrowheads), and can be observed in close proximity to the plasma membrane (inset). Occasional stage III melanosomes are noted (arrows). BAR=1.0 micron.
Figure 7B:
Figure 8B:
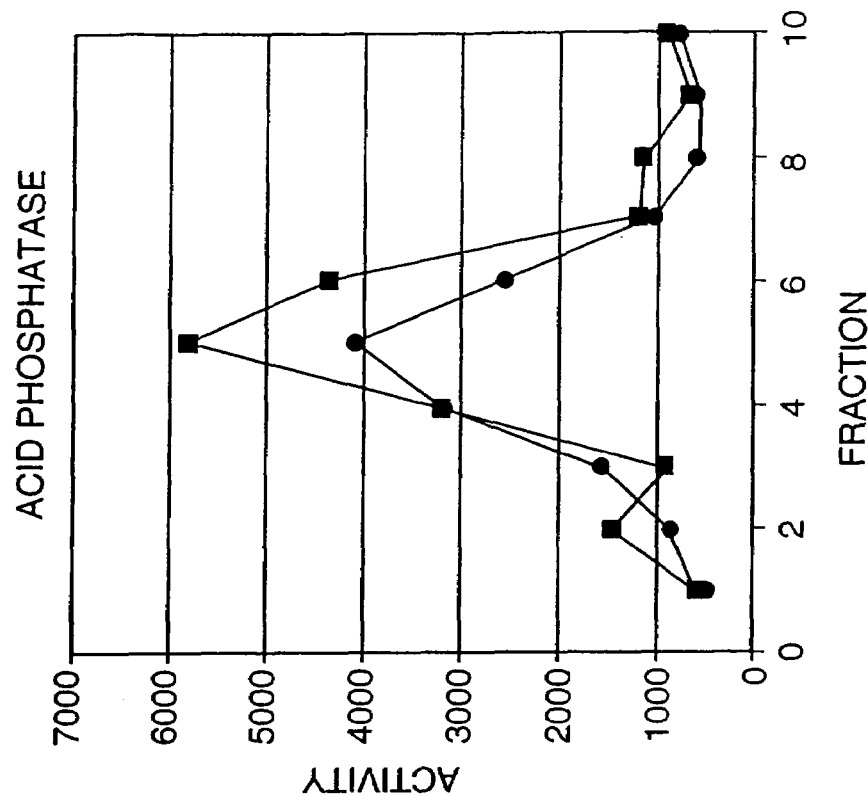
FIGS. 8A and 8B are graphic presentations demonstrating acid phosphatase targeting in melan-A and melan-P cells. Acid phosphatase activity was measured in fractionated membranes from melan-a (squares) and melan-p cells (circles) as described below in Example 5.
Figure 8A:
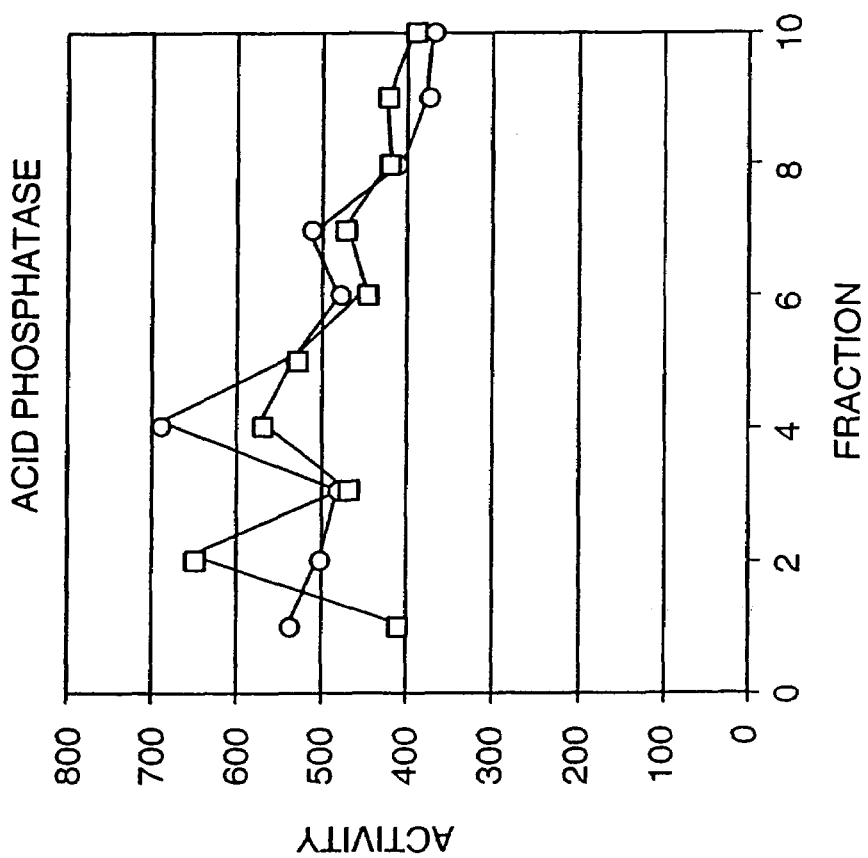
Figure 12B:
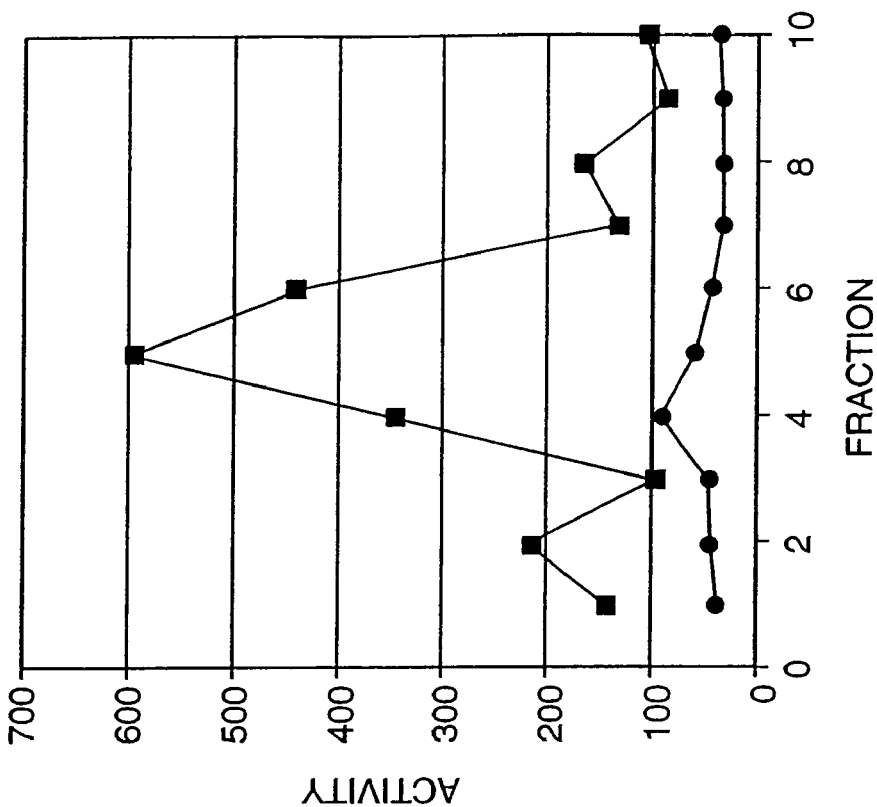
FIGS. 12A and 12B are graphic presentations demonstrating β-glucuronidase targeting in melan-A and melan-P cells. β-glucuronidase activity was measured in fractionated membranes from melan-a (squares) and melan-p cells (circles) as described below in the Example 5.
Figure 12A:
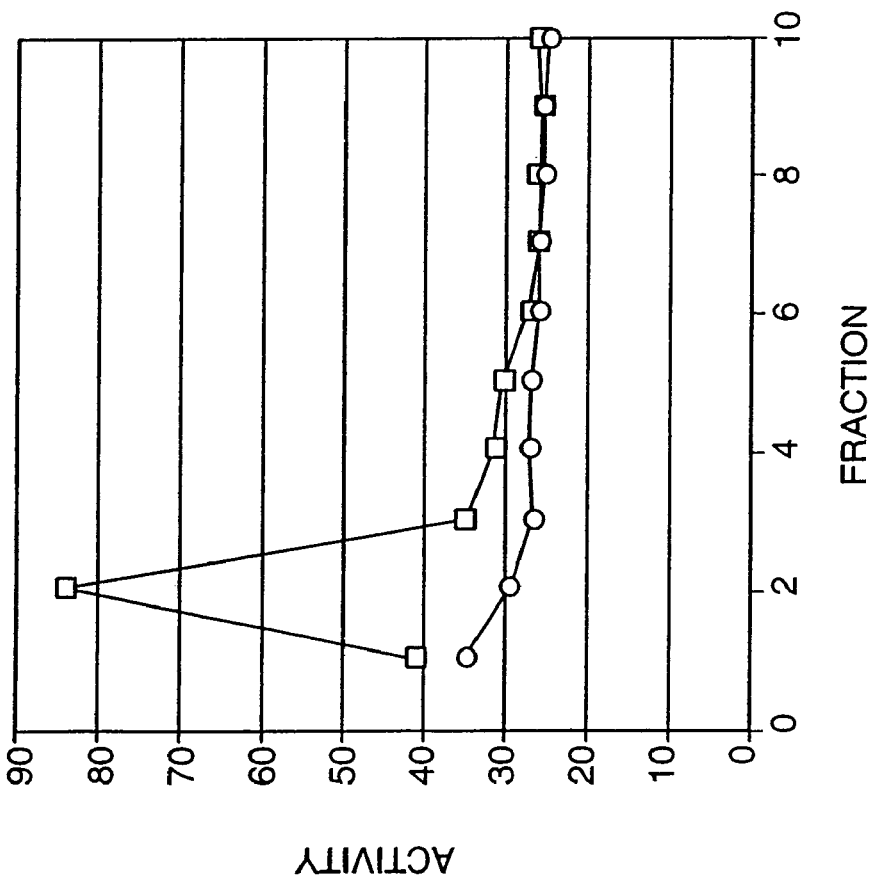

Upon DOPA incubation of melan-a cells, tyrosinase activity was demonstrated in the trans Golgi network (TGN) and in 50 nm vesicles which were confined to the vicinity of the Golgi apparatus (FIG. 7A). DOPA treated melan-p1 cells also demonstrated reaction product in the TGN and neighboring 50 nm vesicles (FIG. 7B). In addition, reaction product was present in some melan-p1 melanosomes. However, many melanosomes, both in the cell body as well as in the dendrites, remained devoid of reaction product (FIG. 7B). Unlike melan-a cells (FIG. 7A), melan-p1 cells exhibited reaction product in 50 nm vesicles well outside of the peri-nuclear Golgi area (FIG. 7B) and in close proximity to the plasma membrane (FIG. 7B) suggesting an abnormal accumulation of tyrosinase in a population of vesicles.

The lack of P protein resulted in the proliferation of small tyrosinase-containing vesicles that were no longer limited to the area around the TGN. Tyrosinase was, therefore, either packaged into different vesicles in the two cell lines or, alternatively, the vesicles were the same, but their routing was disrupted in the absence of P protein. Tyrosinase in these aberrant vesicles could be detected by DOPA staining and was thus enzymatically active. The increase in mature melanosomes in melan-p1 cells cultured in high tyrosine was not accompanied by a major reduction in the number of 50 nm vesicles, suggesting partial, but not complete, correction of the p phenotype by tyrosine.

Example 5

Targeting of Lysosomal Hydrolases in Melan-a and Melan-p Cells

This experiment demonstrates that melan-p cells do not properly target a certain class of lysosomal hydrolases to the lysosome.

Melan-a and melan-p cells as described above in Example 1 were seeded to high density and grown in low tyrosine (14 µM) DME medium. Large granule and small granule fractions were prepared and centrifuged on pre-layered sucrose gradients as described in Rosemblat et al., 1994, supra; and Seiji, 1963, *Annals N.Y. Acad. Sci.*, 100:497-533. Fractions were collected from the top down.

Appropriate reaction substrates for the lysosomal enzyme assays prepared in 0.2 M sodium acetate, 1% TritonX-100 were as follows:

β-hexosaminidase—4 mM 4-methylumbellifery-N-acetyl-β-D-glucosaminide

β-glucosidase—4.6 mM 4-methylumbelliferyl-N-acetyl-β-D-glucoside

β-glucuronidase—4.6 mM 4-methylumbelliferyl-N-acetyl-β-D-glucoronide

β-galactosidase—4.6 mM 4-methylumbelliferyl-N-acetyl-β-D-galactoside

Acid phosphatase—22.5 mM 4-methylumbelliferyl-phosphate

The reaction mix was prepared in 96 well flat bottom plates. Each well was loaded with 25 µl of a gradient fraction, 2.5 µl 1M sodium acetate and 27.5 µl of the appropriate substrate mix. The plates were covered with parafilm and incubated at 37° C. β-hexosaminidase reactions were incubated for 50 minutes, β-glucosidase, β-glucuronidase and β-galactosidase reactions were incubated for 20 minutes, and acid phosphatase reactions were incubated for 10 minutes. Reaction was stopped by addition of 200 μl of stop buffer (132 mM glycine, 68 mM sodium chloride, 83 mM anhydrous sodium carbonate), and plates read immediately using an excitation wavelength of 370 nm and an emission wavelength of 460 nm.

In both melan-a and melan-p cells, very little of the lysosomal hydrolases were detected in the small granule fraction (see FIGS. 8-12). This result was expected because the small granule fraction consisted of mostly small vesicles in which lysosomal hydrolases do not normally accumulate. The large granule fraction contains endoplasmic reticulum, Golgi organelles, lysosomes and melanosomes and, hence, should contain most of the lysosomal hydrolases. With respect to acid phosphatase, there was only slightly less overall activity for the enzyme in large granule fractions from melan-p cells as compared to those from melan-a cells (FIG. 8B). Additionally, there was a minor shift in localization of acid phosphatase to slightly less dense fractions in the melan-p cells as compared to melan-a cells. However, with respect to the other lysosomal hydrolases assayed, the differences between melan-a and melan-p cells was dramatic. In fact, the overall activity of β-hexosaminidase, β-glucosidase, β-glucuronidase and β-galactosidase was significantly reduced in melan-p cells as opposed to melan-a cells (see FIGS. 9-12, right panels). This loss of activity could not be attributed to a shift of the enzymes within the cells because whole cell extracts demonstrated the similar significant decreases in activity of β-hexosaminidase, β-glucosidase, β-glucuronidase and β-galactosidase in melan-p cells as opposed to melan-a cells, but with essentially no difference in the total amounts of alkaline phosphatase between melan-p and melan-a cells (results not shown). While the same large granule fractions from melan-a cells that contained acid phosphatase also contained most of the β-hexosaminidase, β-glucosidase, β-glucuronidase and β-galactosidase activities, melan-p cells had a significant reduction in activity of these enzymes in the large granule fractions. Thus, β-hexosaminidase, β-glucosidase, β-glucuronidase and β-galactosidase enzymes do not accumulate correctly in lysosomes in melan-p cells.

Unlike acid phosphatase, the enzymes β-hexosaminidase, β-glucosidase, β-glucuronidase and β-galactosidase are not transported to the cell surface prior to eventually reaching the lysosome. Instead, these enzymes are transported from the trans-Golgi network to the late endosome via the activity of the M6P/IGF-II receptor. The differences in targeting of these two classes of lysosomal hydrolases in melan-p cells versus melan-a cells indicates that disruption of P protein function affects M6P/IGF-II receptor-mediated targeting. Based on our results showing the secretion of tyrosinase from melan-p cells, and the intracellular depletion of β-hexosaminidase, β-glucosidase, β-glucuronidase and β-galactosidase in large granule fractions from the same cells, this class of lysosomal enzymes should be secreted from the melan-p cells. Accordingly, targeting of these enzymes, assayed by an increase in secretion or a reduction in accumulation in lysosomal membrane fractions, can also be used as part of an assay to screen for compounds that affect the function of P protein.

Example 6

Effects of Compounds that Alter Late Endosomal/Lysosomal Trafficking

Experiments were conducted in order to determine the affect on melanin production of various compounds that alter late endosomal/lysosomal trafficking. Cells utilized in these studies were melan-a melanocytes as described above.

Melan-a melanocytes were incubated in DMEM (10% fetal calf serum, 2 mM L-glutamine, 1 mM sodium pyruvate, 1% MEM non-essential amino acids 100×, 50 μ/L penicillin, 50 μg/L streptomycin). Immediately before using the medium, tetradecanoyl phorbol acetate (TPA) was added at 200 nM. Cells were seeded in T-25 flasks with $4 \times 10^4$ cells/ml×4.5 ml/flask (10-20% confluent) and were grown at 37° C. with 5% $CO_2$. Twenty-four hours later, a compound to be tested (diluted in 0.5 ml media) was added to the media. Forty-eight hours after the addition of drug, both the media and drug were changed. Cells were harvested after an additional 48 or 72 hours (100% confluent).

In harvesting the cells, the reagents and cells were kept at 4° C. Briefly, the media was removed from the cells, and one milliliter of media was reserved if needed for the tyrosinase assay. The cells were then rinsed with approximately 500 μl cold 1× phosphate buffered saline (PBS) until the PBS rinse was clear. Cold extraction buffer (50 mM Tris, (pH 7.5), 2 mM EDTA (pH 7.8), 150 mM NACE, and 1% Triton x-100 (Sigma, St. Louis, Mo.), (500 μl) was added, and the sample was allowed to incubate on ice for a few minutes or until cells began to peel off the bottom of the flask. After tapping the flask to encourage the cells to fall off, the 500 μl of the extraction buffer/cells were removed and placed in a microfuge tube. After spinning the sample for 5 minutes at 14,000×g at 4° C., the supernatant was removed and saved in a microfuge tube for the protein assay (and tyrosinase assay, if necessary). The cell pellets were either stored at 4° C. overnight or at −20° C. for longer periods before assaying for melanin.

In order to assay for melanin, 300-500 μl of ethanol/ether (1:1) was added to each pellet of cells. The sample was vortexed and allowed to stand for approximately 10 minutes or until precipitated protein was visible in the solvent. If necessary, pellets were gently crushed with a microfuge tube pestle. Care was taken not to break the pellet(s) into many small pieces which would have made removing the solvent (and leaving melanin behind) difficult. Using a glass pipette, the solvent/protein was removed, being careful not to remove melanin. The extraction steps were repeated, and the pellets allowed to dry. Next, 250 μl of 2 N NaOH in 20% dimethylsulfoxide (DMSO) was added to each microfuge tube. The samples were heated at 66-70° C. until the melanin was completely dissolved. For each sample tested, 200 μl of the NaOH/melanin solution was transferred to a 96-well plate. 2 N NaOH in 20% DMSO was used as a blank, and the samples were read at a wavelength of 490 nm. The data were reported as absorbance of melanin per protein calculated for the total sample.

In order to determine the effects of progesterone on melanin production, melan-a melanocytes were incubated in the presence of 20 uM progesterone (Sigma, St. Louis, Mo.) as outlined above. In addition, cells were also separately treated with either 300 uM PTU (Sigma, St. Louis, Mo.), a direct inhibitor of tyrosinase, or 100 uM IBMX (Sigma, St. Louis, Mo.), a phosphodiesterase inhibitor.

Figure 13:
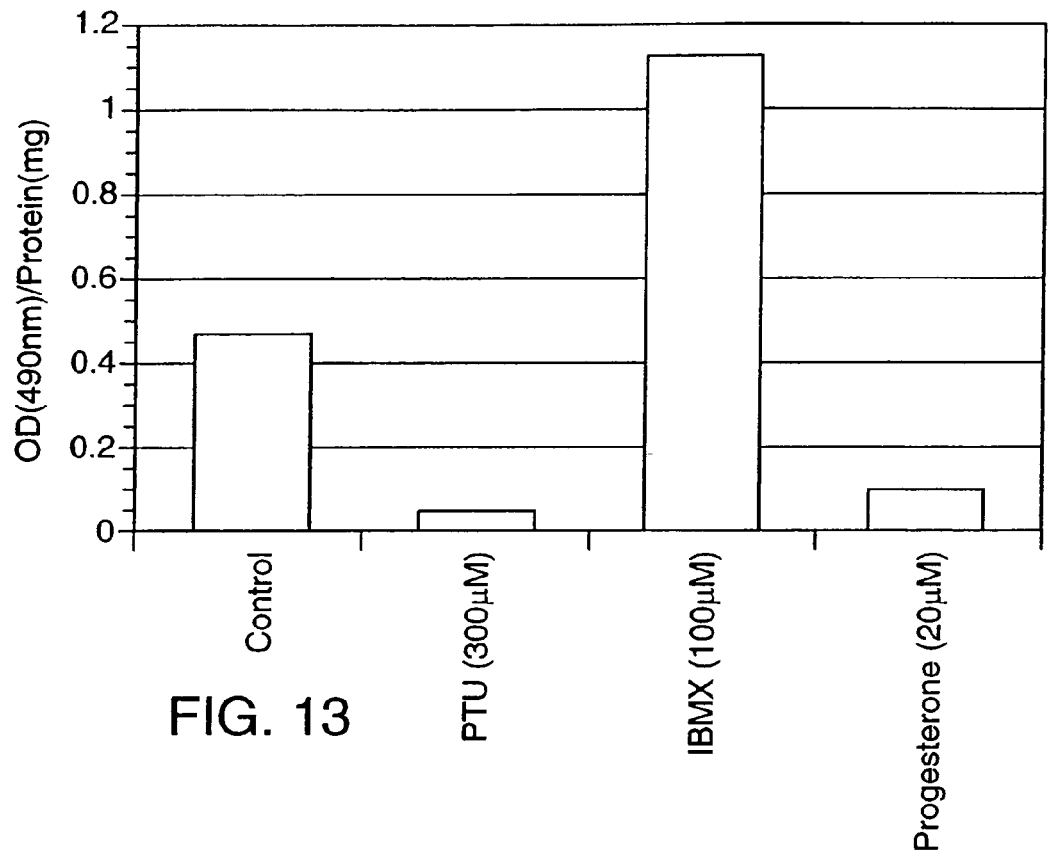
FIG. 13 is a graphic representation providing melanin optical density (OD) determinations for melan-a melanocytes treated with progesterone. Cells were treated with no drug, i.e., control, 300 µM 1-phenyl-2-thiourea (PTU), 100 µM isobutylmethylxanthine (IBMX), a phosphodiesterase inhibitor, or 20 µM progesterone.

The results, as presented in FIG. 13, indicate that progesterone decreases pigmentation in melan-a melanocytes an average of 52% at 20 µM. Other experiments indicated that progesterone decreases pigmentation an average of 45% at 10 µM.

In order to determine the effects of hydrophobic amines on melanin production, melan-a melanocytes were incubated in the presence of 20 µM imipramine (IMP), a cationic amphiphilic drug (Sigma, St. Louis, Mo.) following the procedure outlined above. In addition, cells were also separately treated with either 300 µM PTU (Sigma, St. Louis, Mo.), or 100 µM IBMX (Sigma, St. Louis, Mo.).

Figure 14:
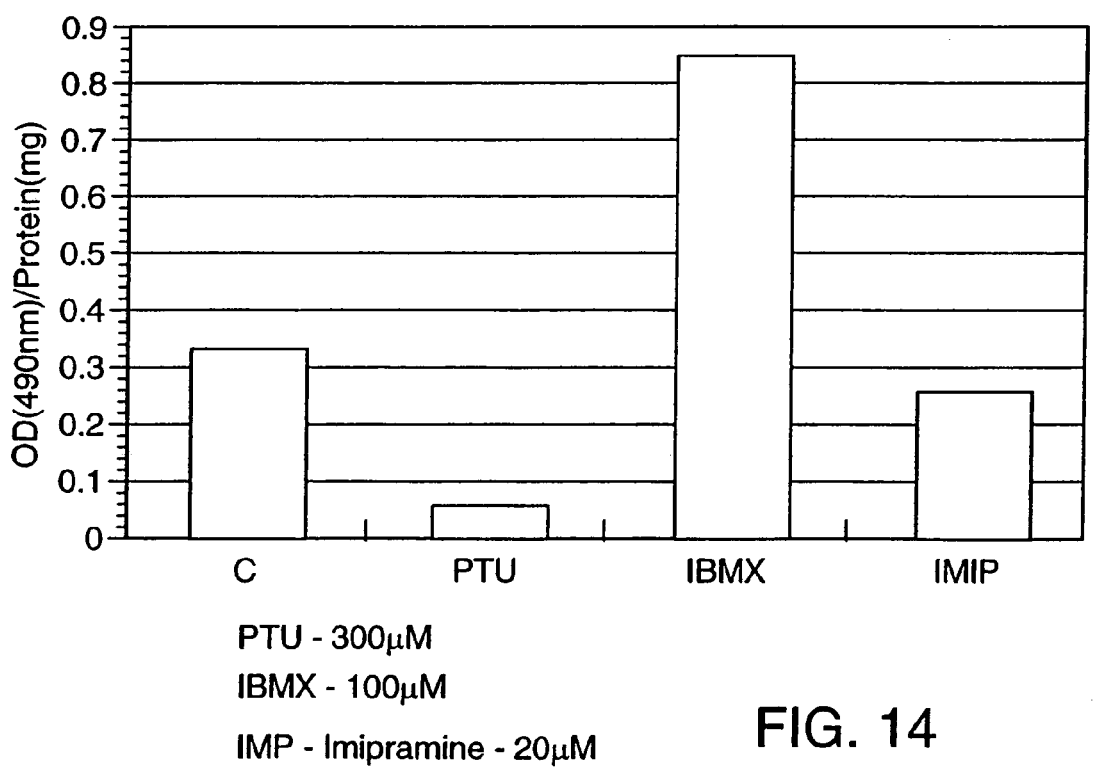
FIG. 14 is a graphic representation providing melanin optical density (OD) determinations for melan-a melanocytes treated with imipramine. Control cells received no drug treatment, and test cells were treated with 300 µM PTU, 100 µM IBMX, or 20 µM imipramine (IMP).

The results, as presented in FIG. 14, demonstrate that IMP decreases pigmentation 33% at 20 µM.

Figure 15:
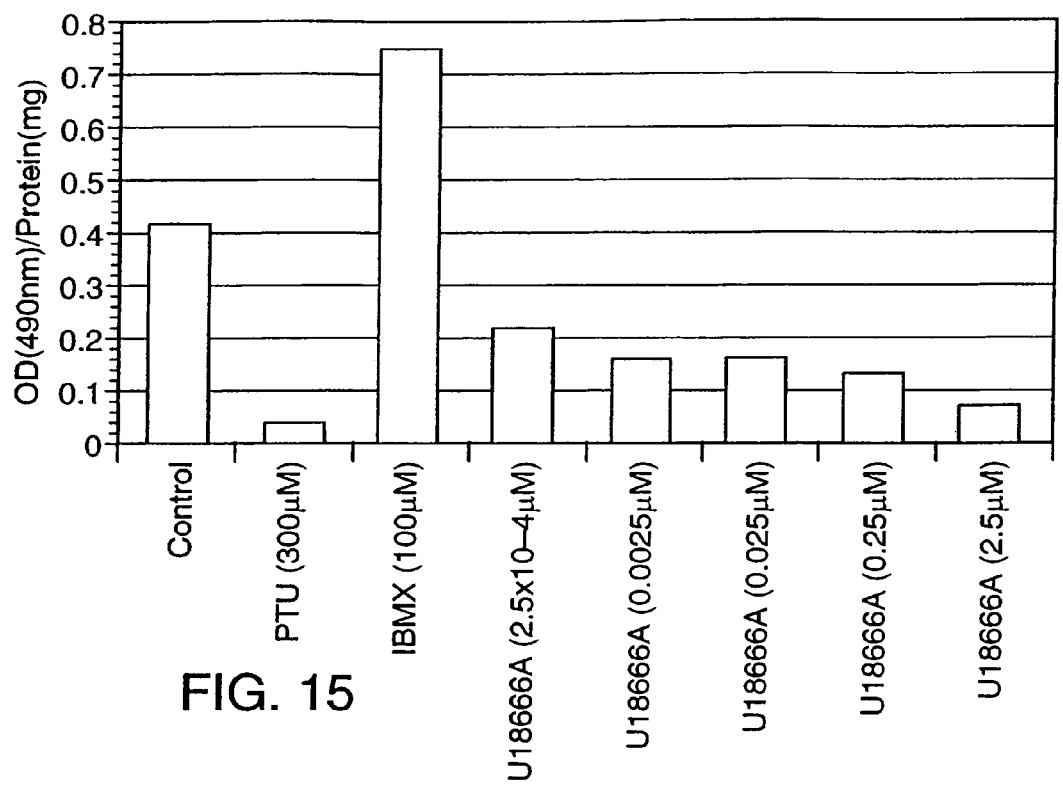
FIG. 15 is a graphic representation providing melanin optical density (OD) determinations for melan-a melanocytes incubated with 3β-(2-diethylaminoethoxy)-androstenone HCl (hereinafter "U18666A"). Control cells received no drug treatment, and test cells were treated with 300 µM PTU, 100 µM IBMX, $2.5 \times 10^{-4}$ µM U18666A, $2.5 \times 10^{-3}$ µM U18666A, 0.025 µM U18666A, 0.25 µM U18666A, or 2.5 µM U18666A.

Experiments were also done to test the affects of various concentrations of U18666A on melanin production. Results of this experiment are presented in FIG. 15 and indicate that U18666A decreases pigmentation an average of 60% as compared to control at a concentration of 2.5 µM and shows a significant decrease in pigmentation to a concentration as low as 2.5 nM.

Experiments were also conducted in order to test several analog compounds of U18666A for an affect on pigment production. The results of this experiment are presented in FIG. 16. Most notable are the U18666A derivatives CP-352369, CP-598755-01, CP-602367, UK-204039, UK204041, and UK204042 (Pfizer, Inc., Groton, Conn.), which significantly decrease melanin production in melan-a melanocytes.

Figure 17:
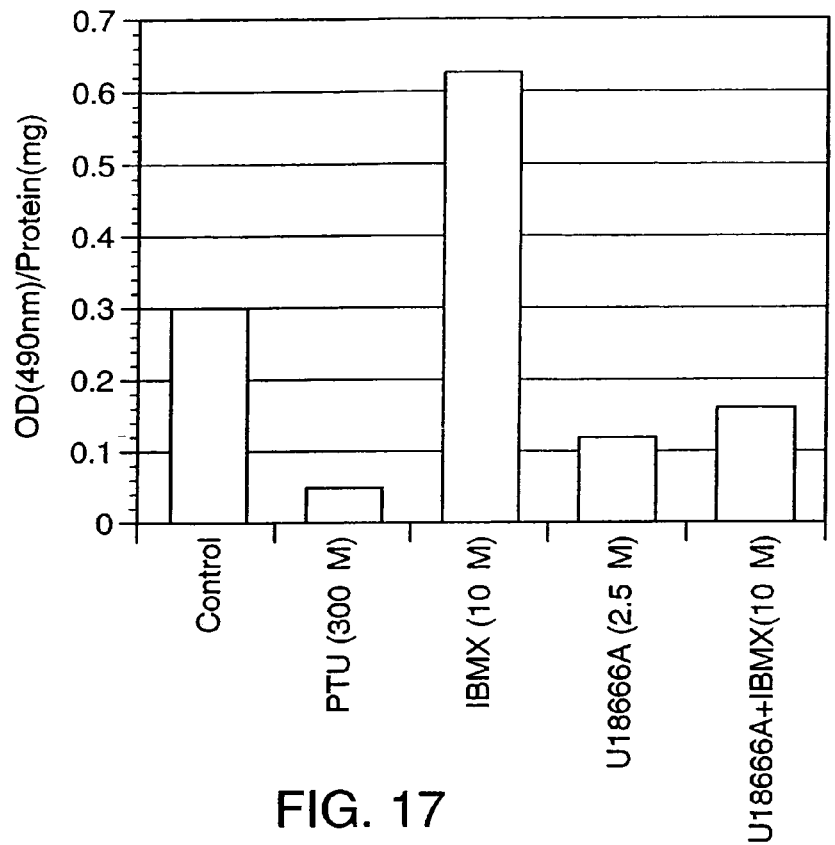
FIG. 17 is a graphic representation providing melanin optical density (OD) determinations for melan-a melanocytes cells treated with U18666A in combination with IBMX. Control cells received no drug treatment, and test cells were treated with 300 µM PTU, 10 µM IBMX, 2.5 µM U18666A, or 10 µM IBMX combined with 2.5 µM U18666A.

In order to determine if U18666A can reduce the effect of IBMX (Sigma, St. Louis, Mo.) alone, which normally would affect melan-a cells by increasing pigment production, cells were incubated with the combination of U18666A and IBMX (Sigma, St. Louis, Mo.). The results are presented in FIG. 17. U18666A in combination with the phosphodiesterase inhibitor IBMX (Sigma, St. Louis, Mo.) reduces the effect of IBMX (Sigma, St. Louis, Mo.) alone by 75%.

Example 7

Exposure of Cells to U18666A Does Not Alter Tyrosinase Activity

In order to determine whether the decrease in the amount of melanin in cells exposed to the hydrophobic amine U18666A could be attributed to an affect on the activity of tyrosinase, the activity of tyrosinase in cells exposed to U18666A was determined. In these experiments, tritiated tyrosine is converted to dopaquinone by tyrosinase, where water is released as a product. By labeling tyrosine with $^3$H, tritiated water is released and is a measure of tyrosinase activity.

All samples were assayed in duplicate or triplicate (1 µl $^3$H-tyrosine (3H-Tyr) 46.0 Ci/mmole per sample (Amersham Pharmacia Biotech, Piscataway, N.J.). $^3$H-Tyr was divided equally among microfuge tubes for faster drying. The filled tubes were covered with parafilm and holes were poked through the parafilm with a syringe. The $^3$H-Tyr was dried in a speed vac for approximately 15 minutes. The $^3$H-Tyr was washed two times with an equal volume of ethanol. The $^3$H-Tyr was reconstituted in 10× its original volume with DOPA (Sigma, St. Louis, Mo.) (0.5 mg/ml DOPA in 0.1 M NaPO$_4$, pH 6.8). The $^3$H-Tyr samples were pooled together. Reaction mixtures were prepared in short borosilicate tubes as follows. Briefly, 10 µl $^3$H-Tyr was added to a 50 µl sample of 0.1 M NaPO$_4$ containing 1% Triton X-100. The sample was incubated for 1 hour at 37° C. in a water bath. To stop the reaction, 1.0 ml of 10% activated charcoal in 0.1 M citric acid was added and the sample was vortexed thoroughly. Activated charcoal stops the reaction by absorbing free-floating organic compounds, for example the $^3$H-Tyr. Next, the sample(s) were centrifuged for 5 minutes at 700 rpm. Supernatants were collected (670 µl) and loaded on cationic exchange columns packed with AG 50W-X8 Resin (200-400 mesh) (Bio-Rad Laboratories, Hercules, Calif.). Buffer (0.5 ml of 0.1 M citric acid) was loaded onto the column to wash sample through. Ten ml of scintillation fluid was added, and the sample was vortexed thoroughly. $^3$H activity was counted in scintillation counter.

Figure 18:
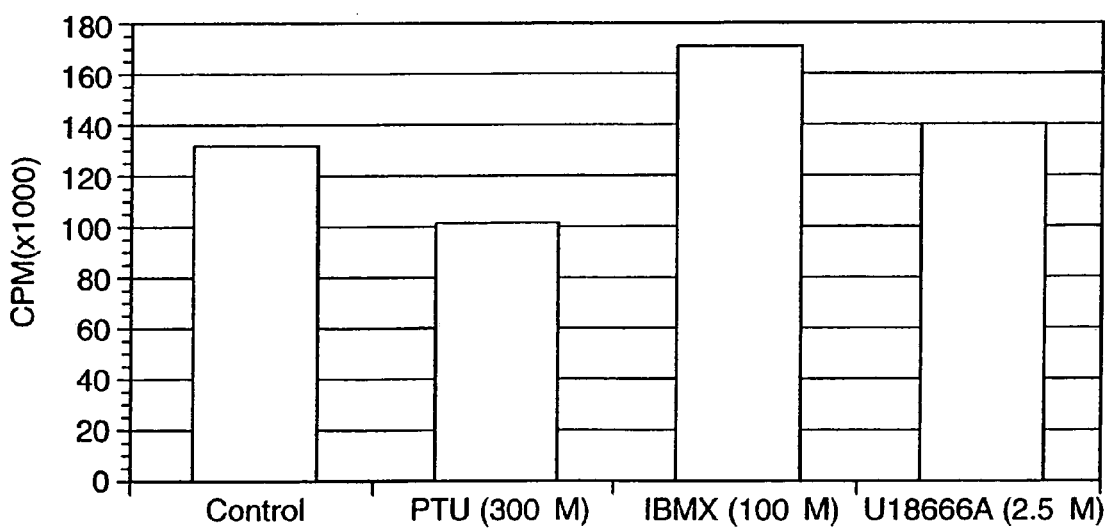
FIG. 18 is a graphic representation providing measurements of tyrosinase activity of extract from melan-a melanocytes incubated with U18666A Control cells received no drug treatment, and test cells were treated with 300 µM PTU, 10 µM IBMX, or 2.5 µM U18666A

The results of the experiment, presented in FIG. 18A, indicate that no significant difference in the total amount of tyrosinase activity is found in cells exposed to U18666A compared to the control, untreated cells. These results indicate that the decrease in melanin observed when melan-a melanocytes are exposed to U18666A cannot be attributed to a decrease in the total amount of tyrosinase in the cells, suggesting that the decrease in melanin is the result of altered localization of tyrosinase.

In order to confirm the results of the tyrosinase assay, the amounts of tyrosinase protein in control, untreated melan-a melanocytes and U186666A-treated melan-a melanocytes were compared by Western blot analysis. Standard procedures were followed for protein electrophoresis and protein transfer to a support membrane (see, e.g., *Molecular Cloning: A Laboratory Manual* (1989) Cold Spring Harbor, N.Y., Cold Spring Harbor Laboratory, 2$^{nd}$ edition, Sambrook, J., Fritsch, E. F., and Maniatis, T.) Briefly, protein samples were run on a 7.5% SDS polyacrylamide gel overnight at 35 volts. The proteins were transferred from the gel onto nitrocellulose over 1.5 hours at 400 mA Non-specific binding sites on the membrane were blocked by incubating the membrane in 3% milk in phophate buffered saline (PBS) for 1 hour. The membrane was then incubated with primary antibody (Pep 7, 1:2000, obtained from Vincent Hearing, NIH, Bethesday, Md.) in 3% milk in PBS overnight at 4° C. The membrane was washed with PBS with 0.05% Tween 20 added (PBS-T) for six times, five minutes each wash. After washing, the membrane was incubated with secondary antibody (horse radish peroxidase anti-rabbit, 1:2000, Amersham Life Science, Piscataway, N.J.) in 3% milk in PBS for 1 hour. Following washing for 8 times, 5 minutes each wash, with PBS-T, the membrane was incubated with ECL detection reagent. (NEN Life Science Products, Boston, Mass.) for 1 minute. Autoradiography was performed following standard procedures.

Results of the Western blot analysis shows that the total amount of tyrosinase in the cell after exposure to U18666A is not significantly less than the control, untreated cell.

Example 8

Exposure of Cells to U18666A Alters the Intracellular Localization of Tyrosinase In order to determine whether treatment with U18666A affects the cellular localization of tyrosinase, melan-a melanocytes were fractionated by sucrose gradient centrifugation after being exposed to U18666A.

Large granule and small granule fractions were prepared and centrifuged on pre-layered sucrose gradients as previously described in Seiji (1963) *Annals N.Y. Acad. Sci.* 100: 497-533.

Sucrose gradient fractions were collected from the top down, and the samples were analyzed for tyrosinase activity as previously described above.

Figure 19:
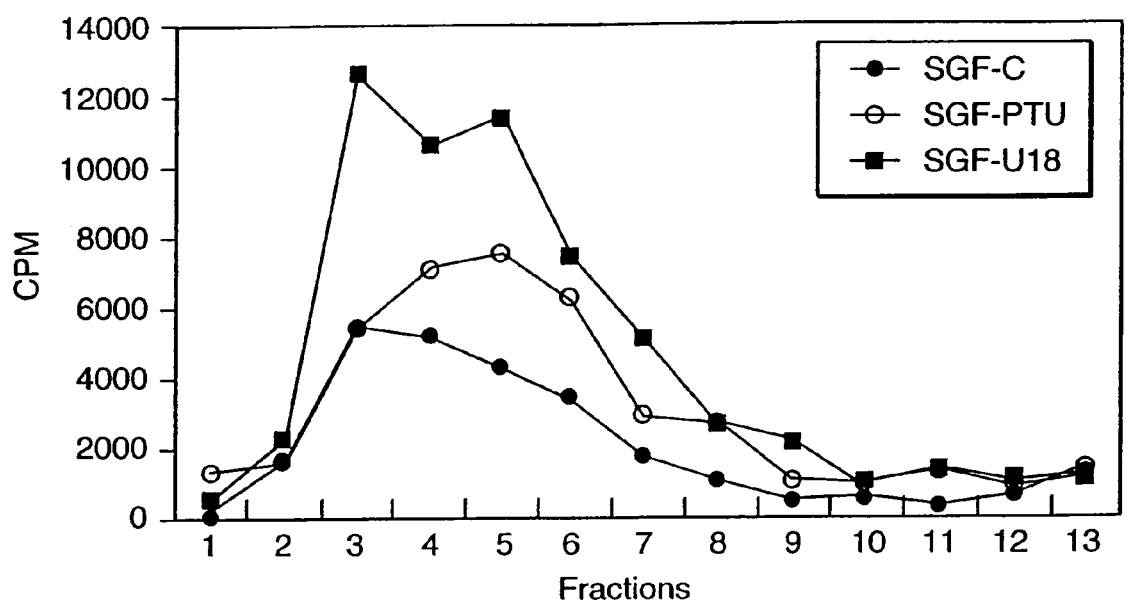
FIG. 19 is a graphic representation providing measurements of tyrosinase activity on the small granule fractions of a stepwise sucrose gradient fractionation of melan-a melanocytes treated with PTU and U18666A
Figure 20:
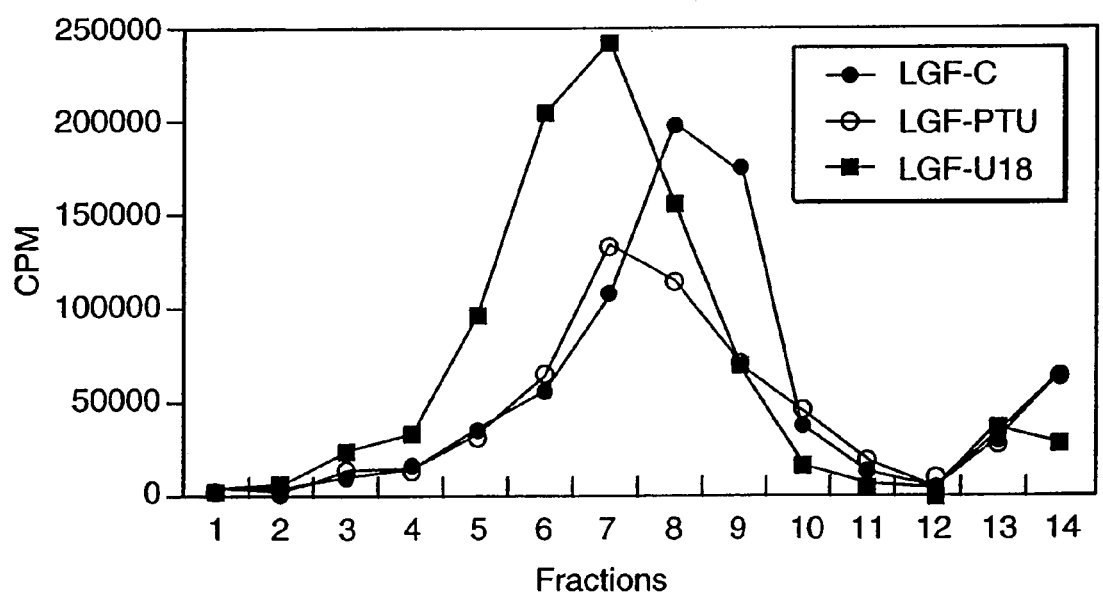
FIG. 20 is a graphic representation providing measurements of tyrosinase activity on the large granule fractions of a stepwise sucrose gradient fractionation of melan-a melanocytes treated with PTU and U18666A

The results are presented in FIG. 19 (small granule fractionation) and FIG. 20 (large granule fractionation). These data indicate that the localization of tyrosinase is markedly affected by exposure to U18666A. For example, in FIG. 19 a shift in the distribution of tyrosinase is evident in comparing fraction 5 of the control and U18666A samples. The change in the distribution of tyrosinase is even more evident in the large granule fractionation study (see FIG. 20, fractions 6-8, for the large granule fraction control (LGF-C) and large granule fraction U18666A (LGF-U18)).

These results support the position that U18666A inhibits melanin production by altering the normal cellular pattern of tyrosinase localization.

Example 9

Exposure of Cells to Bafilomycin or Concanamycin

Wild type melan-a (a/a, P/P), an immortalized melanocyte line derived from C57BL6J mice; melan-p1 melanocytes (a/a, $p^{cp}/p^{25H}$), an immortalized line derived from p-null mice; melan-p1 (P10), a melan-p1 line stably transfected with an expression plasmid carrying the pink-eyed dilution gene; B16, an amelanotic mouse melanoma cell line; and B16F10, a slightly pigmented mouse melanoma cell line, were used in this study.

Cells were cultured in RMPI-1640 (Sigma, St. Louis, Mo.) supplemented with 10% fetal calf serum, 5% sodium pyruvate, 5% glutamate, 5 units/ml penicillin, 5 μg/ml streptomycin, 1% non-essential amino acids and 200 nM 12-O-tetradecanoyl phorbol 13-acetate for 24 hours The medium was than replaced with RPMI containing either 0, 1, 2 or 2.5 μM bafilomycin A1 (Sigma, St. Louis, Mo.) or 0, 0.5 or 1.0 μM concanamycin A (Sigma, St. Louis, Mo.). After 36 hours, the medium was removed and the cells extracted in 100 μl extraction buffer (1% Triton-X 100, 50 mM Tris, 2 mM EDTA, 150 mM NaCl). The samples were centrifuged at 13,000 rmp in a microfuge tube for 30 minutes. The supernatant was removed and protein content determined using a protein assay kit (Bio-Rad, Richmond, Calif.).

The melanin content in the pellet was determined following removal of the supernatant Each sample was treated with 0.5 ml ethanol:ether (1:1), vortexed and incubated at room temperature for 10 minutes. The solvent was removed and the melanin was washed again with ethanol:ether (1:1). Following removal of the second wash, 200 μl 2 N sodium hydroxide, 20% DMSO was added and the sample heated to 60° C. until the melanin was dissolved. The sample was then transferred to a 96-well plate and the optical density was read at 490 nm. The optical density was then normalized to protein concentration in the corresponding lysate.

Figure 21:
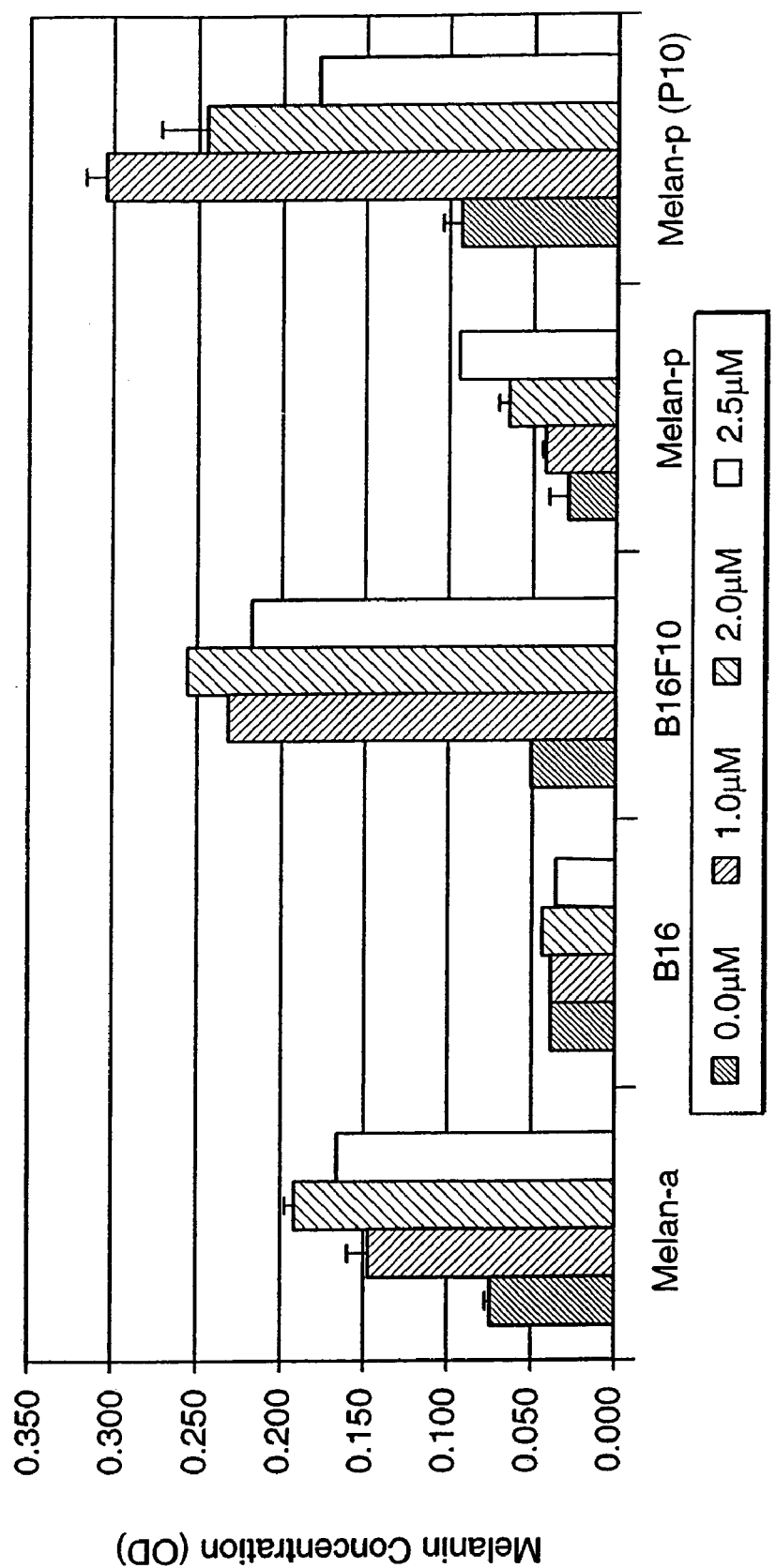
FIG. 21 is a graphic representation of the effects of bafilomycin A1 treatment on melanin content in melan-a, melan-p, B16 and melan-p (P10) cells at various concentrations (0.0 µM, 1.0 µM, 2.0 µM, and 2.5 µM). Melan-a cells are wild-type melanocytes; melan-p cells are melanocytes with diminished or absent P protein activity; B16 cells are melanoma cells that lack tyrosinase and P protein; B16F10 cells are melanocytes that have detectable levels of tyrosinase, but not P protein; and melan-p (P10) cells are melanocytes with diminished or absent P protein activity stably transfected with an expression plasmid carrying the pink-eyed dilution gene.
Figure 22:
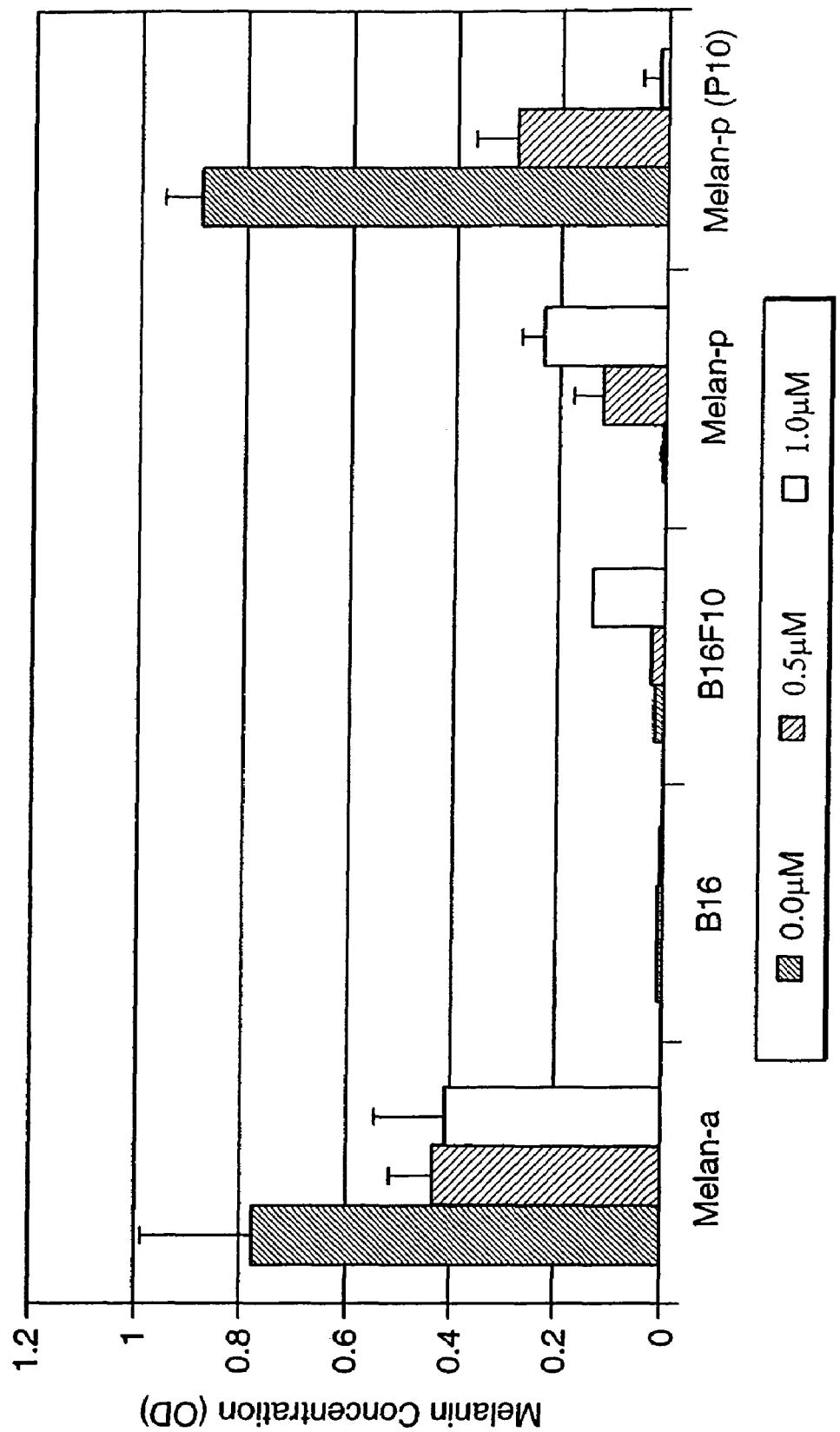
FIG. 22 is a graphic representation of the effects of concanamycin A treatment on melanin content in melan-a, melan-p, B16 and melan-p (P10) cells at various concentrations (0.0 µM, 0.5 µM, and 1.0 µM).

FIGS. 21 and 22 show the results obtained after bafilomycin A1 or concanamycin A treatment, respectively. FIG. 21 demonstrates that the melanin content of wild type melanocytes (Melan-a) and melanocytes with diminished or absent P protein activity stably transfected with an expression plasmid carrying the pink-eyed dilution gene (Melan-p (P10)) initially increases in the presence of μM concentrations of bafilomycin A1 but drops at the highest concentration tested. Melanin levels in a p-null line (Melan-p) increased with an increase in bafilomycin A1 concentration. A melanoma line lacking tyrosinase and P protein (B16) does not respond to bafilomycin A, while a second melanoma line which has detectable levels of tyrosinase, but not P protein (b16F-10) demonstrates increasing pigmentation which diminishes at higher concentrations.

FIG. 22 shows that the melanin content of wild type melanocytes (Melan-a) and melanocytes with diminished or absent P protein activity stably transfected with an expression plasmid carrying the pink-eyed dilution gene (Melan-p (P10)) is decreased in the presence of μM concentrations of concanamycin A, while melanin levels in a p-null line (Melan-p) increase with an increase in concanamycin A concentration A melanoma line lacking tyrosinase and P protein (B16) does not respond to concanamycin A, while a second melanoma line which has detectable levels of tyrosinase, but not P protein (B16F10) demonstrates increasing pigmentation which diminishes at higher concentrations.

These results indicate that melanogenesis is activated in p-null melanogenesis by exposure to the ATPase inhibitors bafilomycin and/or concanamycin.

EQUIVALENTS

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims.

What is claimed is:

1. A method of screening for compounds that inhibit melanogenesis, the method comprising: treating mammalian melanogenic cells expressing a tyrosinase-encoding gene with a test compound in vitro, and determining the amount of tyrosinase secreted by the mammalian melanogenic cells in the presence of the test compound; wherein an increase in the amount of tyrosinase secreted by the mammalian melanogenic cells in the presence of the test compound as compared to in the absence of the test compound indicates that the test compound is a candidate for a compound that inhibits melanogenesis.

2. The method of claim 1, wherein the mammalian melanogenic cells further express a P protein-encoding gene, and wherein the increase in the amount of tyrosinase secreted in the presence of the test compound as compared to in the absence of the test compound is dependent upon the expression of the P protein-encoding gene.

3. The method of claim 1, wherein the cellular localization of tyrosinase is detected by assaying for tyrosinase activity, or by assaying for the presence of tyrosinase protein using immunological techniques.

4. The method of claim 1, further comprising the step of assaying the amount of tyrosinase associated in a high molecular weight complex in the presence of the test compound, wherein a decrease in the amount of tyrosinase associated in a high molecular weight complex in the presence of the test compound as compared to in the absence of the test compound indicates that the test compound is a candidate for a compound that inhibits melanogenesis.

5. The method of claim 1, further comprising the step of assaying the amount of tyrosinase-related protein-1 (TRP-1) or tyrosinase-related protein-2 (TRP-2) protein associated in a high molecular weight complex in the presence of the compound, wherein a decrease in the amount of TRP-1 or TRP-2 protein associated in a high molecular weight complex in the presence of the test compound as compared to in the absence of the test compound indicates that the test compound is a candidate for a compound that inhibits melanogenesis.

6. The method of claim 1, further comprising the step of assaying the number or size of melanosomes in the mammalian melanogenic cells in the presence of the compound, wherein a decrease in the number or size of melanosomes in the mammalian melanogenic cells in the presence of the test compound as compared to in the absence of the test compound indicates that the test compound inhibits melanogenesis.

7. The method of claim 1, further comprising the step of assaying the mass or length of tyrosinase in the mammalian melanogenic cells in the presence of the compound, wherein a decrease in the mass or length of tyrosinase in the mammalian melanogenic cells in the presence of the test compound as compared to in the absence of the test compound indicates that the test compound is a candidate for a compound that inhibits melanogenesis.

8. The method of claim 1, further comprising the step of assaying for the levels and/or targeting of lysosomal hydrolases in the mammalian melanogenic cells in the presence of the compound, wherein a decrease in accumulation of lysosomal hydrolases that are transported via the mannose-6-phosphate/insulin-like growth factor type II receptor (M6P/IGF-II receptor) in the lysosome in the mammalian melanogenic cells in the presence of the test compound as compared to in the absence of the test compound indicates that the test compound is a candidate for a compound that inhibits melanogenesis.

9. The method of claim 1, wherein the mammalian melanogenic cells are grown in the presence of low tyrosine.

10. The method of claim 1 wherein the mammalian melanogenic cells are melanocytes, or melanoma cells.

11. A method of screening for compounds that increase melanogenesis comprising: treating mammalian melanogenic cells expressing a tyrosinase-encoding gene with a test compound in vitro, and determining the amount of tyrosinase secreted by the mammalian melanogenic cells in the presence of the test compound; wherein a decrease in the amount of tyrosinase secreted by the mammalian melanogenic cells in the presence of the test compound as compared to in the absence of the test compound indicates that the test compound is a candidate for a compound that increases melanogenesis.

12. A method of screening for compounds that inhibit melanogenesis, the method comprising: treating mammalian melanogenic cells expressing a tyrosinase-encoding gene with a test compound in vitro in a medium containing 0.01 mM to 0.05 mM tyrosine, and determining the cellular localization of tyrosinase in the presence of the test compound; wherein an increase in the amount of tyrosinase found in non-melanosomal vesicles in the presence of the test compound as compared to in the absence of the test compound indicates that the test compound is a candidate for a compound that inhibits melanogenesis.

* * * * *